(12) United States Patent
Nibbering et al.

(10) Patent No.: US 10,130,677 B2
(45) Date of Patent: Nov. 20, 2018

(54) ANTIMICROBIAL PEPTIDE AND USES THEREOF

(71) Applicants: Academisch Ziekenhuis Leiden h.o.d.n. LUMC, Leiden (NL); Academisch Medisch Centrum, Amsterdam, Zuidoost (NL)

(72) Inventors: Petrus Hendricus Nibbering, Leiden (NL); Anna de Breij, Leiden (NL); Robert Alexander Cordfunke, Leiden (NL); Sebastianus Antonius Johannes Zaat, Amsterdam Zuidoost (NL); Jan Wouter Drijfhout, Leiden (NL)

(73) Assignees: Academisch Ziekenhuis Leiden h.o.d.n. LUMC, Leiden (NL); Academisch Medisch Centrum, Amsterdam Zuidoost (NL)

( * ) Notice: Subject to any disclaimer, the term of this patent is extended or adjusted under 35 U.S.C. 154(b) by 0 days.

(21) Appl. No.: 15/103,696

(22) PCT Filed: Dec. 12, 2014

(86) PCT No.: PCT/NL2014/050855
§ 371 (c)(1),
(2) Date: Jun. 10, 2016

(87) PCT Pub. No.: WO2015/088344
PCT Pub. Date: Jun. 18, 2015

(65) Prior Publication Data
US 2016/0317611 A1 Nov. 3, 2016

(30) Foreign Application Priority Data
Dec. 12, 2013 (EP) ..................................... 13196989

(51) Int. Cl.
*A61K 38/16* (2006.01)
*C07K 14/47* (2006.01)
*A01N 43/38* (2006.01)

(52) U.S. Cl.
CPC .............. *A61K 38/16* (2013.01); *A01N 43/38* (2013.01); *C07K 14/4723* (2013.01)

(58) Field of Classification Search
None
See application file for complete search history.

(56) References Cited

U.S. PATENT DOCUMENTS

| | | | |
|---|---|---|---|
| 9,562,085 B2* | 2/2017 | Nibbering | C07K 14/4723 |
| 2009/0155335 A1* | 6/2009 | O'Shaughnessey | A61L 15/46 424/423 |
| 2012/0005790 A1* | 1/2012 | Ladram | C07K 14/463 800/301 |

FOREIGN PATENT DOCUMENTS

RU 2392962 C2 6/2010

OTHER PUBLICATIONS

Hwang et al.: "Reduction of Helical Content by Insertion of a Disulfide Bond Leads to an Antimicrobial Peptide with Decreased Hemolytic Activity", ChemMedChem Communications, vol. 8, No. 1, Nov. 13, 2012 (Nov. 13, 2012), pp. 59-62.*
Nell et al.: "Development of novel LL-37 derived antimicrobial peptides with LPS and LTA neutralizing and antimicrobial activities for therapeutic application", Peptides, vol. 27, No. 4, Apr. 1, 2006 (Apr. 1, 2006), pp. 649-660.*
European Patent Office, International Search Report in International Patent Application No. PCT/NL2014/050855, dated Mar. 19, 2015, 4 pp.
European Patent Office, Written Opinion in International Patent Application No. PCT/NL2014/050855, dated Mar. 19, 2015, 5 pp.
European Patent Office, International Preliminary Report on Patentability in International Patent Application No. PCT/NL2014/050855, dated Nov. 11, 2015, 6 pp.
Bartlett et al., "Reduction in the bactericidal activity of selected cathelicidin peptides by bovine calf serum or exogenous endotoxin," *International Journal of Antimicrobial Agents*, 23(6), Jun. 1, 2004, pp. 606-612.
Ciornei et al., "Antimicrobial and Chemoattractant Activity, Lipopolysaccharide Neutralization, Cytotoxicity, and Inhibition by Serum of Analogs of Human Cathelicidin LL-37," *Antimicrobial Agents and Chemotherapy*, 49(7), Jul. 1, 2005 pp. 2845-2850.
Hwang et al., "Reduction of Helical Content by Insertion of a Disulfide Bond Leads to an Antimicrobial Peptide with Decreased Hemolytic Activity," *ChemMedChem Communications*, 8(1), Nov. 13, 2012, pp. 59-62.
Nell et al., "Development of novel LL-37 derived antimicrobial peptides with LPS and LTA neutralizing and antimicrobial activities for therapeutic application," *Peptides*, 27(4), Apr. 1, 2006, pp. 649-660.
Federal Institute of Industrial Property, Office Action including search report in Russian Patent Application No. 2016123977/10(037533) (dated Apr. 25, 2018).
Frankel et al., "Characterization of diphtheria fusion proteins targeted to the human interleukin-3 receptor," *Protein Engineering*, 13(8): 575-581 (2000).

* cited by examiner

*Primary Examiner* — Maury A Audet
(74) *Attorney, Agent, or Firm* — Leydig, Voit and Mayer, Ltd.

(57) ABSTRACT

The invention relates to antimicrobial peptides, pharmaceutical compositions comprising the peptides and to uses thereof for in the treatment or prevention of microbial, bacterial, fungal, viral and parasitic infection.

16 Claims, 6 Drawing Sheets
Specification includes a Sequence Listing.

A

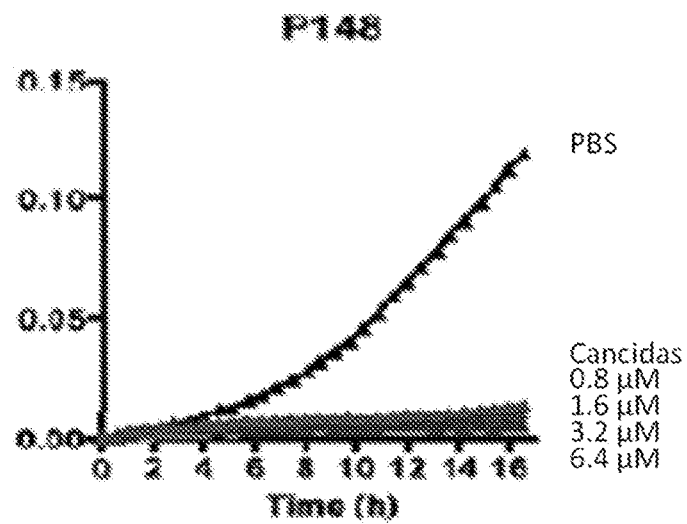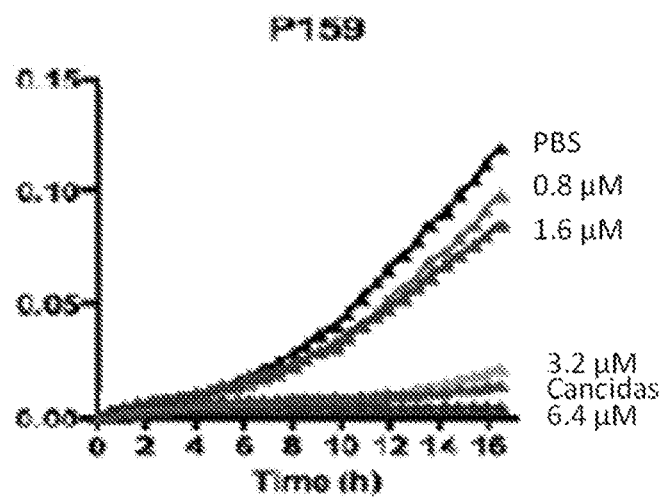
Figure 1, contnd

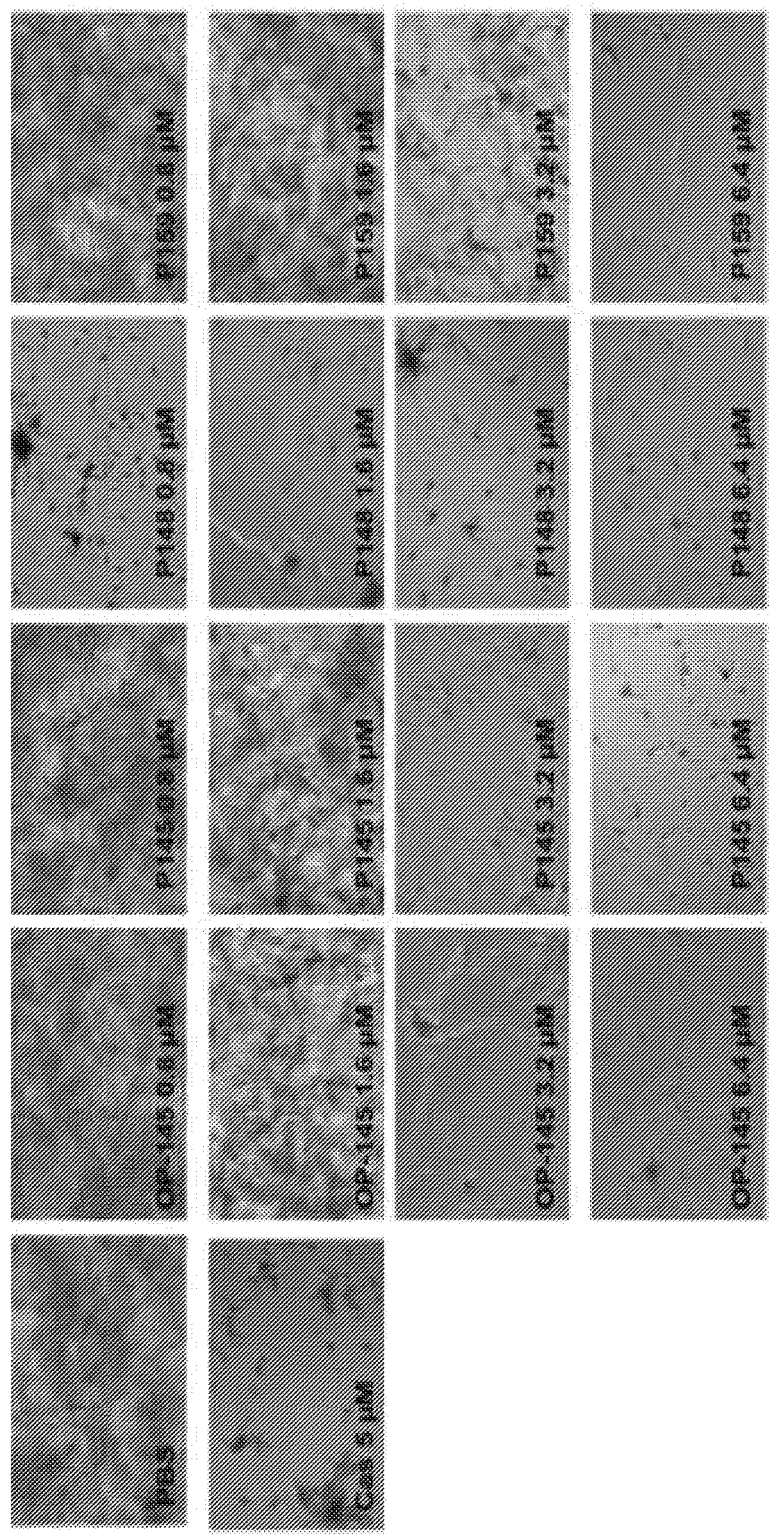
Figure 1, contnd

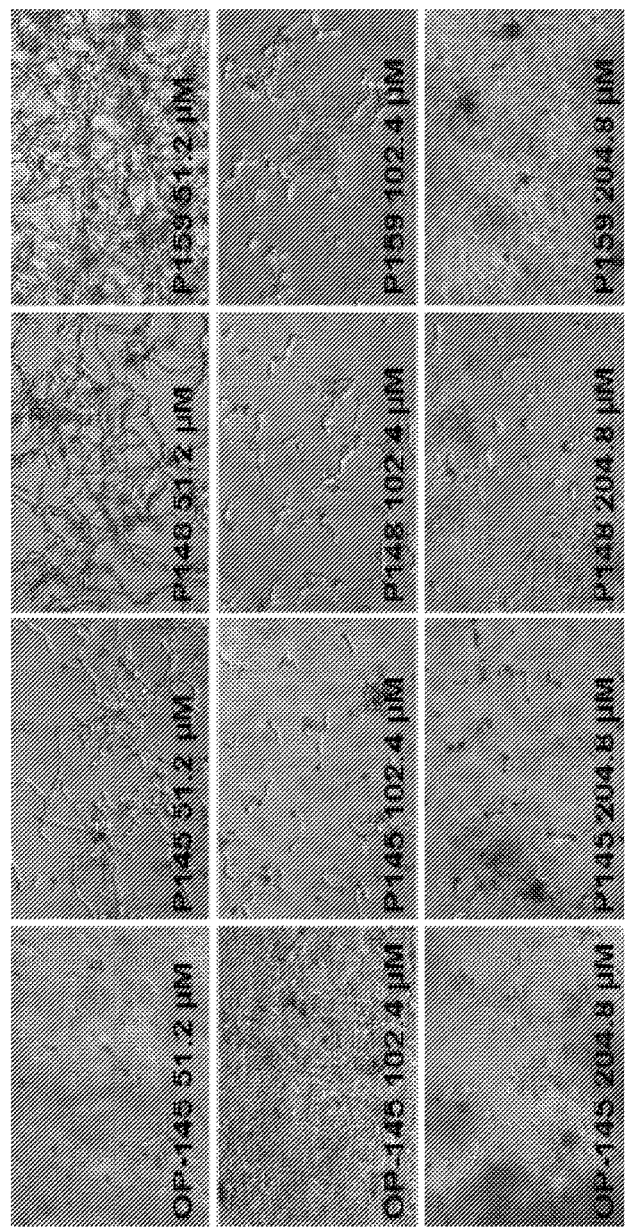
Figure 2, contnd

SEQUENCE LISTING

<160> NUMBER OF SEQ ID NOS: 165

<210> SEQ ID NO 1
<211> LENGTH: 24
<212> TYPE: PRT
<213> ORGANISM: Artificial Sequence
<220> FEATURE:
<223> OTHER INFORMATION: Synthetic antimicrobial protein

<400> SEQUENCE: 1

Leu Lys Lys Leu Tyr Lys Arg Leu Val Lys Ile Leu Lys Arg Trp Trp
1               5                   10                  15

Arg Tyr Leu Lys Arg Pro Val Arg
            20

<210> SEQ ID NO 2
<211> LENGTH: 24
<212> TYPE: PRT
<213> ORGANISM: Artificial Sequence
<220> FEATURE:
<223> OTHER INFORMATION: Synthetic antimicrobial peptide OP-145
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)

```
<223> OTHER INFORMATION: AMIDATION

<400> SEQUENCE: 2

Ile Gly Lys Glu Phe Lys Arg Ile Val Glu Arg Ile Lys Arg Phe Leu
1               5                   10                  15

Arg Glu Leu Val Arg Pro Leu Arg
            20

<210> SEQ ID NO 3
<211> LENGTH: 14
<212> TYPE: PRT
<213> ORGANISM: Artificial Sequence
<220> FEATURE:
<223> OTHER INFORMATION: Synthetic variant antimicrobial peptide

<400> SEQUENCE: 3

Lys Arg Leu Val Lys Ile Leu Lys Arg Trp Trp Arg Tyr Leu
1               5                   10

<210> SEQ ID NO 4
<211> LENGTH: 24
<212> TYPE: PRT
<213> ORGANISM: Artificial Sequence
<220> FEATURE:
<223> OTHER INFORMATION: Synthetic antimicrobial peptide P148

<400> SEQUENCE: 4

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 5
<211> LENGTH: 24
<212> TYPE: PRT
<213> ORGANISM: Artificial Sequence
<220> FEATURE:
<223> OTHER INFORMATION: Synthetic antimicrobial peptide P145

<400> SEQUENCE: 5

Leu Lys Arg Leu Tyr Lys Arg Leu Ala Lys Leu Ile Lys Arg Leu Tyr
1               5                   10                  15

Arg Tyr Leu Lys Lys Pro Val Arg
            20

<210> SEQ ID NO 6
<211> LENGTH: 22
<212> TYPE: PRT
<213> ORGANISM: Artificial Sequence
<220> FEATURE:
<223> OTHER INFORMATION: Synthetic variant antimicrobial peptide P148

<400> SEQUENCE: 6

Arg Val Trp Lys Arg Val Phe Lys Leu Leu Lys Arg Tyr Trp Arg Gln
1               5                   10                  15

Leu Lys Lys Pro Val Arg
            20

<210> SEQ ID NO 7
<211> LENGTH: 22
<212> TYPE: PRT
<213> ORGANISM: Artificial Sequence
<220> FEATURE:
<223> OTHER INFORMATION: Synthetic variant antimicrobial peptide P148
```

```
<400> SEQUENCE: 7

Leu Lys Arg Val Trp Lys Arg Val Phe Lys Leu Leu Lys Arg Tyr Trp
1               5                   10                  15

Arg Gln Leu Lys Lys Pro
            20

<210> SEQ ID NO 8
<211> LENGTH: 19
<212> TYPE: PRT
<213> ORGANISM: Artificial Sequence
<220> FEATURE:
<223> OTHER INFORMATION: Synthetic variant antimicrobial peptide P148

<400> SEQUENCE: 8

Arg Val Trp Lys Arg Val Phe Lys Leu Leu Lys Arg Tyr Trp Arg Gln
1               5                   10                  15

Leu Lys Lys

<210> SEQ ID NO 9
<211> LENGTH: 20
<212> TYPE: PRT
<213> ORGANISM: Artificial Sequence
<220> FEATURE:
<223> OTHER INFORMATION: Synthetic variant antimicrobial peptide P148

<400> SEQUENCE: 9

Trp Lys Arg Val Phe Lys Leu Leu Lys Arg Tyr Trp Arg Gln Leu Lys
1               5                   10                  15

Lys Pro Val Arg
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic variant antimicrobial peptide P148

<400> SEQUENCE: 10

Leu Lys Arg Val Trp Lys Arg Val Phe Lys Leu Leu Lys Arg Tyr Trp
1               5                   10                  15

Arg Gln Leu Lys
            20

<210> SEQ ID NO 11
<211> LENGTH: 18
<212> TYPE: PRT
<213> ORGANISM: Artificial Sequence
<220> FEATURE:
<223> OTHER INFORMATION: Synthetic variant antimicrobial peptide P148

<400> SEQUENCE: 11

Val Trp Lys Arg Val Phe Lys Leu Leu Lys Arg Tyr Trp Arg Gln Leu
1               5                   10                  15

Lys Lys

<210> SEQ ID NO 12
<211> LENGTH: 16
<212> TYPE: PRT
<213> ORGANISM: Artificial Sequence
<220> FEATURE:
<223> OTHER INFORMATION: Synthetic variant antimicrobial peptide P148

<400> SEQUENCE: 12
```

```
Trp Lys Arg Val Phe Lys Leu Leu Lys Arg Tyr Trp Arg Gln Leu Lys
1               5                   10                  15
```

<210> SEQ ID NO 13
<211> LENGTH: 14
<212> TYPE: PRT
<213> ORGANISM: Artificial Sequence
<220> FEATURE:
<223> OTHER INFORMATION: Synthetic variant antimicrobial peptide P148

<400> SEQUENCE: 13

```
Lys Arg Val Phe Lys Leu Leu Lys Arg Tyr Trp Arg Gln Leu
1               5                   10
```

<210> SEQ ID NO 14
<211> LENGTH: 24
<212> TYPE: PRT
<213> ORGANISM: Artificial Sequence
<220> FEATURE:
<223> OTHER INFORMATION: Synthetic antimicrobial peptide P159

<400> SEQUENCE: 14

```
Leu Lys Arg Leu Tyr Lys Arg Val Phe Arg Leu Leu Lys Arg Tyr Tyr
1               5                   10                  15

Arg Gln Leu Arg Arg Pro Val Arg
            20
```

<210> SEQ ID NO 15
<211> LENGTH: 24
<212> TYPE: PRT
<213> ORGANISM: Artificial Sequence
<220> FEATURE:
<223> OTHER INFORMATION: Synthetic retro-inverse P145

<400> SEQUENCE: 15

```
Arg Val Pro Lys Lys Leu Tyr Arg Tyr Leu Arg Lys Ile Leu Lys Ala
1               5                   10                  15

Leu Arg Lys Tyr Leu Arg Lys Leu
            20
```

<210> SEQ ID NO 16
<211> LENGTH: 24
<212> TYPE: PRT
<213> ORGANISM: Artificial Sequence
<220> FEATURE:
<223> OTHER INFORMATION: Synthetic retro-inverse P148

<400> SEQUENCE: 16

```
Arg Val Pro Lys Lys Leu Gln Arg Trp Tyr Arg Lys Leu Leu Lys Phe
1               5                   10                  15

Val Arg Lys Trp Val Arg Lys Leu
            20
```

<210> SEQ ID NO 17
<211> LENGTH: 24
<212> TYPE: PRT
<213> ORGANISM: Artificial Sequence
<220> FEATURE:
<223> OTHER INFORMATION: Synthetic retro-inverse P159

<400> SEQUENCE: 17

```
Arg Val Pro Arg Arg Leu Gln Arg Tyr Tyr Arg Lys Leu Leu Arg Phe
1               5                   10                  15

Val Arg Lys Tyr Leu Arg Lys Leu
```

```
<210> SEQ ID NO 18
<211> LENGTH: 24
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (2)..(2)
<223> OTHER INFORMATION: May be R
<220> FEATURE:
<221> NAME/KEY: VARIANT
<222> LOCATION: (3)..(3)
<223> OTHER INFORMATION: May be R
<220> FEATURE:
<221> NAME/KEY: VARIANT
<222> LOCATION: (4)..(4)
<223> OTHER INFORMATION: May be V
<220> FEATURE:
<221> NAME/KEY: VARIANT
<222> LOCATION: (5)..(5)
<223> OTHER INFORMATION: May be W
<220> FEATURE:
<221> NAME/KEY: VARIANT
<222> LOCATION: (8)..(8)
<223> OTHER INFORMATION: May be V
<220> FEATURE:
<221> NAME/KEY: VARIANT
<222> LOCATION: (9)..(9)
<223> OTHER INFORMATION: May be F or A
<220> FEATURE:
<221> NAME/KEY: VARIANT
<222> LOCATION: (10)..(10)
<223> OTHER INFORMATION: May be R
<220> FEATURE:
<221> NAME/KEY: VARIANT
<222> LOCATION: (11)..(11)
<223> OTHER INFORMATION: May be L
<220> FEATURE:
<221> NAME/KEY: VARIANT
<222> LOCATION: (12)..(12)
<223> OTHER INFORMATION: May be I or W
<220> FEATURE:
<221> NAME/KEY: VARIANT
<222> LOCATION: (15)..(15)
<223> OTHER INFORMATION: May be F, Y, L or I
<220> FEATURE:
<221> NAME/KEY: VARIANT
<222> LOCATION: (16)..(16)
<223> OTHER INFORMATION: May be F, Y, L or I
<220> FEATURE:
<221> NAME/KEY: VARIANT
<222> LOCATION: (18)..(18)
<223> OTHER INFORMATION: May be Q
<220> FEATURE:
<221> NAME/KEY: VARIANT
<222> LOCATION: (20)..(20)
<223> OTHER INFORMATION: May be R
<220> FEATURE:
<221> NAME/KEY: VARIANT
<222> LOCATION: (21)..(21)
<223> OTHER INFORMATION: May be K

<400> SEQUENCE: 18

Leu Lys Lys Leu Tyr Lys Arg Leu Val Lys Ile Leu Lys Arg Trp Trp
 1               5                  10                  15

Arg Tyr Leu Lys Arg Pro Val Arg
            20

<210> SEQ ID NO 19
<211> LENGTH: 24
<212> TYPE: PRT
<213> ORGANISM: Artificial Sequence
```

```
<220> FEATURE:
<223> OTHER INFORMATION: Synthetic antimicrobial peptide P139
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 19

Leu Lys Lys Leu Trp Lys Arg Val Phe Arg Ile Trp Lys Arg Ile Phe
1               5                   10                  15

Arg Tyr Leu Lys Arg Pro Val Arg
            20

<210> SEQ ID NO 20
<211> LENGTH: 24
<212> TYPE: PRT
<213> ORGANISM: Artificial Sequence
<220> FEATURE:
<223> OTHER INFORMATION: Synthetic antimicrobial peptide P140
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 20

Leu Arg Arg Leu Trp Lys Arg Leu Val Arg Ile Ile Lys Arg Ile Tyr
1               5                   10                  15

Arg Gln Leu Lys Arg Pro Val Arg
            20

<210> SEQ ID NO 21
<211> LENGTH: 24
<212> TYPE: PRT
<213> ORGANISM: Artificial Sequence
<220> FEATURE:
<223> OTHER INFORMATION: Synthetic antimicrobial peptide P141
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 21

Leu Arg Arg Leu Tyr Lys Arg Val Phe Arg Leu Leu Lys Arg Trp Trp
1               5                   10                  15

Arg Tyr Leu Lys Arg Pro Val Arg
            20

<210> SEQ ID NO 22
<211> LENGTH: 24
<212> TYPE: PRT
<213> ORGANISM: Artificial Sequence
<220> FEATURE:
<223> OTHER INFORMATION: Synthetic antimicrobial peptide P142
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (24)..(24)
<223> OTHER INFORMATION: AMIDATION

<400> SEQUENCE: 22

Leu Arg Arg Leu Trp Lys Arg Leu Val Lys Ile Leu Lys Arg Trp Phe
1               5                   10                  15

Arg Tyr Leu Arg Arg Pro Val Arg
            20

<210> SEQ ID NO 23
<211> LENGTH: 24
<212> TYPE: PRT
<213> ORGANISM: Artificial Sequence
<220> FEATURE:
<223> OTHER INFORMATION: Synthetic P143
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 23

Leu Arg Arg Leu Tyr Lys Arg Val Val Lys Leu Trp Lys Arg Leu Phe
1               5                   10                  15

Arg Gln Leu Arg Arg Pro Val Arg
            20

<210> SEQ ID NO 24
<211> LENGTH: 24
<212> TYPE: PRT
<213> ORGANISM: Artificial Sequence
<220> FEATURE:
<223> OTHER INFORMATION: Synthetic P144
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 24

Leu Lys Lys Leu Tyr Lys Arg Val Ala Lys Ile Trp Lys Arg Trp Ile
1               5                   10                  15

Arg Tyr Leu Lys Lys Pro Val Arg
            20

<210> SEQ ID NO 25
<211> LENGTH: 24
<212> TYPE: PRT
<213> ORGANISM: Artificial Sequence
<220> FEATURE:
<223> OTHER INFORMATION: Synthetic P146
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 25

Leu Lys Lys Leu Tyr Lys Arg Leu Phe Lys Ile Leu Lys Arg Ile Leu
```

```
1               5                   10                  15
Arg Tyr Leu Arg Lys Pro Val Arg
            20

<210> SEQ ID NO 26
<211> LENGTH: 24
<212> TYPE: PRT
<213> ORGANISM: Artificial Sequence
<220> FEATURE:
<223> OTHER INFORMATION: Synthetic P147
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 26

Leu Lys Lys Leu Trp Lys Arg Leu Ala Arg Leu Leu Lys Arg Phe Ile
1               5                   10                  15
Arg Gln Leu Arg Arg Pro Val Arg
            20

<210> SEQ ID NO 27
<211> LENGTH: 24
<212> TYPE: PRT
<213> ORGANISM: Artificial Sequence
<220> FEATURE:
<223> OTHER INFORMATION: Synthetic P149
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 27

Leu Lys Lys Val Tyr Lys Arg Leu Ala Arg Leu Leu Lys Arg Tyr Ile
1               5                   10                  15
Arg Tyr Leu Arg Arg Pro Val Arg
            20

<210> SEQ ID NO 28
<211> LENGTH: 24
<212> TYPE: PRT
<213> ORGANISM: Artificial Sequence
<220> FEATURE:
<223> OTHER INFORMATION: Synthetic p150
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 28

Leu Lys Lys Val Trp Lys Arg Val Ala Arg Leu Ile Lys Arg Trp Phe
1               5                   10                  15
Arg Tyr Leu Arg Arg Pro Val Arg
            20

<210> SEQ ID NO 29
```

```
<211> LENGTH: 24
<212> TYPE: PRT
<213> ORGANISM: Artificial Sequence
<220> FEATURE:
<223> OTHER INFORMATION: Synthetic P151
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 29

Leu Lys Lys Leu Tyr Lys Arg Leu Phe Lys Leu Trp Lys Arg Leu Tyr
1               5                   10                  15

Arg Tyr Leu Lys Lys Pro Val Arg
            20

<210> SEQ ID NO 30
<211> LENGTH: 24
<212> TYPE: PRT
<213> ORGANISM: Artificial Sequence
<220> FEATURE:
<223> OTHER INFORMATION: Synthetic P152
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 30

Leu Arg Arg Val Tyr Lys Arg Leu Ala Arg Leu Ile Lys Arg Tyr Leu
1               5                   10                  15

Arg Gln Leu Lys Lys Pro Val Arg
            20

<210> SEQ ID NO 31
<211> LENGTH: 24
<212> TYPE: PRT
<213> ORGANISM: Artificial Sequence
<220> FEATURE:
<223> OTHER INFORMATION: Synthetic P153
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 31

Leu Arg Lys Leu Trp Lys Arg Val Val Lys Ile Trp Lys Arg Tyr Leu
1               5                   10                  15

Arg Gln Leu Arg Arg Pro Val Arg
            20

<210> SEQ ID NO 32
<211> LENGTH: 24
<212> TYPE: PRT
<213> ORGANISM: Artificial Sequence
<220> FEATURE:
<223> OTHER INFORMATION: Synthetic P154
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 32

Leu Arg Lys Leu Trp Lys Arg Leu Ala Lys Ile Ile Lys Arg Leu Tyr
1               5                   10                  15

Arg Tyr Leu Arg Arg Pro Val Arg
            20

<210> SEQ ID NO 33
<211> LENGTH: 24
<212> TYPE: PRT
<213> ORGANISM: Artificial Sequence
<220> FEATURE:
<223> OTHER INFORMATION: Synthetic P145
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 33

Leu Lys Lys Val Tyr Lys Arg Val Ala Arg Leu Ile Lys Arg Leu Phe
1               5                   10                  15

Arg Tyr Leu Lys Arg Pro Val Arg
            20

<210> SEQ ID NO 34
<211> LENGTH: 24
<212> TYPE: PRT
<213> ORGANISM: Artificial Sequence
<220> FEATURE:
<223> OTHER INFORMATION: Synthetic P-156
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 34

Leu Arg Arg Leu Trp Lys Arg Leu Val Lys Leu Trp Lys Arg Phe Phe
1               5                   10                  15

Arg Tyr Leu Lys Lys Pro Val Arg
            20

<210> SEQ ID NO 35
<211> LENGTH: 24
<212> TYPE: PRT
<213> ORGANISM: Artificial Sequence
<220> FEATURE:
<223> OTHER INFORMATION: Synthetic P157
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION
```

```
<400> SEQUENCE: 35

Leu Lys Lys Val Trp Lys Arg Val Phe Arg Ile Leu Lys Arg Phe Leu
1               5                   10                  15

Arg Tyr Leu Lys Arg Pro Val Arg
            20

<210> SEQ ID NO 36
<211> LENGTH: 24
<212> TYPE: PRT
<213> ORGANISM: Artificial Sequence
<220> FEATURE:
<223> OTHER INFORMATION: Synthetic P158
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 36

Leu Arg Arg Val Tyr Lys Arg Leu Phe Arg Leu Trp Lys Arg Ile Ile
1               5                   10                  15

Arg Gln Leu Arg Arg Pro Val Arg
            20

<210> SEQ ID NO 37
<211> LENGTH: 24
<212> TYPE: PRT
<213> ORGANISM: Artificial Sequence
<220> FEATURE:
<223> OTHER INFORMATION: Synthetic P160
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 37

Leu Lys Lys Leu Trp Lys Arg Leu Ala Arg Leu Trp Lys Arg Ile Ile
1               5                   10                  15

Arg Gln Leu Lys Lys Pro Val Arg
            20

<210> SEQ ID NO 38
<211> LENGTH: 24
<212> TYPE: PRT
<213> ORGANISM: Artificial Sequence
<220> FEATURE:
<223> OTHER INFORMATION: Synthetic P161
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 38

Leu Arg Arg Val Trp Lys Arg Val Ala Arg Ile Ile Lys Arg Leu Tyr
1               5                   10                  15

Arg Tyr Leu Lys Arg Pro Val Arg
            20
```

```
<210> SEQ ID NO 39
<211> LENGTH: 24
<212> TYPE: PRT
<213> ORGANISM: Artificial Sequence
<220> FEATURE:
<223> OTHER INFORMATION: Synthetic P162
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 39

Leu Lys Arg Leu Trp Lys Arg Leu Phe Lys Ile Leu Lys Arg Tyr Tyr
1               5                   10                  15

Arg Tyr Leu Arg Arg Pro Val Arg
            20

<210> SEQ ID NO 40
<211> LENGTH: 24
<212> TYPE: PRT
<213> ORGANISM: Artificial Sequence
<220> FEATURE:
<223> OTHER INFORMATION: Synthetic P163
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 40

Leu Arg Arg Leu Trp Lys Arg Val Phe Lys Ile Ile Lys Arg Leu Phe
1               5                   10                  15

Arg Gln Leu Lys Lys Pro Val Arg
            20

<210> SEQ ID NO 41
<211> LENGTH: 22
<212> TYPE: PRT
<213> ORGANISM: Artificial Sequence
<220> FEATURE:
<223> OTHER INFORMATION: Synthetic P325
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 41

Arg Val Trp Lys Arg Val Phe Lys Leu Leu Lys Arg Tyr Trp Arg Gln
1               5                   10                  15

Leu Lys Lys Pro Val Arg
            20

<210> SEQ ID NO 42
<211> LENGTH: 22
<212> TYPE: PRT
<213> ORGANISM: Artificial Sequence
<220> FEATURE:
```

-continued

<223> OTHER INFORMATION: Synthetic P326
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (22)..(22)
<223> OTHER INFORMATION: AMIDATION

<400> SEQUENCE: 42

Leu Lys Arg Val Trp Lys Arg Val Phe Lys Leu Leu Lys Arg Tyr Trp
1               5                   10                  15

Arg Gln Leu Lys Lys Pro
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic P327
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATION

<400> SEQUENCE: 43

Arg Val Trp Lys Arg Val Phe Lys Leu Leu Lys Arg Tyr Trp Arg Gln
1               5                   10                  15

Leu Lys Lys Pro
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic P328
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: AMIDATION

<400> SEQUENCE: 44

Trp Lys Arg Val Phe Lys Leu Leu Lys Arg Tyr Trp Arg Gln Leu Lys
1               5                   10                  15

Lys Pro Val Arg
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic P329
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES

```
<222> LOCATION: (20)..(20)
<223> OTHER INFORMATION: AMIDATION

<400> SEQUENCE: 45

Leu Lys Arg Val Trp Lys Arg Val Phe Lys Leu Leu Lys Arg Tyr Trp
1               5                   10                  15
Arg Gln Leu Lys
            20

<210> SEQ ID NO 46
<211> LENGTH: 18
<212> TYPE: PRT
<213> ORGANISM: Artificial Sequence
<220> FEATURE:
<223> OTHER INFORMATION: Synthetic P330
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (18)..(18)
<223> OTHER INFORMATION: AMIDATION

<400> SEQUENCE: 46

Val Trp Lys Arg Val Phe Lys Leu Leu Lys Arg Tyr Trp Arg Gln Leu
1               5                   10                  15
Lys Lys

<210> SEQ ID NO 47
<211> LENGTH: 16
<212> TYPE: PRT
<213> ORGANISM: Artificial Sequence
<220> FEATURE:
<223> OTHER INFORMATION: Synthetic P331
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 47

Trp Lys Arg Val Phe Lys Leu Leu Lys Arg Tyr Trp Arg Gln Leu Lys
1               5                   10                  15

<210> SEQ ID NO 48
<211> LENGTH: 14
<212> TYPE: PRT
<213> ORGANISM: Artificial Sequence
<220> FEATURE:
<223> OTHER INFORMATION: Synthetic P332
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: AMIDATION

<400> SEQUENCE: 48

Lys Arg Val Phe Lys Leu Leu Lys Arg Tyr Trp Arg Gln Leu
1               5                   10

<210> SEQ ID NO 49
<211> LENGTH: 24
```

<212> TYPE: PRT
<213> ORGANISM: Artificial Sequence
<220> FEATURE:
<223> OTHER INFORMATION: Synthetic P145

<400> SEQUENCE: 49

Leu Lys Arg Leu Tyr Lys Arg Leu Ala Lys Leu Ile Lys Arg Leu Tyr
1               5                   10                  15

Arg Tyr Leu Lys Lys Pro Val Arg
            20

<210> SEQ ID NO 50
<211> LENGTH: 24
<212> TYPE: PRT
<213> ORGANISM: Artificial Sequence
<220> FEATURE:
<223> OTHER INFORMATION: Synthetic P246
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 50

Ala Lys Arg Leu Tyr Lys Arg Leu Ala Lys Leu Ile Lys Arg Leu Tyr
1               5                   10                  15

Arg Tyr Leu Lys Lys Pro Val Arg
            20

<210> SEQ ID NO 51
<211> LENGTH: 24
<212> TYPE: PRT
<213> ORGANISM: Artificial Sequence
<220> FEATURE:
<223> OTHER INFORMATION: Synthetic P247
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 51

Leu Ala Arg Leu Tyr Lys Arg Leu Ala Lys Leu Ile Lys Arg Leu Tyr
1               5                   10                  15

Arg Tyr Leu Lys Lys Pro Val Arg
            20

<210> SEQ ID NO 52
<211> LENGTH: 24
<212> TYPE: PRT
<213> ORGANISM: Artificial Sequence
<220> FEATURE:
<223> OTHER INFORMATION: Synthetic P248
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 52

Leu Lys Ala Leu Tyr Lys Arg Leu Ala Lys Leu Ile Lys Arg Leu Tyr
1               5                   10                  15

Arg Tyr Leu Lys Lys Pro Val Arg
            20

<210> SEQ ID NO 53
<211> LENGTH: 24
<212> TYPE: PRT
<213> ORGANISM: Artificial Sequence
<220> FEATURE:
<223> OTHER INFORMATION: Synthetic P249
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 53

Leu Lys Arg Ala Tyr Lys Arg Leu Ala Lys Leu Ile Lys Arg Leu Tyr
1               5                   10                  15

Arg Tyr Leu Lys Lys Pro Val Arg
            20

<210> SEQ ID NO 54
<211> LENGTH: 24
<212> TYPE: PRT
<213> ORGANISM: Artificial Sequence
<220> FEATURE:
<223> OTHER INFORMATION: Synthetic P250
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 54

Leu Lys Arg Leu Ala Lys Arg Leu Ala Lys Leu Ile Lys Arg Leu Tyr
1               5                   10                  15

Arg Tyr Leu Lys Lys Pro Val Arg
            20

<210> SEQ ID NO 55
<211> LENGTH: 24
<212> TYPE: PRT
<213> ORGANISM: Artificial Sequence
<220> FEATURE:
<223> OTHER INFORMATION: Synthetic P251
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 55

Leu Lys Arg Leu Tyr Ala Arg Leu Ala Lys Leu Ile Lys Arg Leu Tyr
1               5                   10                  15

Arg Tyr Leu Lys Lys Pro Val Arg
            20

```
<210> SEQ ID NO 56
<211> LENGTH: 24
<212> TYPE: PRT
<213> ORGANISM: Artificial Sequence
<220> FEATURE:
<223> OTHER INFORMATION: Synthetic P252
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 56

Leu Lys Arg Leu Tyr Lys Ala Leu Ala Lys Leu Ile Lys Arg Leu Tyr
1               5                   10                  15

Arg Tyr Leu Lys Lys Pro Val Arg
            20

<210> SEQ ID NO 57
<211> LENGTH: 24
<212> TYPE: PRT
<213> ORGANISM: Artificial Sequence
<220> FEATURE:
<223> OTHER INFORMATION: Synthetic P253
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 57

Leu Lys Arg Leu Tyr Lys Arg Ala Ala Lys Leu Ile Lys Arg Leu Tyr
1               5                   10                  15

Arg Tyr Leu Lys Lys Pro Val Arg
            20

<210> SEQ ID NO 58
<211> LENGTH: 24
<212> TYPE: PRT
<213> ORGANISM: Artificial Sequence
<220> FEATURE:
<223> OTHER INFORMATION: Synthetic P254
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 58

Leu Lys Arg Leu Tyr Lys Arg Leu Tyr Lys Leu Ile Lys Arg Leu Tyr
1               5                   10                  15

Arg Tyr Leu Lys Lys Pro Val Arg
            20

<210> SEQ ID NO 59
<211> LENGTH: 24
<212> TYPE: PRT
<213> ORGANISM: Artificial Sequence
<220> FEATURE:
<223> OTHER INFORMATION: Synthetic P254
<220> FEATURE:
```

<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 59

Leu Lys Arg Leu Tyr Lys Arg Leu Ala Ala Leu Ile Lys Arg Leu Tyr
1               5                   10                  15

Arg Tyr Leu Lys Lys Pro Val Arg
            20

<210> SEQ ID NO 60
<211> LENGTH: 24
<212> TYPE: PRT
<213> ORGANISM: Artificial Sequence
<220> FEATURE:
<223> OTHER INFORMATION: Synthetic P256
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 60

Leu Lys Arg Leu Tyr Lys Arg Leu Ala Lys Ala Ile Lys Arg Leu Tyr
1               5                   10                  15

Arg Tyr Leu Lys Lys Pro Val Arg
            20

<210> SEQ ID NO 61
<211> LENGTH: 24
<212> TYPE: PRT
<213> ORGANISM: Artificial Sequence
<220> FEATURE:
<223> OTHER INFORMATION: Synthetic P256
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 61

Leu Lys Arg Leu Tyr Lys Arg Leu Ala Lys Leu Ala Lys Arg Leu Tyr
1               5                   10                  15

Arg Tyr Leu Lys Lys Pro Val Arg
            20

<210> SEQ ID NO 62
<211> LENGTH: 24
<212> TYPE: PRT
<213> ORGANISM: Artificial Sequence
<220> FEATURE:
<223> OTHER INFORMATION: Synthetic P258
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

```
<400> SEQUENCE: 62

Leu Lys Arg Leu Tyr Lys Arg Leu Ala Lys Leu Ile Ala Arg Leu Tyr
1               5                   10                  15

Arg Tyr Leu Lys Lys Pro Val Arg
            20

<210> SEQ ID NO 63
<211> LENGTH: 24
<212> TYPE: PRT
<213> ORGANISM: Artificial Sequence
<220> FEATURE:
<223> OTHER INFORMATION: Synthetic P259
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 63

Leu Lys Arg Leu Tyr Lys Arg Leu Ala Lys Leu Ile Lys Ala Leu Tyr
1               5                   10                  15

Arg Tyr Leu Lys Lys Pro Val Arg
            20

<210> SEQ ID NO 64
<211> LENGTH: 24
<212> TYPE: PRT
<213> ORGANISM: Artificial Sequence
<220> FEATURE:
<223> OTHER INFORMATION: Synthetic P260
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 64

Leu Lys Arg Leu Tyr Lys Arg Leu Ala Lys Leu Ile Lys Arg Ala Tyr
1               5                   10                  15

Arg Tyr Leu Lys Lys Pro Val Arg
            20

<210> SEQ ID NO 65
<211> LENGTH: 24
<212> TYPE: PRT
<213> ORGANISM: Artificial Sequence
<220> FEATURE:
<223> OTHER INFORMATION: Synthetic P261
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 65

Leu Lys Arg Leu Tyr Lys Arg Leu Ala Lys Leu Ile Lys Arg Leu Ala
1               5                   10                  15

Arg Tyr Leu Lys Lys Pro Val Arg
```

```
                    20

<210> SEQ ID NO 66
<211> LENGTH: 24
<212> TYPE: PRT
<213> ORGANISM: Artificial Sequence
<220> FEATURE:
<223> OTHER INFORMATION: Synthetic P262
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 66

Leu Lys Arg Leu Tyr Lys Arg Leu Ala Lys Leu Ile Lys Arg Leu Tyr
1               5                   10                  15

Ala Tyr Leu Lys Lys Pro Val Arg
            20

<210> SEQ ID NO 67
<211> LENGTH: 24
<212> TYPE: PRT
<213> ORGANISM: Artificial Sequence
<220> FEATURE:
<223> OTHER INFORMATION: Synthetic P263
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 67

Leu Lys Arg Leu Tyr Lys Arg Leu Ala Lys Leu Ile Lys Arg Leu Tyr
1               5                   10                  15

Arg Ala Leu Lys Lys Pro Val Arg
            20

<210> SEQ ID NO 68
<211> LENGTH: 24
<212> TYPE: PRT
<213> ORGANISM: Artificial Sequence
<220> FEATURE:
<223> OTHER INFORMATION: Synthetic P264
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 68

Leu Lys Arg Leu Tyr Lys Arg Leu Ala Lys Leu Ile Lys Arg Leu Tyr
1               5                   10                  15

Arg Tyr Ala Lys Lys Pro Val Arg
            20

<210> SEQ ID NO 69
<211> LENGTH: 24
<212> TYPE: PRT
<213> ORGANISM: Artificial Sequence
```

```
<220> FEATURE:
<223> OTHER INFORMATION: Synthetic P265
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 69

Leu Lys Arg Leu Tyr Lys Arg Leu Ala Lys Leu Ile Lys Arg Leu Tyr
1               5                   10                  15

Arg Tyr Leu Ala Lys Pro Val Arg
            20

<210> SEQ ID NO 70
<211> LENGTH: 24
<212> TYPE: PRT
<213> ORGANISM: Artificial Sequence
<220> FEATURE:
<223> OTHER INFORMATION: Synthetic P266
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 70

Leu Lys Arg Leu Tyr Lys Arg Leu Ala Lys Leu Ile Lys Arg Leu Tyr
1               5                   10                  15

Arg Tyr Leu Lys Ala Pro Val Arg
            20

<210> SEQ ID NO 71
<211> LENGTH: 24
<212> TYPE: PRT
<213> ORGANISM: Artificial Sequence
<220> FEATURE:
<223> OTHER INFORMATION: Synthetic P267
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 71

Leu Lys Arg Leu Tyr Lys Arg Leu Ala Lys Leu Ile Lys Arg Leu Tyr
1               5                   10                  15

Arg Tyr Leu Lys Lys Ala Val Arg
            20

<210> SEQ ID NO 72
<211> LENGTH: 24
<212> TYPE: PRT
<213> ORGANISM: Artificial Sequence
<220> FEATURE:
<223> OTHER INFORMATION: Synthetic P268
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (24)..(24)
<223> OTHER INFORMATION: AMIDATION

<400> SEQUENCE: 72

Leu Lys Arg Leu Tyr Lys Arg Leu Ala Lys Leu Ile Lys Arg Leu Tyr
1               5                   10                  15

Arg Tyr Leu Lys Lys Pro Ala Arg
            20

<210> SEQ ID NO 73
<211> LENGTH: 24
<212> TYPE: PRT
<213> ORGANISM: Artificial Sequence
<220> FEATURE:
<223> OTHER INFORMATION: Synthetic P269
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 73

Leu Lys Arg Leu Tyr Lys Arg Leu Ala Lys Leu Ile Lys Arg Leu Tyr
1               5                   10                  15

Arg Tyr Leu Lys Lys Pro Val Ala
            20

<210> SEQ ID NO 74
<211> LENGTH: 24
<212> TYPE: PRT
<213> ORGANISM: Artificial Sequence
<220> FEATURE:
<223> OTHER INFORMATION: Synthetic P148
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 74

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 75
<211> LENGTH: 24
<212> TYPE: PRT
<213> ORGANISM: Artificial Sequence
<220> FEATURE:
<223> OTHER INFORMATION: Synthetic P270
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 75

Ala Lys Arg Val Trp Lys Arg Val Phe Lys Leu Leu Lys Arg Tyr Trp
```

```
1               5                   10                  15
Arg Gln Leu Lys Lys Pro Val Arg
            20

<210> SEQ ID NO 76
<211> LENGTH: 24
<212> TYPE: PRT
<213> ORGANISM: Artificial Sequence
<220> FEATURE:
<223> OTHER INFORMATION: Synthetic P271
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 76

Leu Ala Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 77
<211> LENGTH: 24
<212> TYPE: PRT
<213> ORGANISM: Artificial Sequence
<220> FEATURE:
<223> OTHER INFORMATION: Synthetic P272
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 77

Leu Lys Ala Val Trp Lys Arg Val Phe Lys Leu Leu Lys Arg Tyr Trp
1               5                   10                  15

Arg Gln Leu Lys Lys Pro Val Arg
            20

<210> SEQ ID NO 78
<211> LENGTH: 24
<212> TYPE: PRT
<213> ORGANISM: Artificial Sequence
<220> FEATURE:
<223> OTHER INFORMATION: Synthetic P273
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 78

Leu Lys Arg Ala Trp Lys Arg Val Phe Lys Leu Leu Lys Arg Tyr Trp
1               5                   10                  15

Arg Gln Leu Lys Lys Pro Val Arg
            20

<210> SEQ ID NO 79
```

```
<211> LENGTH: 24
<212> TYPE: PRT
<213> ORGANISM: Artificial Sequence
<220> FEATURE:
<223> OTHER INFORMATION: Synthetic P274
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 79

Leu Lys Arg Val Ala Lys Arg Val Phe Lys Leu Leu Lys Arg Tyr Trp
1               5                   10                  15

Arg Gln Leu Lys Lys Pro Val Arg
            20

<210> SEQ ID NO 80
<211> LENGTH: 24
<212> TYPE: PRT
<213> ORGANISM: Artificial Sequence
<220> FEATURE:
<223> OTHER INFORMATION: Synthetic P275
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 80

Leu Lys Arg Val Trp Ala Arg Val Phe Lys Leu Leu Lys Arg Tyr Trp
1               5                   10                  15

Arg Gln Leu Lys Lys Pro Val Arg
            20

<210> SEQ ID NO 81
<211> LENGTH: 24
<212> TYPE: PRT
<213> ORGANISM: Artificial Sequence
<220> FEATURE:
<223> OTHER INFORMATION: Synthetic P276
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 81

Leu Lys Arg Val Trp Lys Ala Val Phe Lys Leu Leu Lys Arg Tyr Trp
1               5                   10                  15

Arg Gln Leu Lys Lys Pro Val Arg
            20

<210> SEQ ID NO 82
<211> LENGTH: 24
<212> TYPE: PRT
<213> ORGANISM: Artificial Sequence
<220> FEATURE:
<223> OTHER INFORMATION: Synthetic P277
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 82

Leu Lys Arg Val Trp Lys Arg Ala Phe Lys Leu Leu Lys Arg Tyr Trp
1               5                   10                  15

Arg Gln Leu Lys Lys Pro Val Arg
            20

<210> SEQ ID NO 83
<211> LENGTH: 24
<212> TYPE: PRT
<213> ORGANISM: Artificial Sequence
<220> FEATURE:
<223> OTHER INFORMATION: Synthetic P278
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 83

Leu Lys Arg Val Trp Lys Arg Val Ala Lys Leu Leu Lys Arg Tyr Trp
1               5                   10                  15

Arg Gln Leu Lys Lys Pro Val Arg
            20

<210> SEQ ID NO 84
<211> LENGTH: 24
<212> TYPE: PRT
<213> ORGANISM: Artificial Sequence
<220> FEATURE:
<223> OTHER INFORMATION: Synthetic P279
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 84

Leu Lys Arg Val Trp Lys Arg Val Phe Ala Leu Leu Lys Arg Tyr Trp
1               5                   10                  15

Arg Gln Leu Lys Lys Pro Val Arg
            20

<210> SEQ ID NO 85
<211> LENGTH: 24
<212> TYPE: PRT
<213> ORGANISM: Artificial Sequence
<220> FEATURE:
<223> OTHER INFORMATION: Synthetic P280
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION
```

```
<400> SEQUENCE: 85

Leu Lys Arg Val Trp Lys Arg Val Phe Lys Ala Leu Lys Arg Tyr Trp
1               5                   10                  15

Arg Gln Leu Lys Lys Pro Val Arg
            20

<210> SEQ ID NO 86
<211> LENGTH: 24
<212> TYPE: PRT
<213> ORGANISM: Artificial Sequence
<220> FEATURE:
<223> OTHER INFORMATION: Synthetic P281
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 86

Leu Lys Arg Val Trp Lys Arg Val Phe Lys Leu Ala Lys Arg Tyr Trp
1               5                   10                  15

Arg Gln Leu Lys Lys Pro Val Arg
            20

<210> SEQ ID NO 87
<211> LENGTH: 24
<212> TYPE: PRT
<213> ORGANISM: Artificial Sequence
<220> FEATURE:
<223> OTHER INFORMATION: Synthetic P282
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 87

Leu Lys Arg Val Trp Lys Arg Val Phe Lys Leu Leu Ala Arg Tyr Trp
1               5                   10                  15

Arg Gln Leu Lys Lys Pro Val Arg
            20

<210> SEQ ID NO 88
<211> LENGTH: 24
<212> TYPE: PRT
<213> ORGANISM: Artificial Sequence
<220> FEATURE:
<223> OTHER INFORMATION: Synthetic P283
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 88

Leu Lys Arg Val Trp Lys Arg Val Phe Lys Leu Leu Lys Ala Tyr Trp
1               5                   10                  15

Arg Gln Leu Lys Lys Pro Val Arg
            20
```

```
<210> SEQ ID NO 89
<211> LENGTH: 24
<212> TYPE: PRT
<213> ORGANISM: Artificial Sequence
<220> FEATURE:
<223> OTHER INFORMATION: Synthetic P284
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 89

Leu Lys Arg Val Trp Lys Arg Val Phe Lys Leu Leu Lys Arg Ala Trp
1               5                   10                  15

Arg Gln Leu Lys Lys Pro Val Arg
            20

<210> SEQ ID NO 90
<211> LENGTH: 24
<212> TYPE: PRT
<213> ORGANISM: Artificial Sequence
<220> FEATURE:
<223> OTHER INFORMATION: Synthetic P285
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 90

Leu Lys Arg Val Trp Lys Arg Val Phe Lys Leu Leu Lys Arg Tyr Ala
1               5                   10                  15

Arg Gln Leu Lys Lys Pro Val Arg
            20

<210> SEQ ID NO 91
<211> LENGTH: 24
<212> TYPE: PRT
<213> ORGANISM: Artificial Sequence
<220> FEATURE:
<223> OTHER INFORMATION: Synthetic P286
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 91

Leu Lys Arg Val Trp Lys Arg Val Phe Lys Leu Leu Lys Arg Tyr Trp
1               5                   10                  15

Ala Gln Leu Lys Lys Pro Val Arg
            20

<210> SEQ ID NO 92
<211> LENGTH: 24
<212> TYPE: PRT
<213> ORGANISM: Artificial Sequence
<220> FEATURE:
```

```
<223> OTHER INFORMATION: Synthetic P287
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 92

Leu Lys Arg Val Trp Lys Arg Val Phe Lys Leu Leu Lys Arg Tyr Trp
1               5                   10                  15

Arg Ala Leu Lys Lys Pro Val Arg
            20

<210> SEQ ID NO 93
<211> LENGTH: 24
<212> TYPE: PRT
<213> ORGANISM: Artificial Sequence
<220> FEATURE:
<223> OTHER INFORMATION: Synthetic P288
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 93

Leu Lys Arg Val Trp Lys Arg Val Phe Lys Leu Leu Lys Arg Tyr Trp
1               5                   10                  15

Arg Gln Ala Lys Lys Pro Val Arg
            20

<210> SEQ ID NO 94
<211> LENGTH: 24
<212> TYPE: PRT
<213> ORGANISM: Artificial Sequence
<220> FEATURE:
<223> OTHER INFORMATION: Synthetic P289
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 94

Leu Lys Arg Val Trp Lys Arg Val Phe Lys Leu Leu Lys Arg Tyr Trp
1               5                   10                  15

Arg Gln Leu Ala Lys Pro Val Arg
            20

<210> SEQ ID NO 95
<211> LENGTH: 24
<212> TYPE: PRT
<213> ORGANISM: Artificial Sequence
<220> FEATURE:
<223> OTHER INFORMATION: Synthetic P290
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
```

<222> LOCATION: (24)..(24)
<223> OTHER INFORMATION: AMIDATION

<400> SEQUENCE: 95

Leu Lys Arg Val Trp Lys Arg Val Phe Lys Leu Leu Lys Arg Tyr Trp
1               5                   10                  15

Arg Gln Leu Lys Ala Pro Val Arg
            20

<210> SEQ ID NO 96
<211> LENGTH: 24
<212> TYPE: PRT
<213> ORGANISM: Artificial Sequence
<220> FEATURE:
<223> OTHER INFORMATION: Synthetic P291
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 96

Leu Lys Arg Val Trp Lys Arg Val Phe Lys Leu Leu Lys Arg Tyr Trp
1               5                   10                  15

Arg Gln Leu Lys Lys Ala Val Arg
            20

<210> SEQ ID NO 97
<211> LENGTH: 24
<212> TYPE: PRT
<213> ORGANISM: Artificial Sequence
<220> FEATURE:
<223> OTHER INFORMATION: Synthetic P292
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 97

Leu Lys Arg Val Trp Lys Arg Val Phe Lys Leu Leu Lys Arg Tyr Trp
1               5                   10                  15

Arg Gln Leu Lys Lys Pro Ala Arg
            20

<210> SEQ ID NO 98
<211> LENGTH: 24
<212> TYPE: PRT
<213> ORGANISM: Artificial Sequence
<220> FEATURE:
<223> OTHER INFORMATION: Synthetic P293
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 98

Leu Lys Arg Val Trp Lys Arg Val Phe Lys Leu Leu Lys Arg Tyr Trp
1               5                   10                  15

Arg Gln Leu Lys Lys Pro Val Ala
            20

<210> SEQ ID NO 99
<211> LENGTH: 24
<212> TYPE: PRT
<213> ORGANISM: Artificial Sequence
<220> FEATURE:
<223> OTHER INFORMATION: Synthetic P159
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 99

Leu Lys Arg Leu Tyr Lys Arg Val Phe Arg Leu Leu Lys Arg Tyr Tyr
1               5                   10                  15

Arg Gln Leu Arg Arg Pro Val Arg
            20

<210> SEQ ID NO 100
<211> LENGTH: 24
<212> TYPE: PRT
<213> ORGANISM: Artificial Sequence
<220> FEATURE:
<223> OTHER INFORMATION: Synthetic P294
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 100

Ala Lys Arg Leu Tyr Lys Arg Val Phe Arg Leu Leu Lys Arg Tyr Tyr
1               5                   10                  15

Arg Gln Leu Arg Arg Pro Val Arg
            20

<210> SEQ ID NO 101
<211> LENGTH: 24
<212> TYPE: PRT
<213> ORGANISM: Artificial Sequence
<220> FEATURE:
<223> OTHER INFORMATION: Synthetic P295
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 101

Leu Ala Arg Leu Tyr Lys Arg Val Phe Arg Leu Leu Lys Arg Tyr Tyr
1               5                   10                  15

Arg Gln Leu Arg Arg Pro Val Arg
            20

<210> SEQ ID NO 102
<211> LENGTH: 24

<212> TYPE: PRT
<213> ORGANISM: Artificial Sequence
<220> FEATURE:
<223> OTHER INFORMATION: Synthetic P296
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 102

Leu Lys Ala Leu Tyr Lys Arg Val Phe Arg Leu Leu Lys Arg Tyr Tyr
1               5                   10                  15

Arg Gln Leu Arg Arg Pro Val Arg
            20

<210> SEQ ID NO 103
<211> LENGTH: 24
<212> TYPE: PRT
<213> ORGANISM: Artificial Sequence
<220> FEATURE:
<223> OTHER INFORMATION: Synthetic P297
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 103

Leu Lys Arg Ala Tyr Lys Arg Val Phe Arg Leu Leu Lys Arg Tyr Tyr
1               5                   10                  15

Arg Gln Leu Arg Arg Pro Val Arg
            20

<210> SEQ ID NO 104
<211> LENGTH: 24
<212> TYPE: PRT
<213> ORGANISM: Artificial Sequence
<220> FEATURE:
<223> OTHER INFORMATION: Synthetic P298
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 104

Leu Lys Arg Leu Ala Lys Arg Val Phe Arg Leu Leu Lys Arg Tyr Tyr
1               5                   10                  15

Arg Gln Leu Arg Arg Pro Val Arg
            20

<210> SEQ ID NO 105
<211> LENGTH: 24
<212> TYPE: PRT
<213> ORGANISM: Artificial Sequence
<220> FEATURE:
<223> OTHER INFORMATION: Synthetic P299
<220> FEATURE:
<221> NAME/KEY: MOD_RES
<222> LOCATION: (1)..(1)

```
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 105

Leu Lys Arg Leu Tyr Ala Arg Val Phe Arg Leu Leu Lys Arg Tyr Tyr
1               5                   10                  15

Arg Gln Leu Arg Arg Pro Val Arg
            20

<210> SEQ ID NO 106
<211> LENGTH: 24
<212> TYPE: PRT
<213> ORGANISM: Artificial Sequence
<220> FEATURE:
<223> OTHER INFORMATION: Synthetic P300
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 106

Leu Lys Arg Leu Tyr Lys Ala Val Phe Arg Leu Leu Lys Arg Tyr Tyr
1               5                   10                  15

Arg Gln Leu Arg Arg Pro Val Arg
            20

<210> SEQ ID NO 107
<211> LENGTH: 24
<212> TYPE: PRT
<213> ORGANISM: Artificial Sequence
<220> FEATURE:
<223> OTHER INFORMATION: Synthetic P301
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 107

Leu Lys Arg Leu Tyr Lys Arg Ala Phe Arg Leu Leu Lys Arg Tyr Tyr
1               5                   10                  15

Arg Gln Leu Arg Arg Pro Val Arg
            20

<210> SEQ ID NO 108
<211> LENGTH: 24
<212> TYPE: PRT
<213> ORGANISM: Artificial Sequence
<220> FEATURE:
<223> OTHER INFORMATION: Synthetic P302
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 108
```

Leu Lys Arg Leu Tyr Lys Arg Val Ala Arg Leu Leu Lys Arg Tyr Tyr
1               5                   10                  15

Arg Gln Leu Arg Arg Pro Val Arg
            20

<210> SEQ ID NO 109
<211> LENGTH: 24
<212> TYPE: PRT
<213> ORGANISM: Artificial Sequence
<220> FEATURE:
<223> OTHER INFORMATION: Synthetic P303
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 109

Leu Lys Arg Leu Tyr Lys Arg Val Phe Ala Leu Leu Lys Arg Tyr Tyr
1               5                   10                  15

Arg Gln Leu Arg Arg Pro Val Arg
            20

<210> SEQ ID NO 110
<211> LENGTH: 24
<212> TYPE: PRT
<213> ORGANISM: Artificial Sequence
<220> FEATURE:
<223> OTHER INFORMATION: Synthetic P304
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 110

Leu Lys Arg Leu Tyr Lys Arg Val Phe Arg Ala Leu Lys Arg Tyr Tyr
1               5                   10                  15

Arg Gln Leu Arg Arg Pro Val Arg
            20

<210> SEQ ID NO 111
<211> LENGTH: 24
<212> TYPE: PRT
<213> ORGANISM: Artificial Sequence
<220> FEATURE:
<223> OTHER INFORMATION: Synthetic P305
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 111

Leu Lys Arg Leu Tyr Lys Arg Val Phe Arg Leu Ala Lys Arg Tyr Tyr
1               5                   10                  15

Arg Gln Leu Arg Arg Pro Val Arg
            20

<210> SEQ ID NO 112
<211> LENGTH: 24
<212> TYPE: PRT
<213> ORGANISM: Artificial Sequence
<220> FEATURE:
<223> OTHER INFORMATION: Synthetic P306
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 112

Leu Lys Arg Leu Tyr Lys Arg Val Phe Arg Leu Leu Ala Arg Tyr Tyr
1               5                   10                  15

Arg Gln Leu Arg Arg Pro Val Arg
            20

<210> SEQ ID NO 113
<211> LENGTH: 24
<212> TYPE: PRT
<213> ORGANISM: Artificial Sequence
<220> FEATURE:
<223> OTHER INFORMATION: Synthetic P307
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 113

Leu Lys Arg Leu Tyr Lys Arg Val Phe Arg Leu Leu Lys Ala Tyr Tyr
1               5                   10                  15

Arg Gln Leu Arg Arg Pro Val Arg
            20

<210> SEQ ID NO 114
<211> LENGTH: 24
<212> TYPE: PRT
<213> ORGANISM: Artificial Sequence
<220> FEATURE:
<223> OTHER INFORMATION: Synthetic P308
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 114

Leu Lys Arg Leu Tyr Lys Arg Val Phe Arg Leu Leu Lys Arg Ala Tyr
1               5                   10                  15

Arg Gln Leu Arg Arg Pro Val Arg
            20

<210> SEQ ID NO 115
<211> LENGTH: 24
<212> TYPE: PRT
<213> ORGANISM: Artificial Sequence
<220> FEATURE:
<223> OTHER INFORMATION: Synthetic P309

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 115

Leu Lys Arg Leu Tyr Lys Arg Val Phe Arg Leu Leu Lys Arg Tyr Ala
1               5                   10                  15

Arg Gln Leu Arg Arg Pro Val Arg
            20

<210> SEQ ID NO 116
<211> LENGTH: 24
<212> TYPE: PRT
<213> ORGANISM: Artificial Sequence
<220> FEATURE:
<223> OTHER INFORMATION: Synthetic P310
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 116

Leu Lys Arg Leu Tyr Lys Arg Val Phe Arg Leu Leu Lys Arg Tyr Tyr
1               5                   10                  15

Ala Gln Leu Arg Arg Pro Val Arg
            20

<210> SEQ ID NO 117
<211> LENGTH: 24
<212> TYPE: PRT
<213> ORGANISM: Artificial Sequence
<220> FEATURE:
<223> OTHER INFORMATION: Synthetic P311
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 117

Leu Lys Arg Leu Tyr Lys Arg Val Phe Arg Leu Leu Lys Arg Tyr Tyr
1               5                   10                  15

Arg Ala Leu Arg Arg Pro Val Arg
            20

<210> SEQ ID NO 118
<211> LENGTH: 24
<212> TYPE: PRT
<213> ORGANISM: Artificial Sequence
<220> FEATURE:
<223> OTHER INFORMATION: Synthetic P312
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
```

```
<223> OTHER INFORMATION: AMIDATION

<400> SEQUENCE: 118

Leu Lys Arg Leu Tyr Lys Arg Val Phe Arg Leu Leu Lys Arg Tyr Tyr
1               5                   10                  15

Arg Gln Ala Arg Arg Pro Val Arg
            20

<210> SEQ ID NO 119
<211> LENGTH: 24
<212> TYPE: PRT
<213> ORGANISM: Artificial Sequence
<220> FEATURE:
<223> OTHER INFORMATION: Synthetic P313
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 119

Leu Lys Arg Leu Tyr Lys Arg Val Phe Arg Leu Leu Lys Arg Tyr Tyr
1               5                   10                  15

Arg Gln Leu Ala Arg Pro Val Arg
            20

<210> SEQ ID NO 120
<211> LENGTH: 24
<212> TYPE: PRT
<213> ORGANISM: Artificial Sequence
<220> FEATURE:
<223> OTHER INFORMATION: Synthetic P314
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 120

Leu Lys Arg Leu Tyr Lys Arg Val Phe Arg Leu Leu Lys Arg Tyr Tyr
1               5                   10                  15

Arg Gln Leu Arg Ala Pro Val Arg
            20

<210> SEQ ID NO 121
<211> LENGTH: 24
<212> TYPE: PRT
<213> ORGANISM: Artificial Sequence
<220> FEATURE:
<223> OTHER INFORMATION: Synthetic P315
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 121

Leu Lys Arg Leu Tyr Lys Arg Val Phe Arg Leu Leu Lys Arg Tyr Tyr
1               5                   10                  15
```

Arg Gln Leu Arg Arg Ala Val Arg
            20

<210> SEQ ID NO 122
<211> LENGTH: 24
<212> TYPE: PRT
<213> ORGANISM: Artificial Sequence
<220> FEATURE:
<223> OTHER INFORMATION: Synthetic P316
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 122

Leu Lys Arg Leu Tyr Lys Arg Val Phe Arg Leu Leu Lys Arg Tyr Tyr
1               5                   10                  15
Arg Gln Leu Arg Arg Pro Ala Arg
            20

<210> SEQ ID NO 123
<211> LENGTH: 24
<212> TYPE: PRT
<213> ORGANISM: Artificial Sequence
<220> FEATURE:
<223> OTHER INFORMATION: Synthetic P317
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 123

Leu Lys Arg Leu Tyr Lys Arg Val Phe Arg Leu Leu Lys Arg Tyr Tyr
1               5                   10                  15
Arg Gln Leu Arg Arg Pro Val Ala
            20

<210> SEQ ID NO 124
<211> LENGTH: 24
<212> TYPE: PRT
<213> ORGANISM: Artificial Sequence
<220> FEATURE:
<223> OTHER INFORMATION: Synthetic P148
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 124

Leu Lys Arg Val Trp Lys Arg Val Phe Lys Leu Leu Lys Arg Tyr Trp
1               5                   10                  15
Arg Gln Leu Lys Lys Pro Val Arg
            20

<210> SEQ ID NO 125
<211> LENGTH: 24
<212> TYPE: PRT

```
<213> ORGANISM: Artificial Sequence
<220> FEATURE:
<223> OTHER INFORMATION: Synthetic P318
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 125

Ala Lys Arg Val Trp Lys Ala Val Phe Lys Leu Leu Lys Arg Tyr Trp
1               5                   10                  15

Arg Gln Leu Lys Lys Pro Val Arg
            20

<210> SEQ ID NO 126
<211> LENGTH: 24
<212> TYPE: PRT
<213> ORGANISM: Artificial Sequence
<220> FEATURE:
<223> OTHER INFORMATION: Synthetic P319
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 126

Leu Lys Arg Ala Trp Lys Ala Val Phe Lys Leu Leu Lys Arg Tyr Trp
1               5                   10                  15

Arg Gln Leu Lys Lys Pro Val Arg
            20

<210> SEQ ID NO 127
<211> LENGTH: 24
<212> TYPE: PRT
<213> ORGANISM: Artificial Sequence
<220> FEATURE:
<223> OTHER INFORMATION: Synthetic P320
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 127

Leu Lys Arg Val Ala Lys Ala Val Phe Lys Leu Leu Lys Arg Tyr Trp
1               5                   10                  15

Arg Gln Leu Lys Lys Pro Val Arg
            20

<210> SEQ ID NO 128
<211> LENGTH: 24
<212> TYPE: PRT
<213> ORGANISM: Artificial Sequence
<220> FEATURE:
<223> OTHER INFORMATION: Synthetic P321
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (24)..(24)
<223> OTHER INFORMATION: AMIDATION

<400> SEQUENCE: 128

Leu Lys Arg Val Trp Lys Ala Ala Phe Lys Leu Leu Lys Arg Tyr Trp
1               5                   10                  15

Arg Gln Leu Lys Lys Pro Val Arg
            20

<210> SEQ ID NO 129
<211> LENGTH: 24
<212> TYPE: PRT
<213> ORGANISM: Artificial Sequence
<220> FEATURE:
<223> OTHER INFORMATION: Synthetic P322
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 129

Leu Lys Arg Val Trp Lys Ala Val Ala Lys Leu Leu Lys Arg Tyr Trp
1               5                   10                  15

Arg Gln Leu Lys Lys Pro Val Arg
            20

<210> SEQ ID NO 130
<211> LENGTH: 24
<212> TYPE: PRT
<213> ORGANISM: Artificial Sequence
<220> FEATURE:
<223> OTHER INFORMATION: Synthetic P323
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 130

Leu Lys Arg Val Trp Lys Ala Val Phe Lys Ala Leu Lys Arg Tyr Trp
1               5                   10                  15

Arg Gln Leu Lys Lys Pro Val Arg
            20

<210> SEQ ID NO 131
<211> LENGTH: 24
<212> TYPE: PRT
<213> ORGANISM: Artificial Sequence
<220> FEATURE:
<223> OTHER INFORMATION: Synthetic P324
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 131
```

```
Leu Lys Arg Val Trp Lys Ala Val Phe Lys Leu Ala Lys Arg Tyr Trp
1               5                   10                  15

Arg Gln Leu Lys Lys Pro Val Arg
            20
```

<210> SEQ ID NO 132
<211> LENGTH: 24
<212> TYPE: PRT
<213> ORGANISM: Artificial Sequence
<220> FEATURE:
<223> OTHER INFORMATION: Synthetic P148
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: AMIDATION

<400> SEQUENCE: 132

```
Leu Lys Arg Val Trp Lys Arg Val Phe Lys Leu Leu Lys Arg Tyr Trp
1               5                   10                  15

Arg Gln Leu Lys Lys Pro Val Arg
            20
```

<210> SEQ ID NO 133
<211> LENGTH: 24
<212> TYPE: PRT
<213> ORGANISM: Artificial Sequence
<220> FEATURE:
<223> OTHER INFORMATION: Synthetic P365
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (24)..(24)
<223> OTHER INFORMATION: AMIDATION

<400> SEQUENCE: 133

```
Leu Lys Arg Val Trp Lys Arg Val Phe Lys Leu Leu Lys Arg Tyr Trp
1               5                   10                  15

Arg Gln Leu Lys Lys Pro Val Arg
            20
```

<210> SEQ ID NO 134
<211> LENGTH: 24
<212> TYPE: PRT
<213> ORGANISM: Artificial Sequence
<220> FEATURE:
<223> OTHER INFORMATION: Synthetic P366
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (24)..(24)
<223> OTHER INFORMATION: AMIDATION

<400> SEQUENCE: 134

```
Leu Lys Arg Val Trp Lys Arg Val Phe Lys Leu Leu Lys Arg Tyr Trp
1               5                   10                  15

Arg Gln Leu Lys Lys Pro Val Arg
            20
```

<210> SEQ ID NO 135
<211> LENGTH: 24
<212> TYPE: PRT
<213> ORGANISM: Artificial Sequence
<220> FEATURE:
<223> OTHER INFORMATION: Synthetic P367
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (24)..(24)
<223> OTHER INFORMATION: AMIDATION

<400> SEQUENCE: 135

```
Leu Lys Arg Val Trp Lys Arg Val Phe Lys Leu Leu Lys Arg Tyr Trp
1               5                   10                  15

Arg Gln Leu Lys Lys Pro Val Arg
            20
```

<210> SEQ ID NO 136
<211> LENGTH: 24
<212> TYPE: PRT
<213> ORGANISM: Artificial Sequence
<220> FEATURE:
<223> OTHER INFORMATION: Synthetic P368
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (24)..(24)
<223> OTHER INFORMATION: AMIDATION

<400> SEQUENCE: 136

```
Leu Lys Arg Val Trp Lys Arg Val Phe Lys Leu Leu Lys Arg Tyr Trp
1               5                   10                  15

Arg Gln Leu Lys Lys Pro Val Arg
            20
```

<210> SEQ ID NO 137
<211> LENGTH: 24
<212> TYPE: PRT
<213> ORGANISM: Artificial Sequence
<220> FEATURE:
<223> OTHER INFORMATION: Synthetic P369
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: Orn
<220> FEATURE:

<221> NAME/KEY: MOD_RES
<222> LOCATION: (24)..(24)
<223> OTHER INFORMATION: AMIDATION

<400> SEQUENCE: 137

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 138
<211> LENGTH: 24
<212> TYPE: PRT
<213> ORGANISM: Artificial Sequence
<220> FEATURE:
<223> OTHER INFORMATION: Synthetic P370
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: Orn
<220> FEATURE:
<221> NAME/KEY: MOD_RES
<222> LOCATION: (24)..(24)
<223> OTHER INFORMATION: AMIDATION

<400> SEQUENCE: 138

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 139
<211> LENGTH: 24
<212> TYPE: PRT
<213> ORGANISM: Artificial Sequence
<220> FEATURE:
<223> OTHER INFORMATION: Synthetic P371
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: Orn
<220> FEATURE:
<221> NAME/KEY: MOD_RES
<222> LOCATION: (24)..(24)
<223> OTHER INFORMATION: AMIDATION

<400> SEQUENCE: 139

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 140
<211> LENGTH: 24
<212> TYPE: PRT
<213> ORGANISM: Artificial Sequence
<220> FEATURE:
<223> OTHER INFORMATION: Synthetic P372
<220> FEATURE:
<221> NAME/KEY: MOD_RES
<222> LOCATION: (1)..(1)
<223> OTHER INFORMATION: ACETYLATION

```
<220> FEATURE:
<221> NAME/KEY: MOD_RES
<222> LOCATION: (17)..(17)
<223> OTHER INFORMATION: Orn
<220> FEATURE:
<221> NAME/KEY: MOD_RES
<222> LOCATION: (24)..(24)
<223> OTHER INFORMATION: AMIDATION

<400> SEQUENCE: 140

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 141
<211> LENGTH: 24
<212> TYPE: PRT
<213> ORGANISM: Artificial Sequence
<220> FEATURE:
<223> OTHER INFORMATION: Synthetic P373
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: Orn
<220> FEATURE:
<221> NAME/KEY: MOD_RES
<222> LOCATION: (24)..(24)
<223> OTHER INFORMATION: AMIDATION

<400> SEQUENCE: 141

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 142
<211> LENGTH: 24
<212> TYPE: PRT
<213> ORGANISM: Artificial Sequence
<220> FEATURE:
<223> OTHER INFORMATION: Synthetic P374
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (24)..(24)
<223> OTHER INFORMATION: AMIDATION

<400> SEQUENCE: 142

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 143
<211> LENGTH: 24
<212> TYPE: PRT
<213> ORGANISM: Artificial Sequence
<220> FEATURE:
```

```
<223> OTHER INFORMATION: Synthetic P375
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: Orn
<220> FEATURE:
<221> NAME/KEY: MOD_RES
<222> LOCATION: (24)..(24)
<223> OTHER INFORMATION: AMIDATION

<400> SEQUENCE: 143

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 144
<211> LENGTH: 24
<212> TYPE: PRT
<213> ORGANISM: Artificial Sequence
<220> FEATURE:
<223> OTHER INFORMATION: Synthetic P377
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Dbu
<220> FEATURE:
<221> NAME/KEY: MOD_RES
<222> LOCATION: (24)..(24)
<223> OTHER INFORMATION: AMIDATION

<400> SEQUENCE: 144

Leu Xaa Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 145
<211> LENGTH: 24
<212> TYPE: PRT
<213> ORGANISM: Artificial Sequence
<220> FEATURE:
<223> OTHER INFORMATION: Synthetic P378
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Dbu
<220> FEATURE:
<221> NAME/KEY: MOD_RES
<222> LOCATION: (24)..(24)
<223> OTHER INFORMATION: AMIDATION

<400> SEQUENCE: 145

Leu Lys Xaa Val Trp Lys Arg Val Phe Lys Leu Leu Lys Arg Tyr Trp
1               5                   10                  15

Arg Gln Leu Lys Lys Pro Val Arg
            20
```

-continued

```
<210> SEQ ID NO 146
<211> LENGTH: 24
<212> TYPE: PRT
<213> ORGANISM: Artificial Sequence
<220> FEATURE:
<223> OTHER INFORMATION: Synthetic P379
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: Dbu
<220> FEATURE:
<221> NAME/KEY: MOD_RES
<222> LOCATION: (24)..(24)

<400> SEQUENCE: 146

Leu Lys Arg Val Trp Xaa Arg Val Phe Lys Leu Leu Lys Arg Tyr Trp
1               5                   10                  15

Arg Gln Leu Lys Lys Pro Val Arg
            20

<210> SEQ ID NO 147
<211> LENGTH: 24
<212> TYPE: PRT
<213> ORGANISM: Artificial Sequence
<220> FEATURE:
<223> OTHER INFORMATION: Synthetic P380
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: Dbu
<220> FEATURE:
<221> NAME/KEY: MOD_RES
<222> LOCATION: (24)..(24)
<223> OTHER INFORMATION: AMIDATION

<400> SEQUENCE: 147

Leu Lys Arg Val Trp Lys Xaa Val Phe Lys Leu Leu Lys Arg Tyr Trp
1               5                   10                  15

Arg Gln Leu Lys Lys Pro Val Arg
            20

<210> SEQ ID NO 148
<211> LENGTH: 24
<212> TYPE: PRT
<213> ORGANISM: Artificial Sequence
<220> FEATURE:
<223> OTHER INFORMATION: Synthetic P381
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: Dbu
<220> FEATURE:
<221> NAME/KEY: MOD_RES
<222> LOCATION: (24)..(24)
<223> OTHER INFORMATION: AMIDATION

<400> SEQUENCE: 148

Leu Lys Arg Val Trp Lys Arg Val Phe Xaa Leu Leu Lys Arg Tyr Trp
1               5                   10                  15
```

Arg Gln Leu Lys Lys Pro Val Arg
            20

<210> SEQ ID NO 149
<211> LENGTH: 24
<212> TYPE: PRT
<213> ORGANISM: Artificial Sequence
<220> FEATURE:
<223> OTHER INFORMATION: Synthetic P382
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: Dbu
<220> FEATURE:
<221> NAME/KEY: MOD_RES
<222> LOCATION: (24)..(24)
<223> OTHER INFORMATION: AMIDATION

<400> SEQUENCE: 149

Leu Lys Arg Val Trp Lys Arg Val Phe Lys Leu Leu Xaa Arg Tyr Trp
1               5                   10                  15

Arg Gln Leu Lys Lys Pro Val Arg
            20

<210> SEQ ID NO 150
<211> LENGTH: 24
<212> TYPE: PRT
<213> ORGANISM: Artificial Sequence
<220> FEATURE:
<223> OTHER INFORMATION: Synthetic P383
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: Dbu
<220> FEATURE:
<221> NAME/KEY: MOD_RES
<222> LOCATION: (24)..(24)
<223> OTHER INFORMATION: AMIDATION

<400> SEQUENCE: 150

Leu Lys Arg Val Trp Lys Arg Val Phe Lys Leu Leu Lys Xaa Tyr Trp
1               5                   10                  15

Arg Gln Leu Lys Lys Pro Val Arg
            20

<210> SEQ ID NO 151
<211> LENGTH: 24
<212> TYPE: PRT
<213> ORGANISM: Artificial Sequence
<220> FEATURE:
<223> OTHER INFORMATION: Synthetic P384
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (17)..(17)
<223> OTHER INFORMATION: Dbu
<220> FEATURE:
<221> NAME/KEY: MOD_RES
<222> LOCATION: (24)..(24)
<223> OTHER INFORMATION: AMIDATION -continued

<400> SEQUENCE: 151

Leu Lys Arg Val Trp Lys Arg Val Phe Lys Leu Leu Lys Arg Tyr Trp
1               5                   10                  15

Xaa Gln Leu Lys Lys Pro Val Arg
            20

<210> SEQ ID NO 152
<211> LENGTH: 24
<212> TYPE: PRT
<213> ORGANISM: Artificial Sequence
<220> FEATURE:
<223> OTHER INFORMATION: Synthetic P385
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: Dbu
<220> FEATURE:
<221> NAME/KEY: MOD_RES
<222> LOCATION: (24)..(24)
<223> OTHER INFORMATION: AMIDATION

<400> SEQUENCE: 152

Leu Lys Arg Val Trp Lys Arg Val Phe Lys Leu Leu Lys Arg Tyr Trp
1               5                   10                  15

Arg Gln Leu Xaa Lys Pro Val Arg
            20

<210> SEQ ID NO 153
<211> LENGTH: 24
<212> TYPE: PRT
<213> ORGANISM: Artificial Sequence
<220> FEATURE:
<223> OTHER INFORMATION: Synthetic P386
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: Dbu
<220> FEATURE:
<221> NAME/KEY: MOD_RES
<222> LOCATION: (24)..(24)
<223> OTHER INFORMATION: AMIDATION

<400> SEQUENCE: 153

Leu Lys Arg Val Trp Lys Arg Val Phe Lys Leu Leu Lys Arg Tyr Trp
1               5                   10                  15

Arg Gln Leu Lys Xaa Pro Val Arg
            20

<210> SEQ ID NO 154
<211> LENGTH: 24
<212> TYPE: PRT
<213> ORGANISM: Artificial Sequence
<220> FEATURE:
<223> OTHER INFORMATION: Synthetic P387
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: Dbu

```
<220> FEATURE:
<221> NAME/KEY: MOD_RES
<222> LOCATION: (24)..(24)
<223> OTHER INFORMATION: AMIDATION

<400> SEQUENCE: 154

Leu Lys Arg Val Trp Lys Arg Val Phe Lys Leu Leu Lys Arg Tyr Trp
1               5                   10                  15

Arg Gln Leu Lys Lys Pro Val Xaa
            20

<210> SEQ ID NO 155
<211> LENGTH: 24
<212> TYPE: PRT
<213> ORGANISM: Artificial Sequence
<220> FEATURE:
<223> OTHER INFORMATION: Synthetic P389
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 155

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 156
<211> LENGTH: 24
<212> TYPE: PRT
<213> ORGANISM: Artificial Sequence
<220> FEATURE:
<223> OTHER INFORMATION: Synthetic P390
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 156

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 157
<211> LENGTH: 24
<212> TYPE: PRT
<213> ORGANISM: Artificial Sequence
<220> FEATURE:
<223> OTHER INFORMATION: Synthetic P391
<220> FEATURE:
<221> NAME/KEY: MOD_RES
<222> LOCATION: (1)..(1)
```

<223> OTHER INFORMATION: ACETYLATION
<220> FEATURE:
<221> NAME/KEY: MOD_RES
<222> LOCATION: (6)..(6)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 157

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 158
<211> LENGTH: 24
<212> TYPE: PRT
<213> ORGANISM: Artificial Sequence
<220> FEATURE:
<223> OTHER INFORMATION: Synthetic P392
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 158

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 159
<211> LENGTH: 24
<212> TYPE: PRT
<213> ORGANISM: Artificial Sequence
<220> FEATURE:
<223> OTHER INFORMATION: Synthetic P393
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 159

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 160
<211> LENGTH: 24
<212> TYPE: PRT
<213> ORGANISM: Artificial Sequence
<220> FEATURE:
<223> OTHER INFORMATION: Synthetic P394
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 160

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 161
<211> LENGTH: 24
<212> TYPE: PRT
<213> ORGANISM: Artificial Sequence
<220> FEATURE:
<223> OTHER INFORMATION: Synthetic P395
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 161

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 162
<211> LENGTH: 24
<212> TYPE: PRT
<213> ORGANISM: Artificial Sequence
<220> FEATURE:
<223> OTHER INFORMATION: Synthetic P396
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (17)..(17)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 162

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 163
<211> LENGTH: 24
<212> TYPE: PRT
<213> ORGANISM: Artificial Sequence
<220> FEATURE:
<223> OTHER INFORMATION: Synthetic P397
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 163

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 164
<211> LENGTH: 24
<212> TYPE: PRT
<213> ORGANISM: Artificial Sequence
<220> FEATURE:
<223> OTHER INFORMATION: Synthetic P398
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 164

Leu Lys Arg Val Trp Lys Arg Val Phe Lys Leu Leu Lys Arg Tyr Trp
1               5                   10                  15

Arg Gln Leu Lys Lys Pro Val Arg
            20

<210> SEQ ID NO 165
<211> LENGTH: 24
<212> TYPE: PRT
<213> ORGANISM: Artificial Sequence
<220> FEATURE:
<223> OTHER INFORMATION: Synthetic P399
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: Dpr
<220> FEATURE:
<221> NAME/KEY: MOD_RES
<222> LOCATION: (24)..(24)
<223> OTHER INFORMATION: AMIDATION

<400> SEQUENCE: 165

Leu Lys Arg Val Trp Lys Arg Val Phe Lys Leu Leu Lys Arg Tyr Trp

```
1               5              10             15
Arg Gln Leu Lys Lys Pro Val Arg
                20
```

ANTIMICROBIAL PEPTIDE AND USES THEREOF

CROSS-REFERENCE TO RELATED APPLICATIONS

This patent application is a national phase application of PCT/NL2014/050855, filed Dec. 12, 2014, which claims the benefit of European Patent Application No. 13196989.1, filed Dec. 12, 2013, the disclosures of which are incorporated herein by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 73,707 bytes ASCII (Text) file named "725677 ST25.txt," created Jun. 10, 2016.

The invention relates to the field of biochemistry and medicine. More specifically the invention relates to the field of antimicrobial peptides and to counteracting bacterial, viral, fungal and parasitic infections.

Antimicrobial Peptides (AMPs) are an essential component of the defense system of organisms throughout nature and offer protection from invading pathogens. They show potent antimicrobial activity against Gram-positive and Gram-negative bacteria, fungi, parasites and viruses. The smaller AMPs (usually about 15-40 amino acids) act largely by disrupting the structure or function of microbial cell membranes, they do not target single defined molecular structures. Therefore, as opposed to conventional antibiotics, they are effective regardless of the metabolic activity of bacteria. Human AMPs such as defensins and cathelicidin (LL-37) are present in leukocytes and secreted by various epithelia in skin and mucosal surfaces. In addition to their antimicrobial activity, AMPs are important effector molecules in inflammation, immune activation, and wound healing. AMPs are quite diverse in sequence and secondary structure, but share some common properties. They are usually cationic, amphipathic and exert their microbicidal effect by compromising the bacterial membrane integrity. Interaction of AMPs with the anionic membrane surface of the target microbes leads to membrane permeabilization, cell lysis and death. It is generally accepted that the cytoplasmic membrane is the main target of most AMPs, whereby accumulation of peptide in the membrane causes increased permeability and loss of barrier function resulting in leakage of cytoplasmic components and cell death.

Conventional antibiotics kill bacteria by binding to targets such as an epitope on the cell wall, or targets in bacterial protein and DNA or RNA synthesis. Pathogenic bacteria develop resistance more rapidly by modifying the antibiotics targets so that antibiotics are no longer capable of binding these targets. A major advantage of AMPs over conventional antibiotics is that resistance does not readily develop. One reason for this is that do not target single defined molecular structures (epitopes) like conventional antibiotics, but act on the cell membrane killing microorganisms. AMPs are particularly useful in counteracting so-called biofilm-associated infections (BAI), which are surface-attached cellular agglomerates of microorganisms, mostly bacteria but also fungi. Biofilms contributes significantly to bacterial resistance to conventional antibiotics. Biofilms are associated to various pathological conditions in humans such as cystic fibrosis, colonization of indwelling medical devices and dental plaque formation and wounds. Counteracting biofilm associated infection with conventional antibiotics is further insufficient for a number of reasons including stimulation of the release of pro-inflammatory microbial compounds, insufficient penetration of the biofilm and inactivation or degradation in the blood as result of the necessary systemic administration. Other advantages of AMPs over conventional bacteria include the rapid onset of killing, the fact that they are biodegradable, which alleviates the current concern about residual antibiotics in the environment, and have concomitant anti-inflammatory activity.

Of the potential pool of hundreds of natural and synthetic peptides, relatively few have proceeded into clinical trials. Examples are magainin peptide, omiganan, OP-145, novexatin and lytixar. Only two AMPs, daptomycin and DPK-060, are currently in clinical development. For OP-145, which is also called P60.4Ac (Peptides, 2006; 27:649-60), up to phase 2 clinical trials have been performed. OP-145 is a 24 amino acid peptide derived from the endogenous human cathelicidin antimicrobial peptide LL-37. OP-145 has been developed as an endotoxin-neutralizing antimicrobial peptide for the topical treatment of chronic otitis media. In addition to being an anti-microbial peptide, OP-145 neutralizes LPS.

The currently known AMPs, including OP-145, still have a few drawbacks. For instance, various bacteria, such as *P. aeruginosa, E. faecalis, Proteus mirabilis, Streptococcus pyogenes* and *S. aureus* all secrete proteases that degrade several antimicrobial peptides, such as the cathelicidin LL-37. Thus, protease resistant antimicrobial peptides are advantageous from a therapeutical standpoint. Furthermore, due to potential lytic effect as well as other properties of AMPs against bacterial but also mammalian membranes, one of the challenges in designing new peptides relies on developing AMPs with high specificity against microorganisms such as bacterial or fungal cells as compared to cellular membranes of the infected patient, i.e., a high therapeutic index (minimal hemolytic concentration/minimal antimicrobial activity; MHC/MEC). Another important disadvantage of known AMPs, including OP-145, is that its activity is strongly affected by the presence of plasma components. For instance, for OP-145 the LC99.9 (the lowest peptide concentration which kills ≥99.9% of bacteria) in PBS of 1.6 µM, whereas the LC99.9 in PBS/plasma (1:1) is about 200 µM. This is in particular a disadvantage for systemically administered AMPs.

Several mechanisms may be responsible for the significantly lower activity of AMPs in the presence of plasma like peptide inactivation by plasma components, such as enzymatic degradation or peptide non-availability due to non-specific binding to plasma components. AMPs that are resistant to plasma components are not only important as they are potential systemic therapeutic agent, but also for the treatment of for instance infected wounds and medical implant related infection and inflammation. In particular in deep tissue infections high proteolytic activity may be present, which may lead to an inactivation of AMPs that are not proteolytic resistant. Wound fluid from chronic wounds has an excess of proteases and implanted materials are rapidly covered by plasma components from the hosts fluids. Both chronic wounds and medical implants are often associated with microbial biofilms. In particular in treatment of biofilm associate infections antibiotics are mostly administered systemically and are therefore prone to be degraded enzymatically in the blood and surrounding tissues. Thus, due to the sensitivity to plasma components, applicability of many AMPs including OP-145 will be limited, for instance to topical applications. There is thus a clear need for alternative AMPs that are resistant to plasma components, particularly as potential systemic therapeutic agents and/or therapeutic agent effective against biofilms infections associated with for instance chronic wounds and medical implants.

It is an object of the present invention to provide novel potent antimicrobial peptides that overcome the shortcomings of conventional antibiotics and that have improved properties over known antimicrobial peptides, in particular because they are resistant to plasma components. It is a further object of the invention to provide antimicrobial peptides that are non-allergenic when introduced into mammals such as humans, that they have high specificity against pathogenic microorganisms and have a particularly high antimicrobial activity against pathogenic microorganisms in biofilm associated infections. The peptides and polypeptides of the invention exert potent, broad spectrum antimicrobial activities against both microorganisms in biofilms and microorganisms not organized in biofilms, have rapid antimicrobial activities and can be used as therapeutic, prophylactic or diagnostic agents. The peptides polypeptides of the invention are designed to overcome problems of limited duration of effectiveness and limited applicability because they retain their antimicrobial activity in blood, plasma and serum and in the presence of components therefrom.

The present inventors found that peptides P139-P163 that are based on the sequence LKKLYKRLVKILKRWWRYLKRPVR (SEQ ID NO:1), are highly effective against (drug-resistant) Gram-positive bacteria (e.g. *Staphylococcus aureus* and *Staphylococcus epidermidis*) and Gram-negative bacteria (e.g. *Pseudomonas aeruginosa*) as well as against fungi (*Candida albicans* and *Aspergillus niger*), see Tables 2-4 and 11, FIGS. 1 and 2. The peptides thus exert broad spectrum antimicrobial activity. All peptides are very potent as evidenced by their low IC99.9 values, which in PBS are comparable to that of OP-145. Importantly, all peptides were found to be more effective than OP-145 in the presence of plasma. Most of the peptides were even considerably more potent with up to 16-fold higher activity in the presence of plasma than OP-145 (Tables 2-4). As is demonstrated in Table 2, OP-145 has an IC99.9 in the presence of 50% plasma of 204.8 µM. P148 and P159 have an IC99.9 of 12.8 µM (16-fold increase) in the presence of plasma. P140, P141, P144, P145, P150, P151, P152, P153, P158, P160, P161, P162 and P163 have an IC99.9 of 25.6 µM (8-fold increase) in the presence of plasma. P139, P142, P143, P146, P147, P154, P156 and P157 have an IC99.9 of 51.2 µM (4-fold increase) and P149 and P155 have an IC99.9 of 102.4 µM (2-fold increase) in the presence of plasma.

P145, P148 and P159 were demonstrated to be effective against both mid-logarithmic and stationary phase bacterial cultures (see Tables 2-4). In addition, P145, P148 and P159 are able to inhibit *S. aureus* biofilm formation (see FIG. 3). Moreover, P145, P148 and P159 have demonstrable immunomodulatory activity as they neutralize endotoxin lipoteichoic acid (LTA) and lipopolysaccharides (LPS), thus reducing the proinflammatory response (Table 12).

It was further found that shorter P148 variants having at least 16 amino acids have an antimicrobial activity in PBS that is comparable to that of P148 (see Table 5). Importantly, antimicrobial activity in the presence of plasma is also retained in this shorter variants. A shorter variant of P148 having 14 amino acids has reduced antimicrobial activity as compared to P148, but is still 5-fold more potent than OP-145 in the presence of plasma.

Hence, a polypeptide according to the present invention has high antimicrobial activity against micro-organisms, both in the presence and absence of plasma, and either residing in biofilms or not, with optimal anti-inflammatory (microbial compound-neutralizing) activity as evidenced by LPS and LTA neutralizing activity.

The effect of the antimicrobial peptides of the invention on biofilm infections is threefold: they will prevent biofilm formation and disperse existing biofilms, kill bacteria, fungi or other microbes at and around the site of release, and orchestrate immune responses by neutralizing pro-inflammatory microbial endotoxins such as lipoteichoic acid (LTA), peptidoglycan (PG) and lipopolysaccharides (LPS) and activating macrophages to enhance their phagocytic and microbicidal activity. This immune control is necessary to prevent the tissue surrounding implants to become a novel niche for the pathogens.

Accordingly, the present invention provides an isolated or recombinant polypeptide comprising an amino acid sequence LKKLYKRLVKILKRWWRYLKRPVR (SEQ ID NO:1), or a variant of said amino acid sequence, said polypeptide having antimicrobial, antibacterial, antiviral, antifungal and/or antiparasitic activity and having an in vitro antimicrobial, antibacterial, antiviral, antifungal and/or antiparasitic activity against at least one microbial species in the presence of 50% plasma that is at least 1.3-fold higher than the activity of OP-145 when determined under the same conditions,
said variant sequence having at least 14 amino acids and optionally having:
    one or more of the following amino acid substitutions:
        substitution of one or more amino acids selected from the group of L, V, F, A, I, W, Y or Q by another amino acid selected from said group;
        substitution of R and/or K by a positively charged amino acid;
        one or more substitutions of an amino acid by a corresponding D-amino acid;
        one or more substitutions of an amino acid by a corresponding non-natural amino acid; and/or
        a retro-inverso sequence of at least 14 consecutive amino acids from said amino acid sequence.

Further provided is an isolated or recombinant polypeptide comprising an amino acid sequence LKKLYKRLVKILKRWWRYLKRPVR (SEQ ID NO:1), or a variant of said amino acid sequence, said polypeptide having antimicrobial, antibacterial, antiviral, antifungal and/or antiparasitic activity and having an in vitro antimicrobial, antibacterial, antiviral, antifungal and/or antiparasitic activity against at least one microbial species in the presence of 50% plasma that is at least 1.3-fold higher than the activity of OP-145 when determined under the same conditions,
said variant sequence having at least 14 amino acids and optionally having:
    one or more of the following amino acid substitutions:
        substitution of one or more amino acids selected from the group of L, V, F, A, I, W, Y or Q by another amino acid selected from said group;
        substitution of R and/or K by A or a positively charged amino acid;
        one or more substitutions of an amino acid by a corresponding D-amino acid;
        one or more substitutions of an amino acid by a corresponding non-natural amino acid; and/or
        a retro-inverso sequence of at least 14 consecutive amino acids from said amino acid sequence.

In amino acid sequences or variants thereof as defined herein amino acids are denoted by single-letter symbols. These single-letter symbols and three-letter symbols are well known to the person skilled in the art and have the following meaning. A (Ala) is alanine, C (Cys) is cysteine, D (Asp) is aspartic acid, E (Glu) is glutamic acid, F (Phe) is phenylalanine, G (Gly) is glycine, H (His) is histidine, I (Ile) is isoleucine, K (Lys) is lysine, L (Leu) is leucine, M (Met) is methionine, N (Asn) is asparagine, P (Pro) is proline, Q (Gln) is glutamine, R (Arg) is arginine, S (Ser) is serine, T (Thr) is threonine, V (Val) is valine, W (Trp) is tryptophan, Y (Tyr) is tyrosine. As used herein, a "positively charged amino acid" refers to an amino acid that has a positive charge at physiological pH, i.e. at a pH of 7.3-7.4.

A polypeptide of the invention has antimicrobial activity, preferably antibacterial, antiviral and/or antifungal activity, more preferably antibacterial and/or antifungal activity. Further, a polypeptide of the invention preferably has both antimicrobial and anti-inflammatory activity. The term "antimicrobial activity" of a polypeptide as used herein refers to counteracting growth or proliferation of at least one microbe, e.g. a bacterium, a virus and/or a fungus, and includes inhibition, reduction or prevention of growth or proliferation as well as killing of the microbe. A microbe is an organism that is microscopic, i.e. usually too small to be seen by the naked human eye. Microbes are very diverse, they include bacteria, viruses, fungi, archaea, protozoans and microscopic algae. Similarly, the term "antibacterial activity", "antiviral activity", "antifungal activity" and "antiparasitic activity" as used herein refers to counteracting growth or proliferation of, respectively, a bacterium, a virus, a fungus and a parasite, in general and includes inhibition, reduction or prevention of growth or proliferation as well as killing thereof. Antimicrobial activity is for instance expressed as the inhibitory concentration (IC) or lethal concentration (LC). The ICx or LCx as used herein refer to the lowest peptide concentration which kills at least x % of microbes after 2 hours. For instance, IC99.9 an LC99.9 refer to the lowest peptide concentration which kills ≥99.9% of microbes. Antimicrobial, antibacterial, antiviral, antifungal and antiparasitic activity can be measured by methods known in the art.

One of such methods is detailed in the Examples of this application and involves an in vitro assay for determination of antimicrobial activity. In this method microbes, e.g. bacteria or fungi, are incubated, for instance for 1-2 hour, with different concentrations of a polypeptide according to the invention, where after the microbe-polypeptide mixture is incubated in or on a suitable culture medium to establish the number of surviving and/or killed microbes as compared to a sample of microbes which have not been incubated with polypeptide which has further been processed in the same way.

Virus plaque assays may be used to assess the antiviral activity of a polypeptide of the invention. In short, a virus inoculum is exposed to the polypeptide prior to infection of a permissive cell monolayer. After a standard interval the virus titer in the cellular extracts is determined using multiple dilutions of these extracts by infecting fresh cell monolayers and quantifying their effects on the cell monolayer.

For assessment of antiparasitic activity, a polypeptide of the invention and a parasite are incubated for a standard time interval. Thereafter, the metabolic activity of the parasites may be analyzed directly, for instance by an MTT assay, or the parasites are transferred to mammalian cells and after incubation parasite multiplication in these cells is assessed by microscopy.

The term "anti-inflammatory activity" of a polypeptide as used herein refers to inhibiting, reducing or preventing an inflammatory response in a subject that has been infected by microbes, e.g. bacteria, viruses, fungi, and/or parasites. Anti-inflammatory activity of polypeptides of the invention is achieved by inhibiting, reducing or preventing the release of pro-inflammatory microbial compounds, such as lipoteichoic acid (LTA), peptidoglycan (PG) and/or lipopolysaccharides (LPS). Anti-inflammatory activity can be measured by methods known in the art. Examples of such method are a LPS neutralization assay and a LTA neutralization assay as described in the Examples of this application. In such method, a polypeptide of the invention is mixed with a fixed concentration of LPS or LTA, such as 500 ng/ml LPS or 2 mg/ml LTA, and incubated for 30 min. Thereafter, these mixtures were added to diluted fresh human whole blood and 20 hours thereafter the level of cytokines (e.g. 1L-8 for LTA and 1L-12p40 for LPS) in the blood sample are measured by ELISA.

Polypeptides of the invention are resistant to plasma, also referred to as blood plasma, preferably human plasma. "Plasma" or "blood plasma" as used herein has the common meaning use in the art. It refers to the fluid portion of blood from which red and white blood cells and platelets are removed, which portion includes proteins, hormones and other organic compounds and inorganic compounds such as electrolytes. "Resistance to plasma" as used herein is defined as having an in vitro antimicrobial, antibacterial, antiviral, antifungal and/or antiparasitic activity against at least one microbial species in the presence of 50% plasma, preferably human plasma, that is at least 1.3-fold higher than the activity of OP-145 when determined under the same conditions. Preferably said activity against at least one microbial species is at least 1.5-fold higher than the activity of OP-145, more preferably at least 2-fold, more preferably at least 4-fold, more preferably at least 5-fold the activity of OP-145. Particularly preferred polypeptides have an antimicrobial activity against at least one microbial species that is at least 16-fold higher in the presence of 50% plasma than the antimicrobial activity of OP-145.

With "in the presence of 50% plasma" is meant that the antimicrobial activity is measured when polypeptide or OP-145 is incubated with microbes in liquid such as PBS with addition of plasma, preferably human plasma, at a final concentration of 50%. With "the same reaction conditions" is meant that the conditions under which the antimicrobial, antibacterial, antiviral, antifungal and/or antiparasitic activity of a polypeptide of the invention is determined are the same as the conditions under which the antimicrobial, antibacterial, antiviral, antifungal and/or antiparasitic activity of OP-145 is determined. Such conditions include, but are not limited to, the buffer in which polypeptide and microbes are incubated, the identity of the microbial species, the concentration of microbes, incubation time and temperature and the source of plasma used.

OP-145 has the sequence JIGKEFKRIVERIKRFL-RELVRPLRB, whereby J is acetyl and B is amide. A skilled person is well capable of synthesizing OP-145 in order to be able to compare the antimicrobial activity of OP-145 with that of other peptides using commonly used solid-phase synthesis methods or recombinant techniques as described herein below in more detail. Further, acetylation and amidation are common techniques used in the art, the skilled person is therefor capable of acetylation of the N-terminus and amidation of the C-terminus of the peptide chain of OP-145.

As detailed herein, the in vitro antimicrobial, antibacterial, antiviral, antifungal and/or antiparasitic activity is preferably expressed as the IC99.9 or IC 50. "IC99.9" and "IC50" as used herein refer to the lowest peptide concentration which kills at least 99.9% or 50%, respectively, of microbes within a given period, for instance 2 hours. Preferably polypeptides of the invention have an in vitro IC99.9 against at least one microbial species in the presence of 50% plasma that is at most 75% of the IC99.9 of OP-145 when determined under the same conditions. The in vitro IC99.9 against at least one microbial species in the presence of 50% plasma of a polypeptide according to the invention is preferably at most 70% of the IC99.9 of OP-145 when determined under the same conditions, more preferably at most 60%, more preferably at most 50%, more preferably at most 40%, more preferably at most 30%, more preferably at most 20%, most preferably at most 10%. Particularly preferred polypeptides have an in vitro IC99.9 against at least one microbial species in the presence of 50% plasma that is at most 10% of the IC99.9 of OP-145 when determined under the same conditions.

Polypeptides of the invention preferably have an in vitro IC99.9 of at most 150 µM after 2 hours at 37° C. against at least one microbial species in the presence of 50% plasma. Said IC99.9 is preferably determined in accordance with a method for determining the antimicrobial activity as described herein in the Examples. Said method described in the Examples for determining antimicrobial activity of microbes not associated with biofilm involves the mixing of 50 microL of a solution of a polypeptide in PBS with addition of human plasma at a final concentration of 50% and 20 microL of bacterial suspension with $5 \times 10^6$ CFU per mL of PBS in a well. After incubation of this mixture for 2 hours at 37° C. under shaking conditions, a sample is used for assessment of the bacterial counts. The lowest peptide concentration at which there is 99.9% of bacteria killed, is called the inhibitory concentration (IC) 99.9. Bacterial counts can be determined by manual CFU counting. For determining antibacterial activity for instance $1 \times 10^6$ CFU/ml bacteria are used, for determining antifungal activity for instance $1 \times 10^5$ cells/ml are used.

For determination of antibiofilm activity, said method described in the Examples involves determination of the IC50 after incubation of the polypeptide for 24 hours incubation at 37° C. with $1 \times 10^8$ CFU/ml of *S. aureus* JAR060131 in biofilm-adjusted BM2 in 96-wells polypropylene plates coated with plasma by overnight incubation with 20% plasma at 4° C., removal of planktonic bacteria by four washes with PBS and staining of biofilms with crystal violet. After solubilization with ethanol, the optical density at 590 nm is determined as a measure of biofilm mass.

Polypeptides of the invention preferably have an in vitro IC99.9 of at most 100 µM in the presence of 50% plasma, more preferably at most 80 µM, more preferably at most 51.2 µM, more preferably at most 30 µM. Preferred polypeptides of the invention have an IC99.9 as defined herein of at most 25.6 µM. Particularly preferred are polypeptides that have an in vitro IC99.9 in the presence of 50% plasma against at least one microbial species of at most 12.8 µM.

Said at least one microbial species is for instance a bacterial species such as *S. aureus, S. epidermidis, P. aeruginosa*, a fungal species such as *C. albicans* and *A. niger*, a parasitic species such as *Plasmodium falciparum* and *Toxoplasma gondii*, or a virus species such as hepatitis A virus, hepatitis C virus, Influenza A virus, etc. Preferably, a polypeptide of the invention has an in vitro IC99.9 of at most 105 µM against at least one bacterial or fungal species in the presence of 50% plasma, preferably against *S. aureus, S. epidermidis, P. aeruginosa, C. albicans* and/*A. niger*, most preferably a polypeptide of the invention has an in vitro IC99.9 of at most 105 µM against at least *S. aureus*, most preferably *S. aureus* JAR described in Campoccia et al. (Int J Artif Organs. 2008 Sep.; 31(9):841-7) in the presence of 50% plasma. Preferred polypeptides of the invention have an IC99.9 as defined herein against *S. aureus* of at most 25.6 µM, more preferably of at most 12.8 µM.

A preferred variant sequence has at most one substitution of an amino acid by A. This can be any amino acid, e.g. an amino acid at any one of the amino acid positions 1 to 24. As demonstrated in Tables 6-8, polypeptides wherein one amino acid is substituted by alanine maintain at least part of their antimicrobial activity, while for some alanine-substituted polypeptides activity is even increased.

Also provided is an isolated or recombinant polypeptide comprising an amino acid sequence LKKLYKRLVKILKRWWRYLKRPVR (SEQ ID NO:1), or a variant of said amino acid sequence, said polypeptide having antimicrobial, antibacterial, antiviral, antifungal and/or antiparasitic activity and having an in vitro antimicrobial, antibacterial, antiviral, antifungal and/or antiparasitic activity in the presence of 50% plasma that is at least 1.3-fold higher than the activity of OP-145 when determined under the same conditions,
said variant having at least 14 amino acids and optionally having:
   one or more of the following amino acid substitutions:
      substitution of K by a positively charged amino acid, preferably by R, homolysine, homoarginine, ornithine, diaminobutyric acid and diaminopropionic acid;
      substitution of R by a positively charged amino acid, preferably by K, homolysine, homoarginine, ornithine, diaminobutyric acid and diaminopropionic acid;
      substitution of L by V, I or W;
      substitution of Y by W or Q;
      substitution of V by F or A;
      substitution of I by L;
      substitution of W by F, Y, L or I
   one or more substitutions of an amino acid by a corresponding D-amino acid;
   one or more substitutions of an amino acid by a corresponding non-natural amino acid; and/or
   a retro-inverso sequence of at least 14 consecutive amino acids from said amino acid sequence.

Also provided is an isolated or recombinant polypeptide comprising an amino acid sequence LKKLYKRLVKILKRWWRYLKRPVR (SEQ ID NO:1), or a variant of said amino acid sequence, said polypeptide having antimicrobial, antibacterial, antiviral, antifungal and/or antiparasitic activity and having an in vitro antimicrobial, antibacterial, antiviral, antifungal and/or antiparasitic activity in the presence of 50% plasma that is at least 1.3-fold higher than the activity of OP-145 when determined under the same conditions,
said variant having at least 14 amino acids and optionally having:
   one or more of the following amino acid substitutions:
      substitution of K by A or a positively charged amino acid, preferably by A, R, homolysine, homoarginine, ornithine, diaminobutyric acid and diaminopropionic acid;

substitution of R by A or a positively charged amino acid, preferably by A, K, homolysine, homoarginine, ornithine, diaminobutyric acid and diaminopropionic acid;
substitution of L by A, V, I or W;
substitution of Y by A, W or Q;
substitution of V by F or A;
substitution of I by A or L;
substitution of W by A, F, Y, L or I
one or more substitutions of an amino acid by a corresponding D-amino acid;
one or more substitutions of an amino acid by a corresponding non-natural amino acid; and/or
a retro-inverso sequence of at least 14 consecutive amino acids from said amino acid sequence.

Such preferred variant sequence further preferably has at most one substitution of an amino acid by A. This can be any amino acid, thus an amino acid at any one of the amino acid positions 1 to 24 can be substituted by A.

A variant of amino acid sequence LKKLYKRLVKILKRWWRYLKRPVR (SEQ ID NO:1) as used herein has a length of at least 14 amino acids and preferably one or more of the following amino acid substitutions:
substitution of K by a positively charged amino acid, preferably by R, homolysine, homoarginine, ornithine, diaminobutyric acid and diaminopropionic acid, more preferably by R;
substitution of R by a positively charged amino acid, preferably by K, homolysine, homoarginine, ornithine, diaminobutyric acid and diaminopropionic acid, more preferably by K;
substitution of L by V, I or W;
substitution of Y by W or Q;
substitution of V by F or A;
substitution of I by L;
substitution of W by F, Y, L or I
substitution of one or more amino acids by the corresponding D-amino acid
substitution of one or more amino acids by a corresponding non-natural amino acid. Preferably, said variant sequence has up to 14 of said substitutions, more preferably up to 10 of said substitutions, such as up to 9, up to 8, up to 7, up to 6, up to 5, up to 4, up to 3, up to 2 or 1 of said substitutions.

Preferably said variant sequence optionally has one or more of the following amino acid substitutions:
substitution of K at amino acid position 2 by R
substitution of K at amino acid position 3 by R
substitution of L at amino acid position 4 by V
substitution of Y at amino acid position 5 by W
substitution of L at amino acid position 8 by V
substitution of V at amino acid position 9 by F or A
substitution of K at amino acid position 10 by R
substitution of I at amino acid position 11 by L
substitution of L at amino acid position 12 by I or W
substitution of W at amino acid position 15 by F, Y, L or I
substitution of W at amino acid position 16 by F, Y, L or I
substitution of Y at amino acid position 18 by Q
substitution of K at amino acid position 20 by R
substitution of R at amino acid position 21 by K
substitution of one or more amino acids by a corresponding D-amino acid Herein, the numbering of amino acid positions is as follows:

$L_1K_2K_3L_4Y_5K_6R_7L_8V_9K_{10}I_{11}L_{12}K_{13}R_{14}W_{15}W_{16}R_{17}Y_{18}L_{19}K_{20}R_{21}P_{22}V_{23}R_{24}$. Said variant further preferably has optionally one or more, more preferably at most one, substitution of an amino acid by A. This can be any amino acid, thus an amino acid at any one of the amino acid positions 1 to 24 can be substituted by A.

Preferably, a variant sequence as defined herein has up to 15 of said amino acid substitutions, more preferably up to 10 of said amino acid substitutions, such as 0, 1, 2, 3, 4, 5, 6, 7, 8, 9 or 10 of said substitutions. Further, a variant sequence as defined herein preferably comprises at least an amino acid sequence KRLVKILKRWWRYL (SEQ ID NO:3), i.e. amino acids 6 to 19, optionally having one or more of said amino acid substitutions. Provided is therefore an isolated or recombinant polypeptide comprising an amino acid sequence LKKLYKRLVKILKRWWRYLKRPVR (SEQ ID NO:1), or comprising a variant of said amino acid sequence, said polypeptide having antimicrobial, antibacterial, antiviral, antifungal and/or antiparasitic activity and having an in vitro antimicrobial, antibacterial, antiviral, antifungal and/or antiparasitic activity against at least one microbial species in the presence of 50% plasma that is at least 1.3-fold higher than the activity of OP-145 when determined under the same conditions,
said variant sequence having at least an amino acid sequence KRLVKILKRWWRYL (SEQ ID NO:3) optionally having:
up to 10 of the following amino acid substitutions:
substitution of one or more amino acids selected from the group of L, V, F, A, I, W, Y or Q by another amino acid selected from said group;
substitution of R and/or K by A or a positively charged amino acid;
one or more substitutions of an amino acid by a corresponding D-amino acid;
one or more substitutions of an amino acid by a corresponding non-natural amino acid; and/or
a retro-inverso sequence of at least 14 consecutive amino acids from said amino acid sequence.

A variant sequence that has at least one of said amino acid substitutions is further preferred.

A preferred polypeptide according to the invention comprises an amino acid sequence of peptides P139, P140, P141, P142, P143, P144, P145, P146, P147, P148, P149, P150, P151, P152, P153, P154, P155, P156, P157, P158, P159, P160, P161, P162 or P163 as depicted in Table 1 because these peptides have high antimicrobial activity in PBS and have increased antimicrobial activity in the presence of plasma as compared to peptide OP-145. Preferably, said polypeptide comprises an amino acid sequence of peptides P139, P140, P141, P142, P145, P146, P147, P148, P150, P151, P152, P153, P154, P156, P157, P158, P159, P160, P161, P162 or P163 as depicted in Table 1 because these peptides have at least 4-fold increased activity in the presence of plasma as compared to OP-145. More preferably, said polypeptide comprises an amino acid sequence of peptides P140, P141, P145, P148, P150, P151, P152, P153, P158, P159, P160, P161, P162 or P163 as depicted in Table 1 because these peptides have at least 8-fold increased activity in the presence of plasma as compared to OP-145.

A particularly preferred polypeptide of the invention comprises amino acid sequence LKRLYKRLAKLIKRLYRYLKKPVR, which is the amino acid sequence of peptide P145, or a variant of said amino acid sequence, said variant sequence having at least 14 amino acids and optionally having one or more substitutions of an amino acid by a corresponding D-amino acid and/or by a corresponding non-natural amino acid and/or optionally having a retro-inverso sequence of at least 14 consecutive amino acids from said amino acid sequence, more preferably said polypeptides comprises at least amino acids 14-19 of amino acid sequence LKRLYKRLAKLIKRLYRYLKKPVR, most preferably said polypeptide comprises amino acid sequence LKRLYKRLAKLIKRLYRYLKKPVR. Such polypeptide is particularly preferred because peptide P145 has potent, broad spectrum antimicrobial activity, both in the presence and absence of serum, and anti-inflammatory properties.

Another particularly preferred polypeptide of the invention comprises amino acid sequence LKRVWKRVFKLLKRYWRQLKKPVR, which is the amino acid sequence of peptide P148, or a variant of said amino acid sequence, said variant sequence having at least 14 amino acids and optionally having one or more substitutions of an amino acid by a corresponding D-amino acid and/or by a corresponding non-natural amino acid and/or optionally having a retro-inverso sequence of at least 14 consecutive amino acids from said amino acid sequence, more preferably said polypeptides comprises at least amino acids 14-19 of amino acid sequence LKRVWKRVFKLLKRYWRQLKKPVR, most preferably said polypeptide comprises amino acid sequence LKRVWKRVFKLLKRYWRQLKKPVR, RVWKRVFKLLKRYWRQLKKPVR, LKRVWKRVFKLLKRYWRQLKKP, RVWKRVFKLLKRYWRQLKK, WKRVFKLLKRYWRQLKKPVR, LKRVWKRVFKLLKRYWRQLK, VWKRVFKLLKRYWRQLKK, WKRVFKLLKRYWRQLK, KRVFKLLKRYWRQL. These are the amino acid sequence of peptide P148, P325, P326, P327, P328, P329, P330, P331 and P332 Such polypeptide is particularly preferred because peptide P148 has potent, broad spectrum antimicrobial activity, both in the presence and absence of serum, and anti-inflammatory properties and peptides P325, P326, P327, P328, P329, P330, P331 and P332 retained activity of peptide P148.

Another particularly preferred polypeptide of the invention comprises amino acid sequence LKRLYKRVFRLLKRYYRQLRRPVR, which is the amino acid sequence of peptide P159, or a variant of said amino acid sequence, said variant sequence having at least 14 amino acids and optionally having one or more substitutions of an amino acid by a corresponding D-amino acid and/or by a corresponding non-natural amino acid and/or optionally having a retro-inverso sequence of at least 14 consecutive amino acids from said amino acid sequence, more preferably said polypeptides comprises at least amino acids 14-19 of amino acid sequence LKRLYKRVFRLLKRYYRQLRRPVR, most preferably said polypeptide comprises amino acid sequence LKRLYKRVFRLLKRYYRQLRRPVR. Such polypeptide is particularly preferred because peptide P159 has potent, broad spectrum antimicrobial activity, both in the presence and absence of serum, and anti-inflammatory properties.

A further preferred polypeptide according to the invention comprises an amino acid sequence of peptides P246, P247, P248, P249, P250, P251, P252, P253, P254, P255, P256, P257, P258, P259, P260, P261, P262, P263, P264, P265, P266, P267, P268, P269, P270, P271, P272, P273, P274, P275, P276, P277, P278, P279, P280, P281, P282, P283, P284, P285, P286, P287, P288, P289, P290, P291, P292, P293, P294, P295, P296, P297, P298, P299, P300, P301, P302, P303, P304, P305, P306, P307, P308, P309, P310, P311, P312, P313, P314, P315, P316 or P317 as depicted in Tables 6, 7 and 8 because these peptides have high antimicrobial activity in PBS and have increased antimicrobial activity in the presence of plasma as compared to peptide OP-145. Polypeptides having such amino acid sequence are variants of polypeptides P145, P148 or P159 wherein one amino acid is substituted by A. A particularly preferred polypeptides of the invention has the amino acid sequence of peptide P276, a variant of P148 wherein Rat position 7 is substituted by A.

A preferred polypeptide according to the invention has an amino acid sequence of a polypeptide selected from Table 1, 2, 5, 6, 7, 8, 9, and/or 10. A polypeptide according to the invention more preferably comprises amino acid sequence LKKLYKRLVKILKRWWRYLKRPVR (SEQ ID NO:1) or a variant thereof having an lethal concentration (LC) 99.9 in 50% plasma of at most 102.4 µM selected from tables 2 or 5-10. In one embodiment, a polypeptide having an LC 99.9 in 50% plasma of at most 51.2 µM selected from tables 2 or 5-10 is provided, more preferably of at most 51.2 µM.

Alternatively, or in addition to substitutions of an amino acid by another amino acid as described above, a variant of amino acid sequence LKKLYKRLVKILKRWWRYLKRPVR (SEQ ID NO:1) as defined herein may contain one or more substitutions of an L-amino acid by its corresponding D-amino acid or by the D-amino acid corresponding to an L-amino acid that is present in said amino acid sequence after one or more of the amino acid substitutions indicated above. Amino acids indicated herein by an upper case single-letter symbol, such as A for alanine, are those L-amino acids commonly found in naturally occurring proteins. "Corresponding D-amino acid" as used herein is defined as the D-amino acid counter part of an L-amino acid. For example, the corresponding D-amino acid of alanine (A) is D-alanine (a), the corresponding D-amino acid of arginine (R) is D-arginine (r), the corresponding D-amino acid of asparagine (N) is D-asparagine (n), etc. All L-amino acids of a variant sequence as defined herein can be substituted by their corresponding D-amino acids. Hence, provided is a polypeptide according to the invention comprising an amino acid sequence LKKLYKRLVKILKRWWRYLKRPVR (SEQ ID NO:1), or a variant of said amino acid sequence, said polypeptide having antimicrobial, antibacterial, antiviral, antifungal, antiparasitic and/or anti-inflammatory activity, said variant sequence having at least 14 amino acids and optionally having:
one or more of the following amino acid substitutions:
substitution of one or more amino acids selected from the group of L, V, F, A, I, W, Y or Q by another amino acid selected from said group or by a corresponding D-amino acid of amino acid L, V, F, A, I, W, Y or Q;
substitution of R by a positively charged amino acid, preferably by K, homolysine, homoarginine, ornithine, diaminobutyric acid and diaminopropionic acid, or by the corresponding D-amino acid of K or R;
substitution of K by a positively charged amino acid, preferably by R, homolysine, homoarginine, ornithine, diaminobutyric acid and diaminopropionic acid, or by the corresponding D-amino acid of R or K;
one or more substitutions of an amino acid by a corresponding D-amino acid.

Such variant sequence may further have substitution of one or more amino acids, preferably at most one amino acid, selected from K and R substituted by A, or by a corresponding D-amino acid. Preferably, said variant sequence optionally has one or more of the following amino acid substitutions:
substitution of K by R or by the corresponding D-amino acid of R;

substitution of R by K or by the corresponding D-amino acid of K;

substitution of L by V, I or W or by a corresponding D-amino acid of amino acid V, I or W;

substitution of Y by W or Q or by a corresponding D-amino acid of amino acid W or Q;

substitution of V by F or A or by a corresponding D-amino acid of amino acid F or A;

substitution of I by L or by the corresponding D-amino acid of L;

substitution of W by F, Y, L or I or by a corresponding D-amino acid of amino acid L F, Y, L or I;

one or more substitutions of an amino acid by a corresponding D-amino acid.

More preferably, said variant sequence optionally has one or more of the following amino acid substitutions substitution of K at amino acid position 2 by R or by the corresponding D-amino acid of R;

substitution of K at amino acid position 3 by R or by the corresponding D-amino acid of R;

substitution of L at amino acid position 4 by V or by the corresponding D-amino acid of V;

substitution of Y at amino acid position 5 by W or by the corresponding D-amino acid of W;

substitution of L at amino acid position 8 by V or by the corresponding D-amino acid of V;

substitution of V at amino acid position 9 by F or A or by a corresponding D-amino acid of amino acid F or A;

substitution of K at amino acid position 10 by R or by the corresponding D-amino acid of R;

substitution of I at amino acid position 11 by L or by the corresponding D-amino acid of L;

substitution of L at amino acid position 12 by I or W or by a corresponding D-amino acid of amino acid I or W;

substitution of W at amino acid position 15 by F, Y, L or I or by a corresponding D-amino acid of amino acid F, Y, L or I;

substitution of W at amino acid position 16 by F, Y, L or I or by a corresponding D-amino acid of amino acid F, Y, L or I;

substitution of Y at amino acid position 18 by Q or by the corresponding D-amino acid of Q;

substitution of K at amino acid position 20 by R or by the corresponding D-amino acid of R;

substitution of R at amino acid position 21 by K or by the corresponding D-amino acid of K;

substitution of an amino acid by a corresponding D-amino acid.

A variant of amino acid sequence LKKLYKRLVKILKRWWRYLKRPVR (SEQ ID NO:1) as defined herein may contain up to 24 substitutions of an L-amino acid by its corresponding D-amino acid. Hence, the variant sequence may consist entirely of D-amino acids. For instance, the variant sequence may contain 24, 23, 22, 21, 20, 19, 18, 17, 16, 15, 14, 13, 12, 11, 10, 9, 8, 7, 6 5, 4, 3, 2 or 1 substitutions of an L-amino acid by its corresponding D-amino acid. Preferably, said variant sequence having one or more substitutions of an L-amino acid by its corresponding D-amino acid comprises at least 14 amino acids of an amino acid sequence of peptides P139, P140, P141, P142, P143, P144, P145, P146, P147, P148, P149, P150, P151, P152, P153, P154, P155, P156, P157, P158, P159, P160, P161, P162 or P163 as depicted in Table 1. More preferably a polypeptides of the invention optionally comprising one or more substitutions of an L-amino acid by its corresponding D-amino acid comprises an amino acid sequence of peptide P1454, P148 or P159. In one embodiment, a variant sequence as defined herein contains one substitution of an amino acid by its corresponding D-amino acid. The position of the D-amino acid in the amino acid sequence is irrelevant. In another embodiment, the variant sequence contains substitution of all L-amino acids by their corresponding D-amino acid. A variant sequence as defined herein may further be the retro-inverso peptide of at least 14 consecutive amino acids of amino acid sequence LKKLYKRLVKILKRWWRYLKRPVR (SEQ ID NO:1) or of an amino acid sequence of one of peptides P139-163, preferably of P145, P148 or P159. Preferably said variant sequence is a retro-inverso peptide of the full length of said amino acid sequence, preferably of the amino acid sequence of one of peptides P139-163, more preferably of P145, P148 or P159. A retro-inverso peptide is a peptide consisting of D-amino acids in the reversed sequence of a reference amino acid sequence. For instance, a preferred variant sequence of the invention is the retro-inverso peptide of the amino acid sequence of P145, P148 or P159, i.e. having the sequence rvpkklyrylrkilkalrkylrkl, rvpkklqrwyrkllkfvrkwvrkl or rvprrlqryyrkllrfvrkylrkl, respectively, or at least 14 amino acids from one of said sequences.

A variant of amino acid sequence LKKLYKRLVKILKRWWRYLKRPVR (SEQ ID NO:1) as defined herein may comprise up to 5 substitutions of an amino acid by a non-natural amino acid, or of an amino acid that is present in said amino acid sequence after one or more of the amino acid substitutions indicated above by a non-natural amino acid. "Non-natural amino acids" as used herein refers to non-genetically encoded amino acids, irrespective of whether they appear in nature or not. Non-natural amino acids that can be present in a variant of an amino acid sequence as defined herein include: β-amino acids; p-acyl-L-phenylalanine; N-acetyl lysine; O-4-allyl-L-tyrosine; 2-aminoadipic acid; 3-aminoadipic acid; beta-alanine; 4-tert-butyl hydrogen 2-azidosuccinate; beta-aminopropionic acid; 2-aminobutyric acid; 4-aminobutyric acid; 2,4,-diamino butyric acid; 6-aminocaproic acid; 2-aminoheptanoic acid; 2-aminoisobutyric acid; 3-aminoisobutyric acid; 2-aminopimelic acid; p-aminophenylalanine; 2, 3-diaminobutyric acid; 2, 3-diamino propionic acid; 2, 2'-diaminopimelic acid; p-amino-L-phenylalanine; p-azido-L-phenylalanine; D-allylglycine; p-benzoyl-L-phenylalanine; 3-benzothienyl alanine p-bromophenylalanine; t-butylalanine; t-butylglycine; 4-chlorophenylalanine; cyclohexylalanine; cysteic acid; D-citrulline; thio-L-citrulline; desmosine; epsilon-amino hexanoic acid; N-ethylglycine; N-ethylasparagine; 2-fluorophenylalanine; 3-fluorophenylalanine; 4-fluorophenylalanine; homoarginine; homocysteine; homoserine; hydroxylysine; allo-hydroxylysine; 3-(3-methyl-4-nitrobenzyl)-L-histidine methyl ester; isodesmosine; allo-isoleucine; isopropyl-L-phenylalanine; 3-methylphenylalanine; N-methylglycine; N-methylisoleucine; 6-N-methyllysine; O-methyl-L-tyrosine; N-methylvaline; methionin sulfoxide; 2-napthylalanine; L-3-(2-naphthyl)alanine; isoserine; 3-phenylserine; norvaline; norleucine; 5,5,5-trifluoro-DL-leucine; ornithine; 3-chloro-tyrosine; N5-carbamoylornithine; penicillamine; phenylglycine; piperidinic acid; pyridylalanine; 1, 2, 3, 4-tetrahydro-isoquinoline-3-carboxylix acid; beta-2-thienylalanine; γ-carboxy-DL-glutamic acid; 4-fluoro-DL-glutamic acid; D-thyroxine; allo-threonine; 5-hydroxy-tryptophan; 5-methoxy-tryptophan; 5-fluoro-tryptophan; 3-fluoro-valine.

Preferably, a natural amino acid of said sequence is substituted by a corresponding non-natural amino acid. As used herein, a "corresponding non-natural amino acid" refers to a non-natural amino acid that is a derivative of the reference natural amino acid. For instance, a natural amino acid is substituted by the corresponding β-amino acid. β-amino acids have their amino group bonded to the β carbon rather than the α carbon as in the natural amino acids. For instance, α-alanine is substituted by β-alanine, etc. Other examples of substitution of a natural amino acid by a non-natural amino acid that is a derivative of said natural amino acid are the following. Alanine is for instance substituted by beta-alanine, t-butylalanine, 2-napthylalanine; L-3-(2-naphthyl)alanine, 2-aminoisobutyric acid. Arginine is for instance substituted by homoarginine, ornithine, N5-carbamoylornithine, 3-amino-propionic acid. Asparagine is for instance substituted by N-ethylasparagine. Aspartic acid is for instance substituted by 4-tert-butyl hydrogen 2-azidosuccinate. Cysteine is for instance substituted by cysteic acid, homocysteine. Glutamic acid is for instance substituted by γ-carboxy-DL-glutamic acid; 4-fluoro-DL-glutamic acid. Glutamine is for instance substituted by D-citrulline, thio-L-citrulline Glycine is for instance substituted by N-methylglycine, t-butylglycine, N-methylglycine, D-allylglycine. Histidine is for instance substituted by 3-(3-methyl-4-nitrobenzyl)-L-histidine methyl ester. Isoleucine is for instance substituted by isodesmosine, N-methylisoleucine, allo-isoleucine. Leucine is for instance substituted by norleucine, desmosine, 5,5,5-trifluoro-leucine. Lysine is for instance substituted by 6-N-methyllysine, 2-aminoheptanoic acid, N-acetyl lysine, hydroxylysine, allo-hydroxylysine. Methionine is for instance substituted by methionin sulfoxide. Phenylalanine is for instance substituted by p-amino-L-phenylalanine, 3-benzothienyl alanine p-bromophenylalanine, p-acyl-L-phenylalanine, 2-fluorophenylalanine, 3-fluorophenylalanine, 4-fluorophenylalanine. Proline is for instance substituted by 3-hydroxyproline, 4-hydroxyproline, 1-acetyl-4-hydroxy-L-proline. Serine is for instance substituted by homoserine, isoserine, 3-phenylserine. Threonine is for instance substituted by D-thyroxine, allo-threonine. Tryptophan is for instance substituted by 5-hydroxy-tryptophan, 5-methoxy-tryptophan, 5-fluoro-tryptophan. Tyrosine is for instance substituted by O-methyl-L-tyrosine, O-4-allyl-L-tyrosine, 3-chloro-tyrosine. Valine is for instance substituted by norvaline, N-methylvaline, 3-fluoro-valine.

Hence, provided is a polypeptide according to the invention comprising an amino acid sequence LKKLYKRLVKILKRWWRYLKRPVR (SEQ ID NO:1), or a variant of said amino acid sequence, said polypeptide having antimicrobial, antibacterial, antiviral, antifungal, antiparasitic and/or anti-inflammatory activity, said variant sequence having at least 14 amino acids and optionally having:
one or more of the following amino acid substitutions:
substitution of one or more amino acids selected from the group of L, V, F, A, I, W, Y or Q by another amino acid selected from said group or by a corresponding non-natural amino acid of amino acid L, V, F, A, I, W, Y or Q;
substitution of R by K or by a corresponding non-natural amino acid of K;
substitution of K by R or by a corresponding non-natural amino acid of K;
one or more substitutions of an amino acid by a corresponding D-amino acid.

Such variant sequence may further have substitution of one or more amino acids, preferably at most one amino acid, selected from K and R substituted by a corresponding non-natural amino acid A. Preferably, said variant sequence optionally has one or more of the following amino acid substitutions:
substitution of K by R or by a corresponding non-natural amino acid of R;
substitution of R by K or by a corresponding non-natural amino acid of K;
substitution of L by V, I or W or by a corresponding non-natural amino acid of amino acid V, I or W;
substitution of Y by W or Q or by a corresponding non-natural amino acid of amino acid W or Q;
substitution of V by F or A or by a corresponding non-natural amino acid of amino acid F or A;
substitution of I by L or by a corresponding non-natural amino acid of L;
substitution of W by F, Y, L or I or by a corresponding non-natural amino acid of amino acid L F, Y, L or I;
one or more substitutions of an amino acid by a corresponding non-natural amino acid.

More preferably, said variant sequence optionally has one or more of the following amino acid substitutions
substitution of K at amino acid position 2 by R or by a corresponding non-natural amino acid of R;
substitution of K at amino acid position 3 by R or by a corresponding non-natural amino acid of R;
substitution of L at amino acid position 4 by V or by a corresponding non-natural amino acid of V;
substitution of Y at amino acid position 5 by W or by a corresponding non-natural amino acid of W;
substitution of L at amino acid position 8 by V or by a corresponding non-natural amino acid of V;
substitution of V at amino acid position 9 by F or A or by a corresponding non-natural amino acid of amino acid F or A;
substitution of K at amino acid position 10 by R or by a corresponding non-natural amino acid of R;
substitution of I at amino acid position 11 by L or by a corresponding non-natural amino acid of L;
substitution of L at amino acid position 12 by I or W or by a corresponding non-natural amino acid of amino acid I or W;
substitution of W at amino acid position 15 by F, Y, L or I or by a corresponding non-natural amino acid of amino acid F, Y, L or I;
substitution of W at amino acid position 16 by F, Y, L or I or by a corresponding non-natural amino acid of amino acid F, Y, L or I;
substitution of Y at amino acid position 18 by Q or by a corresponding non-natural amino acid of Q;
substitution of K at amino acid position 20 by R or by a corresponding non-natural amino acid of R;
substitution of R at amino acid position 21 by K or by a corresponding non-natural amino acid of K;
substitution of an amino acid by a corresponding D-amino acid.

A polypeptide according to the invention may consist of amino acid sequence LKKLYKRLVKILKRW-WRYLKRPVR (SEQ ID NO:1) or a variant of this sequence as defined herein. As used herein a "polypeptide" refers to peptides, polypeptides and peptidomimetics that comprise multiple amino acids. The terms "polypeptide" and "peptide" are used interchangeably. The smallest polypeptide according to the invention demonstrated to have antimicrobial activity has a length of 14 amino acids. However, the amino acid sequence or variant thereof can be part of a larger polypeptide, i.e. of a polypeptide that has been N terminally and/or C-terminally extended by a one or more additional amino acids. The amino acid sequence or variant thereof of a polypeptide of the invention may be N-terminally and/or C-terminally modified, preferably by comprising an N- and/or C-terminal elongating group. Alternatively, said amino acid sequence or a variant thereof is N- and/or C-terminally extended. A polypeptide according to the invention therefore comprises at least 14 amino acids, and may comprise up to 1000 amino acids. However, smaller polypeptides are preferred in order to keep production costs as low as possible. Preferably, a polypeptide according to the invention is 14-200 amino acids in length, more preferably 14-100 amino acids, more preferably 14-50 amino acids. For instance, a polypeptide according to the invention comprises 14 to 24 amino acids, i.e. 16, 17, 18, 19, 20, 21, 22, 23 or 24 amino acids. Preferably said polypeptide comprises at least 16 amino acids, such as 16-200, 16-100 or 16-50 amino acids. Said polypeptide preferably has 14-24 amino acids. Such polypeptide having 14-24 amino acids may further have an N-terminal and/or C-terminal modification, such as an N-terminal modification selected from the group consisting of an acetyl-, hexanoyl-, decanoyl-, myristoyl-, NH—(CH2-CH2-O)11-CO— and propionyl-residu and/or such as an C-terminal modification selected from the group consisting of amide-, NH—(CH2-CH2-O)11-CO-amide- and one or two amino-hexanoyl groups. In one embodiment, a polypeptide of the invention consists of amino acid sequence LKKLYKRLVKILKRWWRYLKRPVR (SEQ ID NO:1) or a variant thereof as defined herein, preferably consisting of the amino acid sequence of P145, P148 or P159 as depicted in Table 1 or at least 14 amino acids thereof, optionally having an N-terminal and/or C-terminal modification, preferably comprising an N- and/or C-terminal elongating group.

As used herein, "peptidomimetic" refers to a compound containing non-peptidic structural elements which compound mimics the antimicrobial, antibacterial, antiviral, antifungal, antiparasitic and/or anti-inflammatory properties of a polypeptide of the invention. Hence, a polypeptide of the invention may comprise non-peptidic structural elements. Such non-peptidic structural elements may be present in the amino acid sequence of a polypeptide of the invention as a result of substitution of modification of one or more amino acids of said sequence. Alternatively, a polypeptide of the invention may comprise non-peptidic structural elements outside the amino acid sequence LKKLYKRLVKILKRWWRYLKRPVR (SEQ ID NO:1), or in a variant thereof as defined herein, i.e. in the optional N- and/or C-terminal elongating groups. A non-peptidic structural element in a peptidomimetic is typically a modification of one or more existing amino acids. Preferred peptidomimetics are obtained by structural modification of polypeptides of the invention, for instance using unnatural amino acids such as defined herein above, conformational restraints, cyclization of the polypeptide, isosteric replacement or other modifications. The amino acid sequence of a polypeptide according to the invention thus optionally comprises one or more modifications. Such polypeptide may be modified by natural processes, such as posttranslational processing, or by chemical modification techniques. Modifications may be inserted at any location in said polypeptide, including in the polypeptide backbone, amino acid side-chains and at the N- or C-terminus. A single polypeptide may contain multiple types of modifications or several modification of a single type. Modifications include acetylation, amidation, acylation, phosphorylation, methylation, demethylation, ADP-ribosylation, disulfide bond formation, ubiquitination, gamma-carboxylation, glycosylation, hydroxylation, iodination, oxidation, pegylation and sulfation. In addition a polypeptide according to the invention may be provided with a label, such as biotin, fluorescein or flavin, a lipid or lipid derivative, a sugar group. A polypeptide according to the invention can further be provided with a targeting moiety.

In a preferred embodiment, a polypeptide according to the invention is N-terminally and/or C-terminally modified. A polypeptide of the invention thus preferably comprises an N- and/or C-terminal elongating group. N- and C-terminal elongating groups that can be used in a polypeptide of the invention are well known in the art. Preferred examples of an N-terminal modification are an acetyl-, a hexanoyl-, a decanoyl-, a myristoyl-, a NH—(CH$_2$—CH$_2$—O)$_{11}$—CO— and a propionyl-residu. Preferred examples of a C-terminal modification are an amide-, a NH—(CH$_2$—CH$_2$—O)$_{11}$—CO-amide-, and one or two amino-hexanoyl groups. However, other N- or C-terminal elongating groups will also yield active compounds which is known to a person skilled in the art. In one embodiment said polypeptide comprises an N-terminal acetyl-, hexanoyl-, decanoyl-, myristoyl-, NH—(CH$_2$—CH$_2$—O)$_{11}$—CO— or propionyl-residu and a C-terminal amide-, NH—(CH$_2$—CH$_2$—O)$_{11}$—CO-amide-, and one or two amino-hexanoyl groups. In one embodiment, a polypeptide according to the invention is provided wherein the N-terminus is acetylated and the C-terminus is amidated.

The invention thus provides an isolated or recombinant polypeptide comprising an amino acid sequence LKKLYKRLVKILKRWWRYLKRPVR (SEQ ID NO:1), or a variant of said amino acid sequence, said polypeptide having antimicrobial, antibacterial, antiviral, antifungal, antiparasitic and/or anti-inflammatory activity, said variant sequence having at least 14 amino acids and optionally having one or more, preferably up to 10, of the following amino acid substitutions:

substitution of K at amino acid position 2 by R;
substitution of K at amino acid position 3 by R;
substitution of L at amino acid position 4 by V;
substitution of Y at amino acid position 5 by W;
substitution of L at amino acid position 8 by V;
substitution of V at amino acid position 9 by F or A;
substitution of K at amino acid position 10 by R;
substitution of I at amino acid position 11 by L;
substitution of L at amino acid position 12 by I or W;
substitution of W at amino acid position 15 by F, Y, L or I;
substitution of W at amino acid position 16 by F, Y, L or I;
substitution of Y at amino acid position 18 by Q;
substitution of K at amino acid position 20 by R;
substitution of R at amino acid position 21 by K; and/or
substitution of one or more amino acids by a corresponding D-amino acid, wherein said amino acid sequence or said variant thereof comprises an N- and/or C-terminal elongating group, preferably comprising an N-terminal acetyl-, hexanoyl-, decanoyl-, myristoyl-, NH—(CH$_2$—CH$_2$—O)$_{11}$—CO— or propionyl-residu and a C-terminal amide-, NH—(CH$_2$—CH$_2$—O)$_{11}$—CO-amide-, and one or two amino-hexanoyl groups. It will be clear to a person skilled in the art that other N- or C-terminal elongating groups will also yield active compounds. Herein, the numbering of amino acids is as follows: $L_1K_2K_3L_4Y_5K_6R_7L_8V_9K_{10}I_{11}L_{12}K_{13}R_{14}W_{15}W_{16}R_{17}Y_{18}L_{19}K_{20}R_{21}P_{22}V_{23}R_{24}$. Said polypeptide preferably comprises an amino acid sequence of P145, P148 or P159 as depicted in Table 1 or at least 14 amino acids thereof. Said polypeptide further preferably has 14-24 amino acids.

In a preferred embodiment, a polypeptide according to the invention comprises a hydrophobic moiety. Addition of hydrophobic groups to cationic (poly)peptides improves their ability to neutralize microbial endotoxin and to interact with microbial membranes and thus improves their ability to eliminate microbes, e.g. pathogens.

As described herein above, a polypeptide according to the invention may be modified by chemical modification techniques known in the art. The modifications of the polypeptides according to the invention can be introduced during or at the end of synthesis of the polypeptide. For instance, when the polypeptide is synthesized using solid-phase synthesis technique, N-terminal acetylation can be performed at the end by reacting the amino acid sequence, which is still bound to the resin, with acetic acid. As another example, C-terminal amidation, is for instance performed using a special kind of resin in solid-phase peptide synthesis, such as the commercially available Tentagel SAM (ex Rapp, Tübingen, Germany). These resins comprise a chemical handle from which amidated (poly)peptides are released during the cleavage. These and other methods of modifying polypeptides are known to any person skilled in the art.

In a preferred embodiment, a polypeptide according to the invention comprises a cell penetrating peptide. Such cell penetrating peptide is a peptide sequences that, when linked to a antimicrobial peptide of the invention, facilitate efficient translocation of the polypeptide across cell membranes. Any cell penetrating peptide known in the art can be used in a polypeptide of the invention. Examples of cell penetrating peptides include, but are not limited to, polyarginine, TAT, HIV-Tat, R9-TAT, Pep-1, Pep-7, penetratin, transportan, Antp, Rev, FHV coat protein, buforin II, MAP, K-FGF, Ku70, SynB1, HN-1, TP10, pVEC, BGSC, and BGTC.

A polypeptide of the invention is preferably a polypeptide that does not occur as such in nature. I.e. a polypeptide of the invention is preferably a non-naturally occurring polypeptide. "Non-naturally occurring" as used herein means that the polypeptide is not found in nature in that form, preferably that the amino acid sequence of the polypeptide is not found in nature.

Also provided is a multimer of a polypeptide of the invention comprising up to six polypeptides comprising amino acid sequence LKKLYKRLVKILKRW-WRYLKRPVR (SEQ ID NO:1) or a variant thereof as defined herein, preferably comprising the amino acid sequence of P145, P148 or P159 or at least 14 amino acids thereof. Said multimer may comprise up to six polypeptide monomers having the same amino acid sequence or up to six polypeptide monomers whereby two or more polypeptide monomer have a different amino acid sequence. In a preferred embodiment, a multimer according to the invention comprises up to six polypeptides according to the invention having the same amino acid sequence.

Salts of polypeptides according to the invention are also provided. Such salts include, but are not limited to, acid addition salts and base addition salts. As used herein, "pharmaceutically acceptable salt" of a polypeptide refers to a salt that retains the desired antimicrobial, antibacterial, antifungal, antiviral, antiparasitic and/or anti-inflammatory activity of the polypeptide, and is suitable for administration to humans or animals. Methods for the preparation of salts of polypeptides are known in the art and generally involve mixing of the polypeptide with a pharmaceutically acceptable acid or based, for instance by reacting the free acid or free base forms of the product with one or more equivalents of the appropriate acid or base in a solvent or medium in which the salt is insoluble, or in a solvent such as water which is then removed in vacuo or by freeze-drying, or by exchanging the cations of an existing salt for another cation on a suitable ion exchange resin. Examples of pharmaceutically acceptable acids and bases include organic and inorganic acids such as formic acid, acetic acid, propionic acid, lactic acid, glycolic acid, oxalic acid, pyruvic acid, succinic acid, maleic acid, malonic acid, trifluoroacetic acid, cinnamic acid, sulfuric acid, hydrochloric acid, hydrobromic acid, nitric acid, perchloric acid, phosphoric acid, and thiocyanic acid, which form ammonium salts with free amino groups of polypeptides, and bases which form carboxylate salts with free carboxylic groups of polypeptides, such as ethylamine, methylamine, dimethylamine, triethylamine, isopropylamine, diisopropylamine, and other mono-, di- and trialkylamines, and arylamines.

Polypeptides according to the invention can be prepared by various methods. For instance, a polypeptide can be synthesized by commonly used solid-phase synthesis methods, e.g. methods that involve t-BOC or FMOC protection of alpha-amino groups which are well known in the art. Here, amino acids are sequentially added to a growing chain of amino acids. Such methods are for instance described in Merrifield (1963), J. Am. Chem. Soc. 85: 2149-2156; and Atherton et al., "Solid Phase Peptide Synthesis," IRL Press, London, (1989). Solid-phase synthesis methods are particularly suitable for synthesis of polypeptides or relatively short length, such as polypeptides with a length of up to about 70 amino acids in large-scale production.

Alternatively, a polypeptide of the invention can be prepared using recombinant techniques well known in the art in which a nucleotide sequence encoding the polypeptide is expressed in host cells. The invention thus provides a method for the preparation of a polypeptide according to the invention comprising:

providing a nucleic acid molecule comprising a nucleic acid sequence encoding a polypeptide according to the invention;

transforming a host cell with said nucleic acid molecule;

culturing said host cell under conditions that allow expression of said polypeptide;

harvesting said polypeptide from said cells;

optionally N-terminally or C-terminally modifying said polypeptide, for instance by addition an N- and/or C-terminal elongating group.

The invention further provides a nucleic acid molecule comprising a nucleic acid sequence encoding a polypeptide according to the invention, which is herein also referred to as a nucleic acid molecule according to the invention. As used herein, a nucleic acid molecule or nucleic acid sequence of the invention comprises a chain of nucleotides, preferably DNA and/or RNA.

Further provided is a vector comprising a nucleic acid sequence molecule according to the invention. The term "vector" as used herein refers to a nucleic acid molecule, such as a plasmid, bacteriophage or animal virus, capable of introducing a heterologous nucleic acid sequence into a host cell. A vector according to the invention allows the expression or production of a polypeptide of the invention encoded by the heterologous nucleic acid sequence in a host cell. A vector used in accordance with the invention is for instance derived from an animal virus, examples of which include, but not limited to, vaccinia virus (including attenuated derivatives such as the Modified Vaccinia virus Ankara, MVA), Newcastle Disease virus (NDV), adenovirus or retrovirus. A vector according to the invention preferably comprises an expression cassette comprising a promoter that is suitable for initiation of transcription of a polypeptide according to the invention in the selected host cells. Examples of suitable promoters for expression of polypeptides according to the invention in eukaryotic host cells include, but are not limited to, beta-actin promoter, immunoglobin promoter, 5S RNA promoter, or virus derived promoters such as cytomegalovirus (CMV), Rous sarcoma virus (RSV) and Simian virus 40 (SV40) promoters for mammalian hosts.

Further provided by the invention is a recombinant host cell comprising a nucleic acid molecule and/or a vector according to the invention. A host cell is a cell which has been transformed, or is capable of transformation, by a nucleic acid molecule such as a vector according to the invention. "Transformation" refers to the introduction of a foreign nucleic acid into a recipient cell. Transformation of a host cell can result in transient expression of a recombinant protein by said cell, meaning that the recombinant protein is only expressed for a defined period of time. Alternatively, transformation of a recipient cell can result in stable expression, meaning that the nucleic acid is introduced into the genome of the cell and thus passed on to next generations of cells. Additionally, inducible expression of a recombinant protein can be achieved. An inducible expression system requires the presence or absence of a molecule that allows for expression of a nucleic acid sequence encoding a polypeptide of the invention. Examples of inducible expression systems include, but are not limited to, Tet-On and Tet-Off expression systems, hormone inducible gene expression system such as for instance an ecdysone inducible gene expression system, an arabinose-inducible gene expression system, and a *Drosophila* inducible expression system using a pMT/BiP vector (Invitrogen) which comprises an inducible metallothioneine promoter. A host cell used in a method for the preparation of a polypeptide according to the invention is for instance a Gram-positive prokaryote, a Gram-negative prokaryote or an eukaryote. Preferably said host cell is an eukaryotic cell, such as a plant cell, a yeast cell, a mammalian cell or an insect cell, most preferably an insect cell or a mammalian cell. Examples of suitable host cells include plant cells such as corn cells, rice cells, duckweed cells, tobacco cells (such as BY-2 or NT-1 cells), and potato cells. Examples of yeast cells are *Saccharomyces* and *Pichia*. Examples of insect cells are *Spodoptera frugiperda* cells, such as Tn5, SF-9 and SF-21 cells, and *Drosophila* cells, such as *Drosophila* Schneider 2 (S2) cells. Examples of mammalian cells that are suitable for expressing a polypeptide according to the invention include, but are not limited to, African Green Monkey kidney (Vero) cells, baby hamster kidney (such as BHK-21) cells, Human retina cells (for example PerC6 cells), human embryonic kidney cells (such as HEK293 cells), Madin Darby Canine kidney (MDCK) cells, Chicken embryo fibroblasts (CEF), Chicken embryo kidney cells (CEK cells), blastoderm-derived embryonic stem cells (e.g. EB14), mouse embryonic fibroblasts (such as 3T3 cells), Chinese hamster ovary (CHO) cells, and derivatives of these cell types.

A method according to the invention preferably further comprises a step of harvesting, purifying and/or isolating polypeptides according to the invention. Obtained polypeptides according to the invention are preferably used in human therapy, optionally after additional purifying, isolation or processing steps, for instance purification using gel electrophoresis or chromatography methods A polypeptide according to the invention exhibits a number of activities that can be advantageously used in both therapeutic and nontherapeutic applications. In particular, polypeptides according to the invention are useful in counteracting various microbial infections, such as bacterial infections, fungal infections, viral infections, and in counteracting parasitic infections. Provided are thus pharmaceutical compositions comprising a polypeptide according to the invention or a pharmaceutically acceptable salt thereof, and at least one pharmaceutically acceptable carrier, diluent and/or excipient. Also provided are pharmaceutical compositions comprising a nucleic acid molecule or vector according to the invention and at least one pharmaceutically acceptable carrier, diluent and/or excipient.

The invention further provides a polypeptide according to the invention for use as a medicament. Further provided is a nucleic acid molecule comprising a nucleic acid sequence encoding a polypeptide according to the invention for use as a medicament. Said medicament can be a therapeutic or a prophylactic agent.

In one embodiment, the invention provides a method for the treatment of a subject suffering from or at risk of suffering from a bacterial, fungal, viral and/or parasitic infection comprising administering to said subject a therapeutically effective amount of a polypeptide according invention, a pharmaceutical composition according to the invention or a nucleic acid molecule according to the invention. Also provided is a method for the preparation of a medicament for the treatment of a subject infected with a microbe or for prophylaxis of a microbial infection. In a preferred embodiment, said microbe is a bacterium, a fungus, a virus or a parasite. Further provided is a polypeptide and/or nucleic acid molecule for use according to the invention in the prevention or treatment of a microbial, bacterial, fungal, viral and/or parasitic infection or a condition resulting from a microbial, bacterial, fungal, viral and/or parasitic infection.

As used herein, an "subject" is a human or an animal. Subjects include, but are not limited to, mammals such as humans, pigs, ferrets, seals, rabbits, cats, dogs, cows and horses, and birds such as chickens, ducks, geese and turkeys. In a preferred embodiment of the invention a subject is a mammal. In a particularly preferred embodiment the subject is a human.

The invention also provides a method for inhibiting the growth of a microbe, e.g. a bacterium, a virus, a fungus, or a parasite comprising contacting said microbe or parasite with a polypeptide or pharmaceutical composition according to the invention. Said contacting can be performed in vivo and in vitro.

The polypeptides and pharmaceutical compositions according to the invention are effective in treating a variety of microbial infections, such as various viral, bacterial and fungal infections. For example, the polypeptides and pharmaceutical compositions are effective in treating Gram-negative and Gram-positive bacteria. Examples of pathogenic bacteria that may cause infections in humans or animals that are treatable with polypeptides and compositions of the invention include, but are not limited to, *Listeria, Escherichia, chlamydia*, rickettsial bacteria, mycobacteria, staphylococci, streptocci, pneumonococci, meningococci, *Klebsiella, pseudomonas, Legionella*, diphtheria, *salmonella*, bacilli, *Vibrio cholerae*, tetanus, *Clostridium, Bacillus, Yersinia*, and *Leptospira* bacteria.

Examples of pathogenic viruses that may cause infections in humans or animals that are treatable with polypeptides and compositions of the invention include, but are not limited to, A, B or C hepatitis, herpes virus (for instance VZV, HSV-I, HAV-6, HSV-II, CMV, EpsteinBarr-virus), adenovirus, influenza virus, flaviviruses, echovirus, rhinovirus, coxsackie virus, coronavirus, respiratory syncytial virus (RSV), rotavirus, Morbillivirus, rubella virus, parvovirus, vaccinia virus, HTLV virus, dengue virus, papillomavirus, poliovirus, rabies virus and human immunodeficiency virus (HIV virus; e. g., type I and II).

Examples of pathogenic fungi that may cause infections in humans or animals that are treatable with polypeptides and compositions of the invention include, but are not limited to, *Candida* (e.g., *albicans, krusei, glabrata, tropicalis*), *Aspergillus* (e.g., *fumigatus, niger*), *Cryptococcus neoformans, Histoplasma capsulatum*, Genus *Mucorales, Blastomyces dermatitidis, Paracoccidioides brasiliensis*, and *Coccidioides immitis*.

Examples of pathogenic parasites that may cause infections in humans or animals that are treatable with polypeptides and compositions of the invention include, but are not limited to, *Entamoeba histolytica, Plasmodium* (e.g. falciparum, vivax), *Entamoeba*, Giardia, *Balantidium coli, Acanthamoeba, Cryptosporidium* sp., *Pneumocystis carinii, Babesia microti, Trypanosoma* (e.g. brucei, cruzi), *Leishmania* (e.g. donovani), and *Toxoplasma gondii*.

In preferred embodiment, polypeptides and pharmaceutical compositions of the invention are effective in treating infections caused by methicillin-resistant *Staphylococcus aureus* (MRSA) and (non-resistant) *S. aureus, Staphylococcus epidermidis*, the Gram-negative bacterium *Pseudomonas aeruginosa* and the fungal species *Candida albicans* and *Aspergillus niger*.

The compositions containing the polypeptides can be administered for prophylactic and/or therapeutic treatments. In therapeutic applications, polypeptides or compositions are administered to a subject, preferably a human, already suffering from a disease in an amount sufficient to counteract the symptoms of the infection or the condition resulting from the infection and its complications. In prophylactic applications, polypeptides or compositions are administered to a subject, for instance a human or animal at risk of suffering from a microbial or parasitic infection in an amount sufficient to prevent infection or at least inhibit the development of an infection. The polypeptide is typically present in a pharmaceutical composition according to the invention in a therapeutic amount, which is an amount sufficient to remedy a condition or disease, particularly symptoms associated with a microbial or parasitic infection. Typical doses of administration of a polypeptide according to the invention or combinations of at least two thereof are between 0.01 and 10 mg polypeptide per kg body weight, depending on the size of the polypeptide.

Polypeptides and pharmaceutical composition of the invention are suitable for a wide variety of applications. For instance, they can be used for topical application, e.g. in the treatment or prevention of skin infections, wound infections and urinary tract infections. As detailed herein before, polypeptides of the invention are capable of preventing biofilm formation and disperse existing biofilms, kill the bacteria, fungi or other microbes at and around the site of biofilm formation, and modulate immune responses by neutralizing pro-inflammatory microbial endotoxins. Bacterial biofilms may delay cutaneous wound healing and reduce topical antibacterial efficiency of conventional antibiotics in healing or treating infected skin wounds, skin infections or urinary tract infections. The invention therefore provides a polypeptide, pharmaceutical composition and/or nucleic acid molecule according to the invention for use in the treatment or prevention of skin infection, wound infection and/or urinary tract infections. Also provide is a polypeptide, pharmaceutical composition and/or nucleic acid molecule according to the invention for use in would healing. Further provided is the use of a polypeptide, pharmaceutical composition and/or nucleic acid molecule according to the invention in the manufacture of a pharmaceutical composition for the treatment or prevention of skin infection, wound infection, urinary tract infection and/or for wound healing. The invention further provides a method for the treatment of a subject suffering from skin infection, wound infection and/or urinary tract infection comprising administering to said subject a therapeutically effective amount of a polypeptide according invention, a pharmaceutical composition according to the invention or a nucleic acid molecule according to the invention.

Polypeptides of the invention can further advantageously used as a preservative for materials that are susceptible to microbial, e.g. bacterial, viral, fungal, parasitic, infection. Such material can be impregnated or coated with or covered by a polypeptide of the invention. As detailed herein before, polypeptides of the invention are retain antimicrobial activity in blood, plasma and serum, and in the presence of components, such as plasma components. Polypeptides and pharmaceutical composition of the invention are therefore particularly suitable for systemic application and for treatment and/or prevention of infection associated with implants and medical devices. The term "medical devices" as used herein refers to any type of device that can be used in the human or animal body and includes, but is not limited to, medical instruments, medical implements, prostheses, such as artificial joints including hips and knees, and dental prostheses, breast implants, implantable devices such as pace makers, heart valves, stents, catheters, ear tubes, splints, screws for medical devices, and wound or tissue dressings. Implants and medical devices are often associated with microbial infection, in particular with biofilm infections, which are successfully counteracted by polypeptides of the present invention as demonstrated in the Examples. Further, implants and medical devices are generally rapidly covered by plasma components from the hosts fluids after implantation. Because the polypeptides of the invention exert antimicrobial activity in the presence of plasma components as demonstrated in the Examples, microbial infection of implants and/or medical devices is effectively treated and/or prevented by a polypeptide according to the invention. Provided is therefore the use of a polypeptide of the invention as a preservative for an implant and/or medical device. Also provided is a polypeptide of the invention for use in prevention and/or treatment of microbial infection, preferably bacterial infection, of an implant and/or medical devices.

A polypeptide of the invention is advantageously incorporated in a controlled release and/or targeted delivery carrier. As used herein, the term "controlled release" refers to the release of the polypeptide of the invention in time dependent manner. In one embodiment, controlled release refers to slow release. As used herein, the term "targeted delivery" refers to the release of the polypeptide of the invention in a site-directed manner. Use of a controlled release vehicle has the advantage that frequent administration such as by injection of the polypeptide of the invention can be avoided. Use of a targeted delivery vehicle has the advantage that the polypeptide of the invention is effectively delivered to and/or retained at a site of interest in a subject's body, such as a site of inflammation or a site of infection. Preferably, a polypeptide of the invention is targeted to a site infected by microorganisms including bacteria, fungi, viruses and parasites. Controlled release and/or targeted delivery carriers are well known in the art. Non limiting examples of controlled release and/or targeted delivery vehicles are nanoparticles, microp articles, nanocapsules, microcapsules, liposomes, microspheres, hydrogels, polymers, lipid complexes, serum albumin, antibodies, cyclodextrins and dextrans. Controlled release is for instance provided by incorporating a polypeptide of the invention in or on the surface of such carrier. The carriers are of materials that form particles that capture a polypeptide of the invention and slowly degrade or dissolve in a suitable environment, such as aqueous, acidic or basic environment or body fluids, and thereby release the polypeptide. Targeted delivery is for instance achieved by providing a carrier with targeting groups on the surface thereof. Examples of such carrier comprising targeting groups are antibody-functionalized carriers, carriers having a site-specific ligand and carriers having a positive or negative surface charge. Preferred particles for controlled release and/or targeted delivery are nanoparticles, i.e., particles in the range of about 1 to 500 nm in diameter, preferably up to about 200 nm in diameter, and liposomes, optionally provided with targeting groups. The invention therefore provides a controlled release carrier comprising a polypeptide of the invention and pharmaceutical compositions comprising such controlled release carrier. Also provided is a targeted delivery carrier comprising a polypeptide of the invention, and a pharmaceutical composition comprising such targeted delivery carrier. Said carrier is preferably selected from the group consisting of nanoparticles, microparticles, nanocapsules, microcapsules, liposomes, microspheres, hydrogels, polymers, lipid complexes, serum albumin, antibodies, cyclodextrins and dextran.

Preferred targeted delivery and/or controlled release carriers are of biodegradable material. "Biodegradable" as used herein refers to molecules that degrade under physiological conditions. This includes molecules that are hydrolytically degradable and molecules that require enzymatic degradation. Suitable biodegradable materials include, but are not limited to, biodegradable polymers and natural biodegradable material such as PLA (poly lactic acid), PGA (poly glycolic acid), polycaprolactone (PCA), polyethylene oxide (PEO), polydioxanone (PDS), polycaprolactone (PCL), polypropylene fumarate, polymers derived from lactones, such as lactide, glycolide and caprolactone, carbonates such as trimethylene carbonate and tetramethylene carbonate, dioxanones, ethylene glycol, polyester amide (PEA) ethylene oxide, esteramides, γ-hydroxyvalerate, β-hydroxypropionate, α-hydroxy acid, hydroxybuterates, hydroxy alkanoates, polyimide carbonates, polyurethanes, polyanhydrides, and combinations thereof, polysaccharides such as hyaluronic acid, chitosan and cellulose, and proteins such as gelatin and collagen.

Further provided is a coating, preferably for implants and/or medical devices, comprising a polypeptide of the invention. In one embodiment, such coating provides for controlled release of the polypeptide of the invention. Such controlled release coating for medical devices preferably comprises a biodegradable material so that release of the polypeptide of the invention is achieved by degradation of the coating material. Also provided is therefore a controlled release coating comprising a polypeptide of the invention. Further provided is a medical device comprising such coating comprising a polypeptide of the invention and a biodegradable material. Further provided is an implant comprising such coating comprising a polypeptide of the invention and a biodegradable material. A biodegradable coating in accordance with the invention comprises a biodegradable material as defined above. In particular, such biodegradable coating comprises a material selected from the group consisting of PLA (poly lactic acid), PGA (poly glycolic acid), polycaprolactone (PCA), polyethylene oxide (PEO), polydioxanone (PDS), polycaprolactone (PCL), polypropylene fumarate, polymers derived from lactones, such as lactide, glycolide and caprolactone, carbonates such as trimethylene carbonate and tetramethylene carbonate, dioxanones, ethylene glycol, polyester amide (PEA) ethylene oxide, esteramides, γ-hydroxyvalerate, β-hydroxypropionate, α-hydroxy acid, hydroxybuterates, hydroxy alkanoates, polyimide carbonates, polyurethanes, polyanhydrides, and combinations thereof, polysaccharides such as hyaluronic acid, chitosan and cellulose, and proteins such as gelatin and collagen. Further, provided is a method of preventing and/or treating of microbial infection, preferably bacterial infection, of an implant and/or medical device comprising providing said implant and/or medical device with a coating comprising a polypeptide of the invention and implanting said implant or medical device in a subject.

The polypeptides and pharmaceutical compositions are also useful as anti-inflammatory agents as they neutralize pro-inflammatory microbial endotoxins such as lipoteichoic acid, peptidoglycan and lipopolysaccharides thereby inhibiting, reducing or preventing influx of neutrophils, macrophages/monocytes and lymphocytes and the release of pro-inflammatory microbial compounds by the infected subject. Also provided is therefore a method for inhibiting the release of pro-inflammatory compounds comprising contacting a cell capable of releasing pro-inflammatory compounds with a polypeptide according to the invention. Said contacting can be performed in vivo and in vitro. Further provided is a polypeptide according to the invention for use as an anti-inflammatory agent.

Although polypeptides according to the invention are potent antimicrobial agents, they can be combined with known antimicrobial agents, such as conventional anti-infectives, such as antibiotics, antivirals and antifungals or other antimicrobial peptides, and antibodies and chemicals e.g. sensitizers, nanoparticles. Such combination may result in an increased antimicrobial activity or broaden the spectrum of activity. Polypeptides of the invention may for instance be combined with penicillins, cephalosporins, macrolides, fluoroquinolones, sulfonamides, tetracylcines and/or aminoglycosides for treating bacterial infections. For treatment of viral infections polypeptides may be combined with antiviral nucleoside analogs such as aciclovir, ganciclovir, zidovudine (AZT) or didanosine or neuramidase inhibitors such as oseltamivir, peramivir or zanamivir. For treatment of fungal infections the polypeptides and compositions of the invention may be combined with polyene antifungals, imidazoles, triazoles, allylamines, echinocandins, ciclopirox, flucytosine and/or griseofulvin. The invention therefore provides a pharmaceutical composition comprising a polypeptide according to the invention and an additional antimicrobial agent, such as a antibiotic or an antimicrobial peptide, preferably selected from the group consisting of penicillins, cephalosporins, carbapenems and mupirocin.

Pharmaceutical compositions according to the invention comprise at least one pharmaceutically acceptable carrier, diluent or excipient. Examples of suitable carriers for instance comprise keyhole limpet haemocyanin (KLH), serum albumin (e.g. BSA or RSA) and ovalbumin. In a preferred embodiment said suitable carrier is a solution, for example saline. Examples of excipients which can be incorporated in tablets, capsules and the like are the following: a binder such as gum tragacanth, acacia, corn starch or gelatine; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor. A pharmaceutical composition according to the invention is preferably suitable for human use.

The pharmaceutical compositions described herein can be administered in a variety of different ways. Examples include administering a pharmaceutical composition comprising a polypeptide according to the invention and containing a pharmaceutically acceptable carrier via oral, intranasal, rectal, topical, intraperitoneal, intravenous, intramuscular, subcutaneous, subdermal, transdermal, intrathecal, and intracranial methods. For oral administration, the active ingredient can be administered in solid dosage forms, such as capsules, tablets, and powders, or in liquid dosage forms, such as elixirs, syrups, and suspensions.

Sterile compositions for injection can be formulated according to conventional pharmaceutical practice by dissolving or suspending the polypeptide of the invention in a vehicle for injection, such as water or a naturally occurring vegetable oil like sesame oil, coconut oil, peanut oil, cottonseed oil, etc., or a synthetic fatty vehicle like ethyl oleate or the like. Buffers, preservatives, antioxidants and the like may also be incorporated.

Compositions for topical administration can also be formulated according to conventional pharmaceutical practice. "Topical administration" as used herein refers to application to a body surface such as the skin or mucous membranes to locally treat conditions resulting from microbial or parasitic infections. Examples of formulations suitable for topical administration include, but are not limited to a cream, gel, ointment, lotion, foam, suspension, spray, aerosol, powder aerosol. Topical medicaments can be epicutaneous, meaning that they are applied directly to the skin. Topical medicaments can also be inhalational, for instance for application to the mucosal epithelium of the respiratory tract, or applied to the surface of tissues other than the skin, such as eye drops applied to the conjunctiva, or ear drops placed in the ear. Said pharmaceutical composition formulated for topical administration preferably comprises at least one pharmaceutical excipients suitable for topical application, such as an emulgent, a diluent, a humectant, a preservatives, a pH adjuster and/or water.

A polypeptide according to the invention is also particularly suitable for diagnostic use. The polypeptides may be used for the detection of microbial infection, for instance by the detection of microbial toxins, e.g. bacterial toxins including LPS, LTA and PG, present in physiological samples, such as blood, plasma, mucus, wound exudate and urine. Further, the polypeptides can be used for determining the amount of microbial toxins in such samples. Provided is therefore a polypeptide nucleic acid molecule according to the invention for use as a diagnostic agent. Further provided is a use of a polypeptide according to the invention for detecting a microbial toxin, preferably a bacterial or fungal toxin, in a physiological sample, such as a blood, plasma, mucus, wound exudate and urine sample. As described above, a polypeptide according to the invention can be coupled to a suitable moiety such as a biotin, a fluorescein label, a near infrared dye or a radioactive isotope. Such labeled polypeptides can be used in a method for detecting microbial infections such as bacterial infections because they migrate to a site of microbial infection. Using a detector suitable for the used label attached to the polypeptide, it is possible to detect infection sites. Methods for detecting microbial infections such as bacterial infections are therefore also provided by the invention. The method typically involves administering a labeled polypeptide to a subject infected with, or suspected of being infected with, a microbial organism. Because the labeled polypeptide is capable of interacting with the infectious organism, it accumulates at the site of infection. For detecting microbial toxins in a physiological sample, the method involves administering a labeled polypeptide to a physiological sample of a subject infected with, or suspected of being infected with, a microbial organism. It is possible to detect the accumulation of the polypeptide at site of infection or in a sample using various detectors which are sensitive to the label that is attached to the polypeptide.

Another useful application of polypeptides according to the invention is in preservation of food products. Also provided is therefore the use of a polypeptide according to the invention as a food preservative. Generally, pathogenic or spoilage microorganism are destroyed by thermally processing foods by subjecting them to temperatures varying from 60 to 100° C. Such treatment may have undesirable effects on the food product, such as undesirable organoleptic effects. Use of a polypeptide according to the invention as a preservative in food products may result in extended storage life and/or enhanced safety of the food product.

Pathogenic microorganisms in foods may cause infections or intoxication of subjects, and include bacteria such as *Campylobacter jejuni, Salmonella typhi, Salmonella paratyphi* and non-*typhi Salmonella* species, *Staphylococcus aureus, Escherichia coli, Listeria monocytogenes, Shigella* and *Clostridium Botulinum*, viruses such as Rotaviruses and Norwalk virus, parasites such as *Taenia solium, Taenia saginata* and *Trichinella spiralis* and moulds. Food spoilage refers to the change of look, consistency, flavor and/or odor of food products, and may be caused by bacteria such as *Lactobacillus, Leuconostoc, Pseudomonas, Micrococcus, Flavobacterium, Serratia, Enterobacter* and *Streptococcus*, fungi such as *Aspergillus, Fusarium* and *Cladosporium* and yeasts.

The invention will be explained in more detail in the following, non-limiting examples.

EXAMPLES

Materials and Methods

Synthesis of Antimicrobial Peptides

Figure 1:
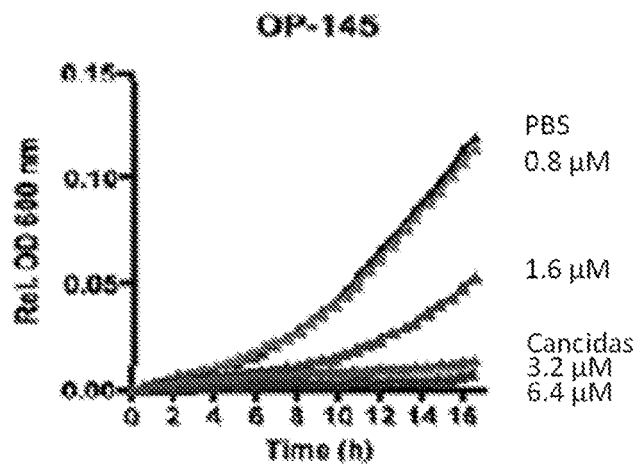
FIG. 1: Growth curves of *A. niger* cultured in PBS in the presence of 5 µM Cancidas, or 0.8-6.4 µM of the indicated peptides. Values are expressed as optical density at 600 nm relative to the optical density at 0 h. Light micrographs of fungal growth in PBS after 16 hours of incubation. Representative light micrographs of triplicates.
Figure 1:
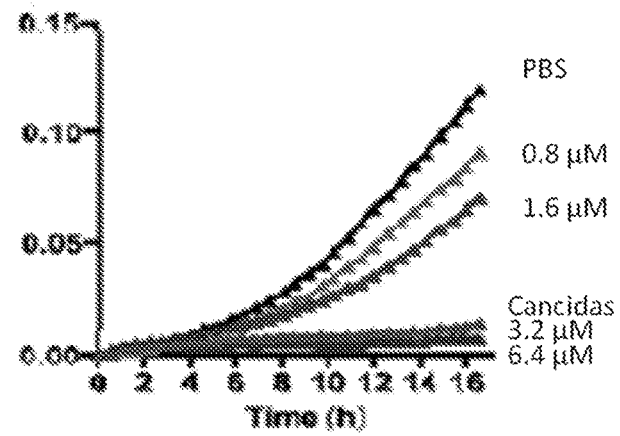

Synthetic peptides were prepared by normal Fmoc-chemistry using preloaded Tentagel resins, PyBop/NMM for in situ activation and 20% piperidine in NMP for Fmoc removal [Hiemstra H S et al. Proc Natl Acad Sci USA, 94, 10313-10318 (1997)]. Couplings were performed for 60 min with 6-fold acylating species. After final Fmoc removal peptides were cleaved with TFA/H$_2$O 19/1 (v/v) containing additional scavengers when C (triethylsilane) or W (ethanethiol) were present in the peptide sequence. Peptides were isolated by ether/pentane 1/1 (v/v) precipitation and isolation of the product by centrifugation. After air-drying at about 40° C., peptides were dissolved in acetic acid/water 1/10 (v/v) and lyophilized. Peptides were checked on purity using UPLC-MS (Acquity, Waters) and on integrity using Maldi-Tof mass spectrometry (Microflex, Bruker), showing the expected molecular masses.

Abbreviations

Fmoc: 9H-fluorenylmethyloxycarbonyl
NMM: N-methylmorpholin
PyBOP: Benzotriazol-1-yl-oxy-tris-pyrrolidino-phosphonium hexafluorophosphate
TFA: trifluoro acetic acid
Bacterial Strains The clinical isolate of methicillin-resistant *Staphylococcus aureus* (MRSA), LUH14616 was kindly provided by dr. S. Croes, Maastricht University Medical Center, Maastricht, Netherlands (see Croes S BMC Microbiol. 2009; 9:229. doi: 10.1186/1471-2180-9-229).

*S. aureus* JAR is described in Campoccia et al. (Int J Artif Organs. 2008 Sep.; 31(9):841-7).

*Staphylococcus epidermidis* RP62a is described in Infect. Immun. 2008; 75: 1129-1136.

*Pseudomonas aeruginosa* PAO1 is described in Nucl. Acids Res 2011; 39, Suppl. 1: D596-D60.

Bacteria were stored at −80° C. until use. Inoculi of mid log phase bacteria were prepared by incubating isolated bacterial colonies from blood agar plates in Tryptic Soy Broth (TSB) medium (Becton Dickinson, Le Pont de Clax, France) for 2.5 hours and then diluted to the concentration needed. Stationary phase *S. aureus* JAR060131 was obtained from 18-20 hour cultures.
Determination of Antibacterial Activity Peptides were incubated with 1×10$^6$ CFU/ml of a mid-logarithmic culture of *S. aureus* JAR060131, methicillin resistant *S. aureus* (MRSA) LUH14616, *Staphylococcus epidermidis* RP62a, and *Pseudomonas aeruginosa* PAO1 in PBS without or with addition of pooled human plasma (Sanquin, Amsterdam, the Netherlands) at a final concentration of 50%. Antimicrobial activity is expressed as the 99.9% lethal concentration (LC99.9), i.e., the lowest peptide concentration which killed ≥99.9% of bacteria after 2 hours of incubation at 37° C. under shaking conditions.

To assess the antimicrobial activity of the peptides towards stationary phase bacteria, peptides were incubated under the conditions described above with 1×10$^6$ CFU/ml of stationary phase *S. aureus* JAR060131, obtained from 18-20 hour cultures.

Determination of Antifungal Activity

Peptides were incubated with 1×10$^5$ cells/ml of a mid-logarithmic culture of *Candida albicans* Y-O1, without or with addition of pooled human plasma at a final concentration of 50%. Antimicrobial activity is expressed as the 99% lethal concentration (LC99), i.e., the lowest peptide concentration at which ≥99% of cells were killed after 2 hours of incubation at 37° C. under shaking conditions.

The effect of the peptides on fungal growth was assessed using *Aspergillus niger*. Peptides were incubated with 7.5× 10$^4$ spores/ml of *A. niger* PagsA-lux in PBS without or with addition of pooled human plasma at a final concentration of 25%. As positive control, spores were treated with the antifungal caspofungin (Cancidas). Absorbance was measured over time and at 16 hours, fungal growth was visualized using light microscopy.
Determination of Antibiofilm Activity Peptides were incubated with 1×10$^8$ CFU/ml of *S. aureus* JAR060131 in biofilm-adjusted BM2 in 96-wells polypropylene plates as described in Antimicrob Agents Chemother 2012; 56: 2696-2704. After 24 hours incubation at 37° C., planktonic bacteria were removed by four washes with PBS and biofilms were stained with crystal violet. After solubilization with ethanol, the optical density at 590 nm was determined as a measure of biofilm mass. Antibiofilm activity is expressed as the 50% inhibitory concentration (IC50), i.e., the lowest peptide concentration that resulted in ≥50% reduction of biofilm mass.

To assess the antibiofilm activity of the peptides in the presence of plasma, 96-wells polypropylene plates were coated with plasma by overnight incubation with 20% plasma at 4° C. Wells were washed once with sterile water and inoculated with *S. aureus* and peptides as described above.
Immunodulatory Activity: LPS and LTA Neutralization Peptides were pre-incubated with 500 ng/ml LPS (*E. coli* 054) or 2 mg/ml LTA (*S. aureus*, endotoxin-free) or 1×10$^9$ CFU/ml of UV-killed *S. aureus* JAR060131 for 30 min at 37° C. Diluted whole human blood was stimulated with the peptide-LPS/LTA/*S. aureus* mixtures for 20 hours at 37° C. IL-12p40 and IL-8 levels in supernatants were determined using ELISA. LPS and LTA neutralizing activity is expressed as the 50% or 90% inhibitory concentration (IC50 and IC90), i.e., the lowest peptide concentration that resulted in ≥50 or ≥90% reduction in the LPS/LTA/*S. aureus*-induced IL-12p40 or IL-8 production.
Results
Identification of 25 Peptides Derived from OP-145

New peptides that are antimicrobial and that are less susceptible to plasma components compared to OP-145 were identified based on computer prediction.

OP-145 is predicted to adopt an amphipathic helical structure. In such a structure the peptide is folded in an α-helix, that contains charged groups at one side of the helix and hydrophobic groups at the opposite site. From previous studies in which peptides with amino acid substitutions were applied we know that introduction of charged groups that end up at the hydrophobic side of the helix, or introduction of hydrophobic groups that end up at the charged side of the helix yield compounds with diminished antibacterial activity.

We thus decided that newly designed peptides should be predicted to fold in an amphipathic helix. Based on the sequence of OP-145, we designed the motif below for amino acid substitution. We focused on substitutions that yield peptides that are importantly distinct from OP-145, minimizing structure resemblance to OP-145 and maximizing the chance that binding to plasma components that affect antimicrobial activity are minimized.

Computer prediction revealed that the below motif will yield peptides with an amphipathic helix.

```
                1 1 1 1 1 1 1 1 1 1 2 2 2 2
1 2 3 4 5 6 7 8 9 0 1 2 3 4 5 6 7 8 9 0 1 2 3 4
L K K L Y K R L V K I L K R W W R Y L K R P V R
R R V W     V F R L I     F F     Q     R K
        A       W           Y Y
                            L L
                            I I
```

The below 25 peptides were selected on the basis of the motif (J=acetyl, B=amide).

TABLE 1

Sequence of peptides P139-163.

P139 J L K K L W K R V F R I W
     K R I F R Y L K R P V R B

P140 J L R R L W K R L V R I I
     K R I Y R Q L K R P V R B

P141 J L R R L Y K R V F R L L
     K R W W R Y L K R P V R B

P142 J L R R L W K R L V K I L
     K R W F R Y L R R P V R B

P143 J L R R L Y K R V V K L W
     K R L F R Q L R R P V R B

P144 J L K K L Y K R V A K I W
     K R W I R Y L K K P V R B

P145 J L K R L Y K R L A K L I
     K R L Y R Y L K K P V R B

P146 J L K K L Y K R L F K I L
     K R I L R Y L R K P V R B

P147 J L K K L W K R L A R L L
     K R F I R Q L R R P V R B

P148 J L K R V W K R V F K L L
     K R Y W R Q L K K P V R B

P149 J L K K V Y K R L A R L L
     K R Y I R Y L R R P V R B

P150 J L K K V W K R V A R L I
     K R W F R Y L R R P V R B

P151 J L K K L Y K R L F K L W
     K R L Y R Y L K K P V R B

P152 J L R R V Y K R L A R L I
     K R Y L R Q L K K P V R B

P153 J L R K L W K R V V K I W
     K R Y L R Q L R R P V R B

P154 J L R K L W K R L A K I I
     K R L Y R Y L R R P V R B

P155 J L K K V Y K R V A R L I
     K R L F R Y L K R P V R B

P156 J L R R L W K R L V K L W
     K R F F R Y L K K P V R B

P157 J L K K V W K R V F R I L
     K R F L R Y L K R P V R B

TABLE 1-continued

Sequence of peptides P139-163.

P158 J L R R V Y K R L F R L W
     K R I I R Q L R R P V R B

P159 J L K R L Y K R V F R L L
     K R Y Y R Q L R R P V R B

P160 J L K K L W K R L A R L W
     K R I I R Q L K K P V R B

P161 J L R R V W K R V A R I I
     K R L Y R Y L K R P V R B

P162 J L K R L W K R L F K I L
     K R Y Y R Y L R R P V R B

P163 J L R R L W K R V F K I I
     K R L F R Q L K K P V R B

J = acetyl, B = amide

These peptides were tested on their antibacterial activity in absence and the presence of plasma (Table 2).

Based on the results obtained P145, P148 and P159 were selected as significantly improved peptides compared to OP-145.

TABLE 2

Antimicrobial activities of peptides derived from OP-145.

| Peptide | | Antimicrobial activity[1] IC99.9 (µM) | |
|---|---|---|---|
| | | PBS | 50% plasma |
| (OP-145) | 1145-01 | 1.6 | 204.8 |
| (P139) | 1231-01 | 0.8 | 51.2 |
| (P140) | 1231-02 | 1.6 | 25.6 |
| (P141) | 1231-03 | 0.8 | 25.6 |
| (P142) | 1231-04 | 0.8 | 51.2 |
| (P143) | 1231-05 | 1.6 | 51.2 |
| (P144) | 1231-06 | 1.6 | 25.6 |
| (P145) | 1231-07 | 1.6 | 25.6 |
| (P146) | 1231-08 | 1.6 | 51.2 |
| (P147) | 1231-09 | 1.6 | 51.2 |
| (P148) | 1231-10 | 1.6 | 12.8 |
| (P149) | 1231-11 | 1.6 | 102.4 |
| (P150) | 1231-12 | 1.6 | 25.6 |
| (P151) | 1231-13 | 1.6 | 25.6 |
| (P152) | 1231-14 | 1.6 | 25.6 |
| (P153) | 1231-15 | 1.6 | 25.6 |
| (P154) | 1231-16 | 1.6 | 51.2 |
| (P155) | 1231-17 | 1.6 | 102.4 |
| (P156) | 1231-18 | 1.6 | 51.2 |
| (P157) | 1231-19 | 0.8 | 51.2 |
| (P158) | 1231-20 | 1.6 | 25.6 |
| (P159) | 1231-21 | 1.6 | 12.8 |
| (P160) | 1231-22 | 1.6 | 25.6 |
| (P161) | 1231-23 | 1.6 | 25.6 |
| (P162) | 1231-24 | 1.6 | 25.6 |
| (P163) | 1231-25 | 0.8 | 25.6 |

[1]Antimicrobial activity is expressed as IC99.9 (µM), i.e., the lowest peptide concentration that killed 99.9% of the bacterial inoculum (which was approximately $1 \times 10^6$ CFU/ml *S. aureus* JAR) within 2 hrs.

Antimicrobial Activity of P145, P148 and P159 Against Different Bacteria

In PBS, P145, P148 and P159 had a similar antimicrobial activity against all bacterial species in mid-logarithmic culture as OP-145 (Table 3). In the presence of 50% plasma, P145, P148 and P159 showed higher bactericidal activity against *S. aureus* JAR060131 (11-16-fold), MRSA LUH14616 (21-26-fold), *S. epidermidis* RP62a (43-fold) and *P. aeruginosa* PAO1 (>11-21-fold) as compared to OP-145.

TABLE 3

Antimicrobial activity of OP-145, P145, P148 and P159 in PBS and 50% plasma in mid-logarithmic cultures. Results are expressed as LC99.9, i.e. the lowest peptide concentration (in µM) that resulted in ≥99.9% killing of bacteria. Results are median values of at least two independent experiments.

LC99.9 (µM)

|        | S. aureus JAR060131 | | MRSA LUH14616 | | S. epidermidis RP62a | | P. aeruginosa PAO1 | |
|--------|------|-------------|------|-------------|------|-------------|------|-------------|
|        | PBS  | 50% plasma  | PBS  | 50% plasma  | PBS  | 50% plasma  | PBS  | 50% plasma  |
| OP-145 | 1.6  | 204.8       | 1.6  | 204.8       | 0.8  | 204.8       | 3.2  | >204.8      |
| P145   | 1.6  | 19.2        | 1.6  | 9.6         | 0.8  | 3.2         | 1.6  | 25.6        |
| P148   | 1.6  | 19.2        | 1.6  | 8.0         | 0.8  | 3.2         | 1.6  | 12.8        |
| P159   | 2.4  | 12.8        | 2.4  | 9.6         | 1.6  | 3.2         | 1.6  | 12.8        |

OP-145, P145, P148 and P159 showed similar antimicrobial activity against stationary *S. aureus* JAR060131 (Table 4) as compared to logarithmic bacteria. Thus, in the presence of 50% plasma, P145, P148 and P159 showed higher bactericidal activity against *S. aureus* JAR060131 than OP-145.

TABLE 4

Antimicrobial activity of OP-145, P145, P148 and P159 in PBS and 50% plasma against a stationary suspension of *S. aureus* JAR060131. Results are mean values of three independent experiments.

| | LC99.9 (µM) | |
|---|---|---|
| | PBS | 50% plasma |
| OP-145 | 1.6 | >204.8 |
| P145 | 1.6 | 25.6 |
| P148 | 1.6 | 12.8 |
| P159 | 2.4 | 25.6 |

Antimicrobial Activity of Length Variants of P148

Deletion of 4 amino acids at the C- and N-terminus of P148 has no effect on the antimicrobial activity against *S. aureus* JAR060131 (Table 5). Deleting 5 amino acids at the C- and N-terminus reduces antimicrobial activity as compared to P148, but activity is still 5-fold increased as compared to OP-145.

TABLE 5

Antimicrobial activity of length variants of P148 in PBS and 50% plasma.

| Peptide | Sequence | LC99.9 (µM) PBS | LC99.9 (µM) 50% plasma |
|---|---|---|---|
| P148 | J L K R V W K R V F K L L K R Y W R Q L K K P V R B | 1.6 | 12.8 |
| P325 |         J R V W K R V F K L L K R Y W R Q L K K P V R B | 1.6 | 9.6 |
| P326 | J L K R V W K R V F K L L K R Y W R Q L K K P B | 1.6 | 12.8 |
| P327 |         J R V W K R V F K L L K R Y W R Q L K K P B | 1.6 | 8.0 |
| P328 |             J W K R V F K L L K R Y W R Q L K K P V R B | 1.6 | 12.8 |
| P329 | J L K R V W K R V F K L L K R Y W R Q L K B | 0.8 | 9.6 |
| P330 |             J V W K R V F K L L K R Y W R Q L K K B | 1.6 | 9.6 |
| P331 |             J W K R V F K L L K R Y W R Q L K B | 1.6 | 9.6 |
| P332 |                 J K R V F K L L K R Y W R Q L B | 4.8 | 38.4 |

Results are expressed as LC99.9, i.e. the lowest peptide concentration (in µM) that resulted in ≥ 99.9% killing of *S. aureus*.
Results are mean values of two independent experiments.
J = acetyl, B = amide Antimicrobial Activity of P145, P148 and P159 with Multiple Alanine Substitutions Substitution of one amino acid of P145, P148 and P159 and of two amino acids of P148 by alanine has no effect on the antimicrobial activity against *S. aureus* JAR060131 (Tables 6-9).

TABLE 6

Antimicrobial activity of P145 with an alanine substitution at different positions in PBS and 50% plasma. Results of two independent experiments.

| Peptide | Run# | Sequence | LC99.9 (uM) 2013.01.15 PBS | 50% plasma | 2013.01.18 PBS | 50% plasma |
|---|---|---|---|---|---|---|
| P145 | 1255-04 | J L K R L Y K R L A K L I K R L Y R Y L K K P V R B | 1.6 | 25.6 | 1.6 | 12.8 |
| P246 | 1255-05 | J A K R L Y K R L A K L I K R L Y R Y L K K P V R B | 1.6 | 51.2 | 1.6 | 12.8 |
| P247 | 1255-06 | J L A R L Y K R L A K L I K R L Y R Y L K K P V R B | 1.6 | 51.2 | 0.8 | 12.8 |
| P248 | 1255-07 | J L K A L Y K R L A K L I K R L Y R Y L K K P V R B | 1.6 | 51.2 | 0.8 | 25.6 |
| P249 | 1255-08 | J L K R A Y K R L A K L I K R L Y R Y L K K P V R B | 1.6 | 25.6 | 1.6 | 12.8 |
| P250 | 1255-09 | J L K R L A K R L A K L I K R L Y R Y L K K P V R B | 1.6 | 51.2 | 1.6 | 25.6 |
| P251 | 1255-10 | J L K R L Y A R L A K L I K R L Y R Y L K K P V R B | 1.6 | 51.2 | 1.6 | 25.6 |
| P252 | 1255-11 | J L K R L Y K A L A K L I K R L Y R Y L K K P V R B | 1.6 | 51.2 | 0.8 | 12.8 |
| P253 | 1255-12 | J L K R L Y K R A A K L I K R L Y R Y L K K P V R B | 1.6 | 25.6 | 1.6 | 6.4 |
| P254 | 1255-13 | J L K R L Y K R L A K L I K R L Y R Y L K K P V R B | 1.6 | 51.2 | 0.8 | 12.8 |
| P255 | 1255-14 | J L K R L Y K R L A A L I K R L Y R Y L K K P V R B | 1.6 | 51.2 | 0.8 | 25.6 |
| P256 | 1255-15 | J L K R L Y K R L A K A I K R L Y R Y L K K P V R B | 1.6 | 51.2 | 1.6 | 12.8 |
| P257 | 1255-16 | J L K R L Y K R L A K L A K R L Y R Y L K K P V R B | 1.6 | 25.6 | 0.8 | 12.8 |
| P258 | 1255-17 | J L K R L Y K R L A K L I A R L Y R Y L K K P V R B | 1.6 | 51.2 | 0.8 | 12.8 |
| P259 | 1255-18 | J L K R L Y K R L A K L I K A L Y R Y L K K P V R B | 1.6 | 51.2 | 0.8 | 12.8 |
| P260 | 1255-19 | J L K R L Y K R L A K L I K R A Y R Y L K K P V R B | 1.6 | 25.6 | 1.6 | 12.8 |
| P261 | 1255-20 | J L K R L Y K R L A K L I K R L A R Y L K K P V R B | 1.6 | 25.6 | 1.6 | 12.8 |
| P262 | 1255-21 | J L K R L Y K R L A K L I K R L Y A Y L K K P V R B | 1.6 | 51.2 | 1.6 | 12.8 |
| P263 | 1255-22 | J L K R L Y K R L A K L I K R L Y R A L K K P V R B | 1.6 | 25.6 | 0.8 | 12.8 |
| P264 | 1255-23 | J L K R L Y K R L A K L I K R L Y R Y A K K P V R B | 1.6 | 25.6 | 1.6 | 12.8 |
| P265 | 1255-24 | J L K R L Y K R L A K L I K R L Y R Y L A K P V R B | 1.6 | 51.2 | 0.8 | 12.8 |
| P266 | 1255-25 | J L K R L Y K R L A K L I K R L Y R Y L K A P V R B | 1.6 | 51.2 | 0.8 | 25.6 |
| P267 | 1255-26 | J L K R L Y K R L A K L I K R L Y R Y L K K A V R B | 1.6 | 25.6 | 0.8 | 6.4 |
| P268 | 1255-27 | J L K R L Y K R L A K L I K R L Y R Y L K K P A R B | 1.6 | 51.2 | 0.8 | 12.8 |
| P269 | 1255-28 | J L K R L Y K R L A K L I K R L Y R Y L K K P V A B | 1.6 | 51.2 | 0.8 | 12.8 |

J = acetyl, B = amide

TABLE 7

Antimicrobial activity of P148 with an alanine substitution at different positions in PBS and 50% plasma. Results of two independent experiments.

| Peptide | Run# | Sequence | LC99.9 (uM) 2013.01.15 PBS | 50% plasma | 2013.01.18 PBS | 50% plasma |
|---|---|---|---|---|---|---|
| P148 | 1255-29 | J L K R V W K R V F K L L K R Y W R Q L K K P V R B | 1.6 | 25.6 | 1.6 | 12.8 |
| P270 | 1255-30 | J A K R V W K R V F K L L K R Y W R Q L K K P V R B | 1.6 | 25.6 | 0.8 | 6.4 |
| P271 | 1255-31 | J L A R V W K R V F K L L K R Y W R Q L K K P V R B | 1.6 | 51.2 | 1.6 | 12.8 |
| P272 | 1255-32 | J L K A V W K R V F K L L K R Y W R Q L K K P V R B | 1.6 | 51.2 | 1.6 | 12.8 |
| P273 | 1255-33 | J L K R A W K R V F K L L K R Y W R Q L K K P V R B | 1.6 | 25.6 | 1.6 | 6.4 |
| P274 | 1255-34 | J L K R V A K R V F K L L K R Y W R Q L K K P V R B | 1.6 | 25.6 | 1.6 | 6.4 |
| P275 | 1255-35 | J L K R V W A R V F K L L K R Y W R Q L K K P V R B | 1.6 | 25.6 | 1.6 | 12.8 |
| P276 | 1255-36 | J L K R V W K A V F K L L K R Y W R Q L K K P V R B | 1.6 | 12.8 | 0.8 | 6.4 |
| P277 | 1255-37 | J L K R V W K R A F K L L K R Y W R Q L K K P V R B | 1.6 | 25.6 | 1.6 | 6.4 |
| P278 | 1255-38 | J L K R V W K R V A K L L K R Y W R Q L K K P V R B | 1.6 | 25.6 | 1.6 | 6.4 |
| P279 | 1255-39 | J L K R V W K R V F A L L K R Y W R Q L K K P V R B | 1.6 | 51.2 | 0.8 | 12.8 |
| P280 | 1255-40 | J L K R V W K R V F K A L K R Y W R Q L K K P V R B | 1.6 | 25.6 | 1.6 | 6.4 |
| P281 | 1255-41 | J L K R V W K R V F K L A K R Y W R Q L K K P V R B | 1.6 | 25.6 | 1.6 | 6.4 |
| P282 | 1255-42 | J L K R V W K R V F K L L A R Y W R Q L K K P V R B | 1.6 | 51.2 | 1.6 | 25.6 |
| P283 | 1255-43 | J L K R V W K R V F K L L K A Y W R Q L K K P V R B | 1.6 | 25.6 | 1.6 | 12.8 |
| P284 | 1255-44 | J L K R V W K R V F K L L K R A W R Q L K K P V R B | 1.6 | 25.6 | 0.8 | 12.8 |
| P285 | 1255-45 | J L K R V W K R V F K L L K R Y A R Q L K K P V R B | 1.6 | 12.8 | 1.6 | 12.8 |
| P286 | 1255-46 | J L K R V W K R V F K L L K R Y W A Q L K K P V R B | 1.6 | 51.2 | 1.6 | 12.8 |
| P287 | 1255-47 | J L K R V W K R V F K L L K R Y W R A L K K P V R B | 1.6 | 51.2 | 0.8 | 12.8 |
| P288 | 1255-48 | J L K R V W K R V F K L L K R Y W R Q A K K P V R B | 1.6 | 25.6 | 1.6 | 12.8 |
| P289 | 1255-49 | J L K R V W K R V F K L L K R Y W R Q L A K P V R B | 1.6 | 51.2 | 1.6 | 25.6 |
| P290 | 1255-50 | J L K R V W K R V F K L L K R Y W R Q L K A P V R B | 1.6 | 25.6 | 0.8 | 12.8 |
| P291 | 1255-51 | J L K R V W K R V F K L L K R Y W R Q L K K A V R B | 1.6 | 25.6 | 0.8 | 12.8 |
| P292 | 1255-52 | J L K R V W K R V F K L L K R Y W R Q L K K P A R B | 0.8 | 25.6 | 0.8 | 12.8 |
| P293 | 1255-53 | J L K R V W K R V F K L L K R Y W R Q L K K P V A B | 0.8 | 25.6 | 0.8 | 12.8 |

J = acetyl, B = amide

Antimicrobial activity of P159 with an alanine substitution at different positions in PBS and 50% plasma. Results of two independent experiments.

| Peptide | Run# | Sequence | LC99.9 (uM) 2013.01.15 PBS | 50% plasma | 2013.01.18 PBS | 50% plasma |
|---|---|---|---|---|---|---|
| P159 | 1255-54 | J L K R V W K R V F K L L K R Y W R Q L K K P V R B | 1.6 | 25.6 | 1.6 | 12.8 |
| P294 | 1255-55 | J A K R V W K R V F K L L K R Y W R Q L K K P V R B | 1.6 | 25.6 | 3.2 | 12.8 |

-continued

Antimicrobial activity of P159 with an alanine substitution at different positions in PBS and 50% plasma. Results of two independent experiments.

| Peptide | Run# | Sequence | LC99.9 (uM) 2013.01.15 PBS | 50% plasma | 2013.01.18 PBS | 50% plasma |
|---|---|---|---|---|---|---|
| P295 | 1255-56 | J L A R V W K R V F K L L K R Y W R Q L K K P V R B | 1.6 | 51.2 | 3.2 | 25.6 |
| P296 | 1255-57 | J L K A V W K R V F K L L K R Y W R Q L K K P V R B | 1.6 | 25.6 | 1.6 | 12.8 |
| P297 | 1255-58 | J L K R A W K R V F K L L K R Y W R Q L K K P V R B | 1.6 | 12.8 | 3.2 | 12.8 |
| P298 | 1255-59 | J L K R V A K R V F K L L K R Y W R Q L K K P V R B | 3.2 | 51.2 | 3.2 | 25.6 |
| P299 | 1255-60 | J L K R V W A R V F K L L K R Y W R Q L K K P V R B | 1.6 | 25.6 | 1.6 | 25.6 |
| P300 | 1255-61 | J L K R V W K A V F K L L K R Y W R Q L K K P V R B | 1.6 | 51.2 | 1.6 | 25.6 |
| P301 | 1255-62 | J L K R V W K R A F K L L K R Y W R Q L K K P V R B | 1.6 | 25.6 | 3.2 | 12.8 |
| P302 | 1255-63 | J L K R V W K R V A K L L K R Y W R Q L K K P V R B | 1.6 | 51.2 | 1.6 | 25.6 |
| P303 | 1255-64 | J L K R V W K R V F A L L K R Y W R Q L K K P V R B | 1.6 | 25.6 | 1.6 | 25.6 |
| P304 | 1255-65 | J L K R V W K R V F K A L K R Y W R Q L K K P V R B | 3.2 | 25.6 | 3.2 | 25.6 |
| P305 | 1255-66 | J L K R V W K R V F K L A K R Y W R Q L K K P V R B | 3.2 | 12.8 | 1.6 | 6.4 |
| P306 | 1255-67 | J L K R V W K R V F K L L A R Y W R Q L K K P V R B | 1.6 | 51.2 | >3.2 | 25.6 |
| P307 | 1255-68 | J L K R V W K R V F K L L K A Y W R Q L K K P V R B | 1.6 | 51.2 | 1.6 | 12.8 |
| P308 | 1255-69 | J L K R V W K R V F K L L K R A W R Q L K K P V R B | 3.2 | 51.2 | 3.2 | 12.8 |
| P309 | 1255-70 | J L K R V W K R V F K L L K R Y A R Q L K K P V R B | 1.6 | 51.2 | 1.6 | 12.8 |
| P310 | 1255-71 | J L K R V W K R V F K L L K R Y W A Q L K K P V R B | 1.6 | 51.2 | 1.6 | 12.8 |
| P311 | 1255-72 | J L K R V W K R V F K L L K R Y W R A L K K P V R B | 1.6 | 51.2 | 3.2 | 25.6 |
| P312 | 1255-73 | J L K R V W K R V F K L L K R Y W R Q A K K P V R B | 3.2 | 51.2 | 3.2 | 12.8 |
| P313 | 1255-74 | J L K R V W K R V F K L L K R Y W R Q L A K P V R B | 1.6 | 51.2 | 1.6 | 12.8 |
| P314 | 1255-75 | J L K R V W K R V F K L L K R Y W R Q L K A P V R B | 1.6 | 51.2 | 1.6 | 12.8 |
| P315 | 1255-76 | J L K R V W K R V F K L L K R Y W R Q L K K A V R B | 3.2 | >51.2 | 1.6 | 12.8 |
| P316 | 1255-77 | J L K R V W K R V F K L L K R Y W R Q L K K P A R B | 1.6 | 25.6 | 3.2 | 12.8 |
| P317 | 1255-78 | J L K R V W K R V F K L L K R Y W R Q L K K P V A B | 1.6 | 51.2 | 1.6 | 12.8 |

J = acetyl, B = amide

TABLE 9

Antimicrobial activity of P148 with multiple alanine substitutions in PBS and 50% plasma.

| Peptide | Sequence | LC99.9 (µM) PBS | 50% plasma |
|---|---|---|---|
| P148 | J L K R V W K R V F K L L K R Y W R Q L K K P V R B | 1.2 | 19.2 |
| P318 | J A K R V W K A V F K L L K R Y W R Q L K K P V R B | 1.2 | 19.2 |
| P319 | J L K R A W K A V F K L L K R Y W R Q L K K P V R B | 1.2 | 19.2 |
| P320 | J L K R V A K A V F K L L K R Y W R Q L K K P V R B | 1.2 | 19.2 |
| P321 | J L K R V W K A A F K L L K R Y W R Q L K K P V R B | 1.2 | 19.2 |

TABLE 9-continued

Antimicrobial activity of P148 with multiple alanine substitutions in PBS and 50% plasma.

| Peptide | Sequence | LC99.9 (μM) PBS | 50% plasma |
|---|---|---|---|
| P322 | J L K R V W K A V A K L L K R Y W R Q L K K P V R B | 1.2 | 19.2 |
| P323 | J L K R V W K A V F K A L K R Y W R Q L K K P V R B | 1.2 | 19.2 |
| P324 | J L K R V W K A V F K L A K R Y W R Q L K K P V R B | 1.2 | 19.2 |

Results are mean values of two independent experiments.
J = acetyl, B = amide

Antimicrobial Activity of P148 Variants with Positively Charged Amino Acid Substitutions P148 variants wherein lysine or arginine has been replaced by a positively charged amino acid retain antimicrobial activity against *S. aureus* both in PBS and in the presence of 50% plasma (Table 10).

TABLE 10

Antimicrobial activity of P148 with positively charged amino acid substitutions in PBS and 50% plasma.

| Peptide | Sequence | LC99.9 (μM) PBS | 50% plasma |
|---|---|---|---|
| P148 | J L K R V W K R V F K L L K R Y W R Q L K K P V R B | 0.8 | 12.8 |
| P365 | J L O R V W K R V F K L L K R Y W R Q L K K P V R B | 0.8 | 12.8 |
| P366 | J L K O V W K R V F K L L K R Y W R Q L K K P V R B | 0.8 | 12.8 |
| P367 | J L K R V W O R V F K L L K R Y W R Q L K K P V R B | 0.8 | 12.8 |
| P368 | J L K R V W K O V F K L L K R Y W R Q L K K P V R B | 0.8 | 12.8 |
| P369 | J L K R V W K R V F O L L K R Y W R Q L K K P V R B | 0.8 | 12.8 |
| P370 | J L K R V W K R V F K L L O R Y W R Q L K K P V R B | 0.8 | 25.6 |
| P371 | J L K R V W K R V F K L L K O Y W R Q L K K P V R B | 0.8 | 25.6 |
| P372 | J L K R V W K R V F K L L K R Y W O Q L K K P V R B | 0.8 | 25.6 |
| P373 | J L K R V W K R V F K L L K R Y W R Q L O K P V R B | 0.8 | 25.6 |
| P374 | J L K R V W K R V F K L L K R Y W R Q L K O P V R B | 0.8 | 25.6 |
| P375 | J L K R V W K R V F K L L K R Y W R Q L K K P V O B | 0.8 | 12.8 |
| P377 | J L X R V W K R V F K L L K R Y W R Q L K K P V R B | 0.8 | 12.8 |
| P378 | J L K X V W K R V F K L L K R Y W R Q L K K P V R B | 0.8 | 12.8 |
| P379 | J L K R V W X R V F K L L K R Y W R Q L K K P V R B | 0.8 | 12.8 |
| P380 | J L K R V W K X V F K L L K R Y W R Q L K K P V R B | 0.8 | 12.8 |
| P381 | J L K R V W K R V F X L L K R Y W R Q L K K P V R B | 0.8 | 25.6 |
| P382 | J L K R V W K R V F K L L X R Y W R Q L K K P V R B | 0.8 | 25.6 |
| P383 | J L K R V W K R V F K L L K X Y W R Q L K K P V R B | 0.8 | 25.6 |
| P384 | J L K R V W K R V F K L L K R Y W X Q L K K P V R B | 1.6 | 25.6 |
| P385 | J L K R V W K R V F K L L K R Y W R Q L X K P V R B | 0.8 | 12.8 |
| P386 | J L K R V W K R V F K L L K R Y W R Q L K X P V R B | 0.8 | 25.6 |
| P387 | J L K R V W K R V F K L L K R Y W R Q L K K P V X B | 1.6 | 25.6 |
| P389 | J L U R V W K R V F K L L K R Y W R Q L K K P V R B | 0.8 | 12.8 |
| P390 | J L K U V W K R V F K L L K R Y W R Q L K K P V R B | 1.6 | 12.8 |
| P391 | J L K K R V W U R V F K L L K R Y W R Q L K P V R B | 0.8 | 25.6 |
| P392 | J L K R V W K U V F K L L K R Y W R Q L K K P V R B | 0.8 | 12.8 |
| P393 | J L K R V W K R V F U L L K R Y W R Q L K K P V R B | 0.8 | 25.6 |
| P394 | J L K R V W K R V F K L L U R Y W R Q L K K P V R B | 0.8 | 25.6 |
| P395 | J L K R V W K R V F K L L K U Y W R Q L K K P V R B | 1.6 | 25.6 |
| P396 | J L K R V W K R V F K L L K R Y W U Q L K K P V R B | 0.8 | 25.6 |
| P397 | J L K R V W K R V F K L L K R Y W R Q L U K P V R B | 0.8 | 25.6 |
| P398 | J L K R V W K R V F K L L K R Y W R Q L K U P V R B | 1.6 | 25.6 |
| P399 | J L K R V W K R V F K L L K R Y W R Q L K K P V U B | 3.2 | 51.2 |

J = acetyl, O = ornithine;
X = diaminobutyric acid (DABA);
U = diaminopropionic acid (DAPA), B = amide.

Antifungal Activity of P145, P148 and P159

OP-145 showed no antifungal activity against *C. albicans* Y-O1 in PBS at 51.2 μM (Table 11). P145, P148 and P159 killed 99% of *C. albicans* at concentrations ranging from 12.8 ηµM (for P159) to 38.4 µM (for P148). In 50% plasma, antifungal activity was 204.8 µM for P145, P148 and P159. At this concentration, no antifungal activity was observed for OP-145.

TABLE 11

Antifungal activity of OP-145, P145, P148 and P159 in PBS and 50% plasma. Results are mean values of two independent experiments.

| | LC99 (µM) | |
|---|---|---|
| | PBS | 50% plasma |
| OP-145 | >51.2 | >204.8 |
| P145 | 25.6 | 204.8 |
| P148 | 38.4 | 204.8 |
| P159 | 12.8 | 204.8 |

Figure 2:
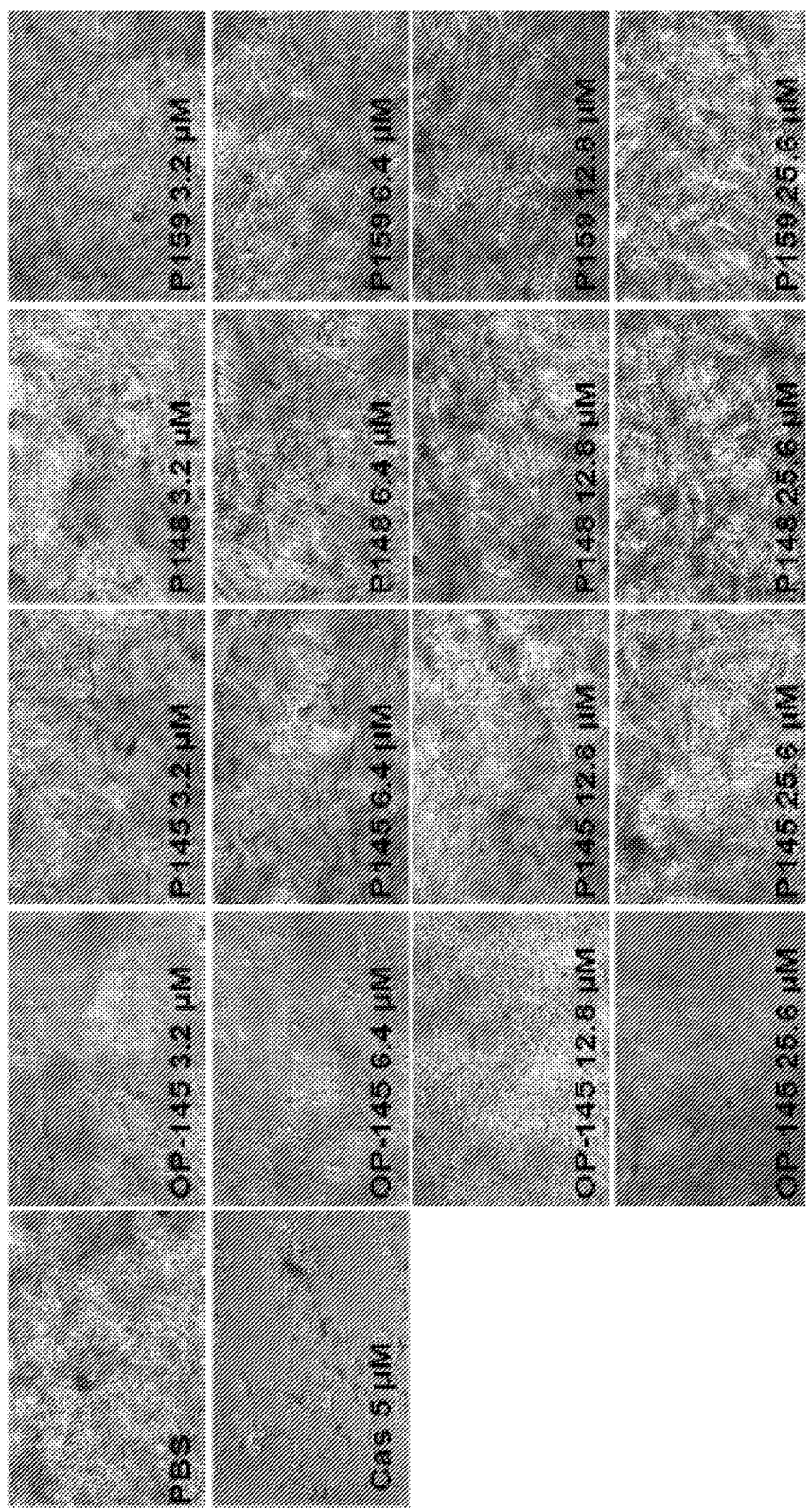
FIG. 2: Light micrographs of *A. niger* growth in 25% plasma after 16 hours of incubation with PBS, Cancidas, OP-145 or the indicated peptides. Representative light micrographs of triplicates.

OP-145 inhibited *A. niger* growth by >99.9% at concentrations of 3.2 µM (FIG. 1). P145 showed similar antifungal activity as OP-145, whereas P148 had a 4-fold higher antifungal activity, inhibiting fungal growth already at 0.8 µM. P159 had a 2-fold lower antifungal activity as compared to OP-145. As plasma influenced the optical density values, the antifungal activity of the peptides in the presence of plasma was assessed based on the light micrographs only. In the presence of 25% plasma, fungal growth was inhibited by 204.8 µM of OP-145 (FIG. 2). P145, P148 and P159 inhibited growth at 102.4 µM.

Antibiofilm Activity of P145, P148 and P159

Figure 3:
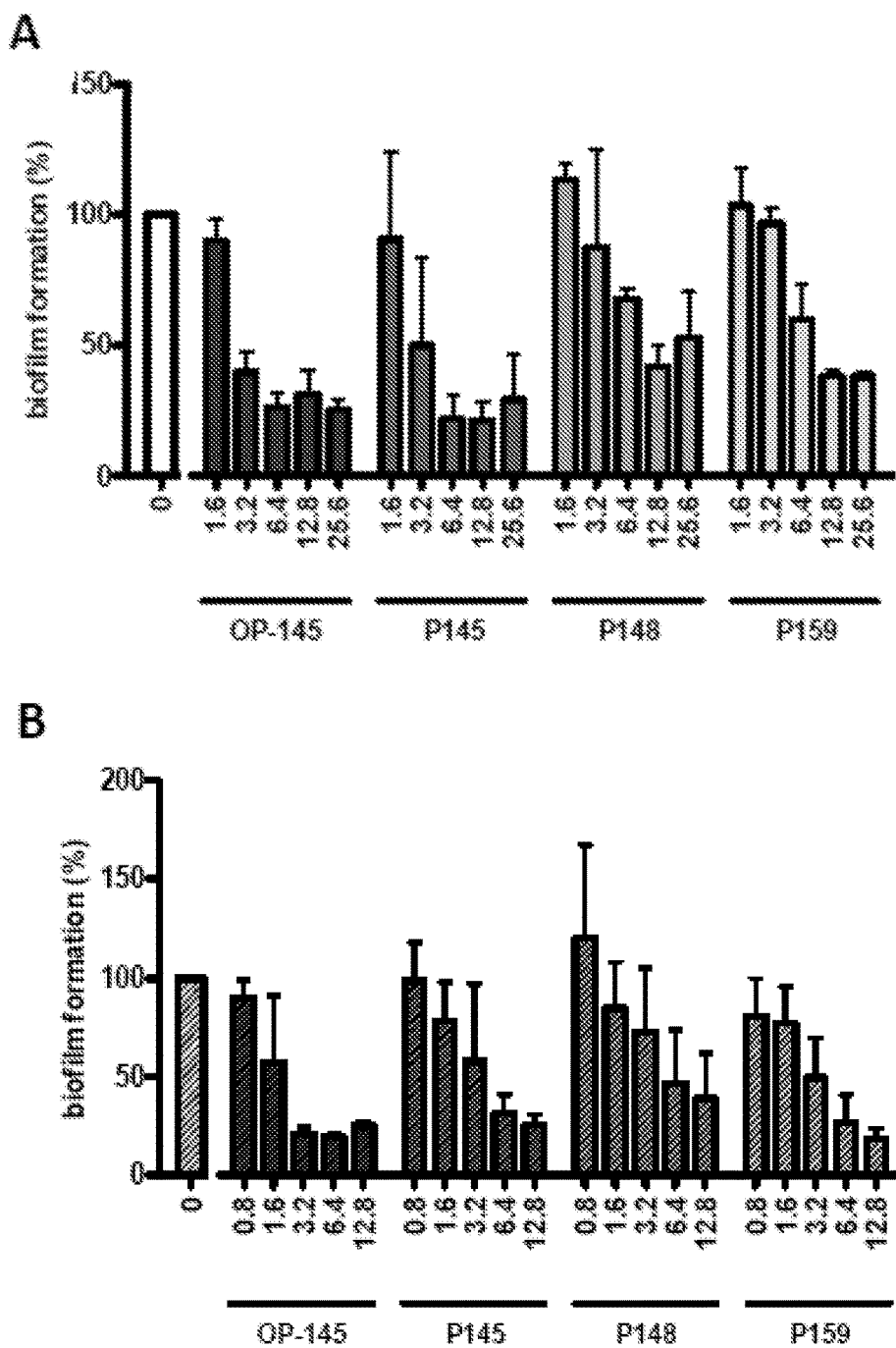
FIG. 3: Inhibition of biofilm formation by *S. aureus* JAR060131 at different concentrations (in µM). Results are expressed as mean percentage biofilm mass relative to the untreated sample (0)±standard deviations of three independent experiments. A, biofilm formation in uncoated wells. B, biofilm formation in plasma-coated wells.

OP-145 showed ≥50% inhibition of biofilm formation at 3.2 µM (FIG. 3A). The IC50 value for P145 was 6.4 µM and for P148 and P159 12.8 µM. The maximal biofilm inhibition was approximately 75%. Of note, in biofilm-adjusted BM2 medium, these peptides did not show antimicrobial activity up to 51.2 µM. In plasma-coated wells, 3.2 µM of OP-145 and P159 inhibited biofilm formation for 50%, whereas a two-fold higher concentration was needed for P145 and P148 to inhibit biofilm formation for 50% (FIG. 3B). Maximal biofilm inhibition in the presence of plasma ranged from 61% (for P148) to 82% (for P159).

Immunodulatory Activity: LPS and LTA Neutralization by P145, P148 and P159

The IC50 and IC90 of OP-145 were 0.15 nM and 1.25 nM, respectively. P148 inhibited >50% of LPS-induced IL-12p40 production already at 0.03 nM and P159 at 0.05 nM. Ninety percent inhibition of LPS-induced IL-12p40 was reached with 0.25 nM of P148 and P159 and 0.75 nM of P145 (Table 11). The ability of the peptides to neutralize LTA was assessed by measuring the inhibition of LTA-induced IL-8 production by blood cells. At a final concentration of 0.781 µM, OP-145 inhibited >50% of IL-8 production induced by 5 µg/ml LTA (Table 11). P145, P148 and P159 had a 4-fold increased LTA-neutralizing ability. Peptides were also pre-incubated with UV-killed bacteria of *S. aureus* JAR060131. Incubation with 0.195 µM of OP-145 resulted in >50% reduction of IL-8 production induced by *S. aureus* JAR (Table 12). P159 had a similar neutralizing activity as OP-145, whereas an 8-fold higher concentration of P145 and P148 was needed to inhibit *S. aureus*-induced IL-8 production for >50% (Table 12).

TABLE 12

LPS, LTA and *S. aureus* neutralizing activity of OP-145, P145, P148 and P159. For LPS neutralization, the experiment was performed using blood from two donors. For LTA and *S. aureus* neutralization, the experiment was performed using blood from one donor.

| Peptide | LPS neutralization (IC90 in nM) | LTA neutralization (IC50 in µM) | *S. aureus* neutralization (IC50 in µM) |
|---|---|---|---|
| OP-145 | 1.25 | 0.781 | 0.195 |
| P145 | 0.75 | 0.195 | 1.563 |
| P148 | 0.25 | 0.195 | 1.563 |
| P159 | 0.25 | 0.195 | 0.195 |

The invention claimed is:

1. A polypeptide comprising the amino acid sequence LKKLYKRLVKILKRWWRYLKRPVR (SEQ ID NO: 1), or comprising a variant of said amino acid sequence,
   said polypeptide having antibacterial, antiviral, antifungal and/or antiparasitic activity and having an in vitro, antibacterial, antiviral, antifungal and/or antiparasitic activity against at least one microbial species in the presence of 50% plasma that is at least 1.3-fold higher than the activity of OP-145 under the same conditions,
   the variant of said amino acid sequence comprising at least 14 amino acids, comprising the sequence KRLVKILKRWWRYL (SEQ ID NO: 3), and optionally having:
   1 to 7 of the following amino acid substitutions:
      substitution of one or more amino acids selected from the group of L, V, F, A, I, W, Y and Q by another amino acid selected from said group;
      substitution of R and/or K by A or a positively charged amino acid;
      and/or
      one substitution of an amino acid by a corresponding non-natural amino acid, whereby said corresponding non-natural amino acid is a derivative of the reference natural amino acid.

2. The polypeptide according to claim 1, wherein said substitution of an amino acid by a corresponding non-natural amino acid is selected from the group consisting of:
   substitution of an amino acid by the corresponding β amino acid;
   substitution of R by homoarginine, ornithine, N5-carbamoylornithine or 3-amino-propionic acid;
   substitution of I by isodesmosine, N-methylisoleucine or allo-isoleucine;
   substitution of L by norleucine, desmosine or 5,5,5-trifluoro-leucine;
   substitution of K by 6-N-methyllysine, 2-aminoheptanoic acid, N-acetyl lysine, hydroxylysine or allo-hydroxylysine;
   substitution of P by 3-hydroxyproline, 4-hydroxyproline or 1-acetyl-4-hydroxy-L-proline;
   substitution of W by 5-hydroxy-tryptophan, 5-methoxy-tryptophan or 5-fluoro-tryptophan;
   substitution of Y by O-methyl-L-tyrosine, O-4-allyl-L-tyrosine or 3-chloro-tyrosine; and
   substitution of V by norvaline, N-methylvaline or 3-fluoro-valine.

3. The polypeptide according to claim 1, wherein said polypeptide is N-terminally and/or C-terminally modified.

4. The polypeptide according to claim 3, wherein said polypeptide comprises an N-terminal acetyl-, hexanoyl-, decanoyl-, myristoyl-, NH—(CH$_2$—CH$_2$—O)$_{11}$—CO— or propionyl-residue and/or a C-terminal amide-, NH—(CH$_2$—CH$_2$—O)$_{11}$—CO-amide-, or one or two aminohexanoyl groups.

5. A nucleic acid molecule comprising a nucleic acid sequence encoding a polypeptide according to claim 1.

6. A vector comprising the nucleic acid molecule according to claim 5.

7. A recombinant host cell comprising the nucleic acid molecule according to claim 5.

8. A coating for a medical device comprising a polypeptide according to claim 1.

9. A pharmaceutical composition comprising the polypeptide according to claim 1, or a pharmaceutically acceptable salt thereof, and at least one pharmaceutically acceptable carrier, diluent and/or excipient.

10. The pharmaceutical composition according to claim 9, further comprising an additional antibacterial agent, antifungal agent, antiviral agent, or antiparasitic agent.

11. The pharmaceutical composition according to claim 9, further comprising a controlled release and/or targeted delivery carrier comprising said polypeptide.

12. A method of treating or inhibiting a bacterial, fungal, viral, and/or parasitic infection in a mammal and/or a condition resulting from a bacterial, fungal, viral, and/or parasitic infection in a mammal comprising administering to the mammal a therapeutically effective amount of the polypeptide according to claim 1.

13. The method of claim 12, wherein the infection is a biofilm associated infection.

14. A method of treating or inhibiting a bacterial, fungal, viral, and/or parasitic infection in a mammal and/or a condition resulting from a bacterial, fungal, viral, and/or parasitic infection in a mammal comprising administering to the mammal a therapeutically effective amount of a pharmaceutical composition according to claim 9.

15. The method of claim 13, wherein the infection is a biofilm associated infection.

16. A method for the preparation of a polypeptide according to claim 1 comprising:
   providing a nucleic acid molecule comprising a nucleic acid sequence encoding the polypeptide;
   transforming a host cell with said nucleic acid molecule;
   culturing said host cell under conditions that allow expression of said polypeptide;
   harvesting said polypeptide from said cells; and
   optionally N-terminally or C-terminally modifying said polypeptide.

* * * * *